US 7,973,181 B2

(12) United States Patent
Davidson et al.

(10) Patent No.: US 7,973,181 B2
(45) Date of Patent: *Jul. 5, 2011

(54) HYDROXAMIC ACID DERIVATIVES AS INHIBITORS OF HDAC ENZYMATIC ACTIVITY

(75) Inventors: Alan Hornsby Davidson, Abingdon (GB); Sanjay Ratilal Patel, Abingdon (GB); David Festus Charles Moffat, Abingdon (GB)

(73) Assignee: Chroma Therapeutics Ltd. (GB)

( * ) Notice: Subject to any disclaimer, the term of this patent is extended or adjusted under 35 U.S.C. 154(b) by 644 days.

This patent is subject to a terminal disclaimer.

(21) Appl. No.: 11/919,048

(22) PCT Filed: May 4, 2006

(86) PCT No.: PCT/GB2006/001602
§ 371 (c)(1),
(2), (4) Date: Oct. 23, 2007

(87) PCT Pub. No.: WO2006/117548
PCT Pub. Date: Nov. 9, 2006

(65) Prior Publication Data
US 2009/0298924 A1    Dec. 3, 2009

(30) Foreign Application Priority Data
May 5, 2005 (GB) .................................. 0509225.9

(51) Int. Cl.
*C07D 333/70* (2006.01)
*C07C 229/36* (2006.01)
(52) U.S. Cl. ............. 549/57; 514/443; 514/542; 560/39
(58) Field of Classification Search .................. 514/443, 514/542; 549/57; 560/39
See application file for complete search history.

(56) References Cited

U.S. PATENT DOCUMENTS

| 2004/0092558 A1 | 5/2004 | Klimko et al. | |
| 2009/0291978 A1* | 11/2009 | Davidson et al. | 514/300 |
| 2010/0010010 A1* | 1/2010 | Davidson et al. | 514/255.01 |

FOREIGN PATENT DOCUMENTS

| WO | WO 01/18171 A2 | 3/2001 |
| WO | WO 02/090534 A1 | 11/2002 |
| WO | WO 03/070188 A2 | 8/2003 |

OTHER PUBLICATIONS

Vippagunta et al., Advanced Drug Delivery Reviews, vol. 48, (2001), pp. 3-26.*

* cited by examiner

Primary Examiner — Yong Chu
(74) Attorney, Agent, or Firm — Banner & Witcoff, Ltd.

(57) ABSTRACT

Compounds of formula (I) are inhibitors of histone deacetylase activity, and are useful in the treatment of, for example, cancers:

$$R-L^1-Y^1-[CH_2]_z-(A)-[Linker]-CONHOH \quad (II)$$

wherein $Y^1$ is a bond, —(C=O)—, —S(O$_2$)—, —C(=O)O—, —OC(=O)—, —(C=O)NR$_3$—, —NR$_3$(C=O)—, —S(O$_2$)NR$_3$—, —NR$_3$S(O$_2$)—, or —NR$_3$(C=O)NR$_5$—, wherein $R_3$ and $R_5$ are independently hydrogen or optionally substituted (C$_1$-C$_6$)alkyl, $L^1$ is a divalent radical of formula -(Alk$^1$)$_m$(Q)$_n$(Alk$^2$)$_p$ wherein m, n, p, Alk$^1$, Alk$^2$ and Q are as defined in the claims; z is 0 or 1; A represents an optionally substituted mono-, bi— or tri-cyclic carbocyclic or heterocyclic ring system; -[Linker]- represents a divalent linker radical; R is a radical of formula (X) or (Y):

(X)

(Y)

wherein $R_1$ is a carboxylic acid group (—COOH), or an ester group which is hydrolysable by one or more intracellular carboxylesterase enzymes to a carboxylic acid group; $R_4$ is hydrogen; or optionally substituted C$_1$-C$_6$ alkyl, C$_3$-C$_7$cycloalkyl, aryl, aryl(C$_1$-C$_6$ alkyl)-, heteroaryl, heteroaryl(C$_1$-C$_6$ alkyl)-, —(C=O)R$_3$, —(C=O)OR$_3$, or —(C=O)NR$_3$ wherein R$_3$ is hydrogen or optionally substituted (C$_1$-C$_6$)alkyl, C$_3$-C$_7$ cycloalkyl, aryl, aryl(C$_1$-C$_6$ alkyl)-, heteroaryl, or heteroaryl(C$_1$-C$_6$ alkyl)-; $R_4^1$ is hydrogen or optionally substituted C$_1$-C$_6$ alkyl; and B is a monocyclic heterocyclic ring of 5 or 6 ring atoms wherein R$_1$ is linked to a ring carbon adjacent the ring nitrogen shown, and ring B is optionally fused to a second carbocyclic or heterocyclic ring of 5 or 6 ring atoms in which case the bond shown intersected by a wavy line may be from a ring atom in said second ring.

21 Claims, No Drawings

HYDROXAMIC ACID DERIVATIVES AS INHIBITORS OF HDAC ENZYMATIC ACTIVITY

CROSS REFERENCE TO RELATED APPLICATIONS

This application is a National Stage application of co-pending PCT application PCT/GB2006/001602 filed May 4, 2006, which claims the benefit of Great Britain application number 0509225.9 filed May 5, 2005. These applications are incorporated herein by reference in their entireties.

This invention relates to compounds which inhibit members of the histone deacetylase family of enzymes and to their use in the treatment of cell proliferative diseases, including cancers, polyglutamine diseases, for example Huntingdon disease, neurodegenerative diseases for example Alzheimer disease, autoimmune disease for example rheumatoid arthritis and organ transplant rejection, diabetes, haematological disorders, inflammatory disease, cardiovascular disease, atherosclerosis, and the inflammatory sequelae of infection.

BACKGROUND TO THE INVENTION

In eukaryotic cells DNA is packaged with histones, to form chromatin. Approximately 150 base pairs of DNA are wrapped twice around an octamer of histones (two each of histones 2A, 2B, 3 and 4) to form a nucleosome, the basic unit of chromatin. The ordered structure of chromatin needs to be modified in order to allow transcription of the associated genes. Transcriptional regulation is key to differentiation, proliferation and apoptosis, and is, therefore, tightly controlled. Control of the changes in chromatin structure (and hence of transcription) is mediated by covalent modifications to histones, most notably of the N-terminal tails. Covalent modifications (for example methylation, acetylation, phosphorylation and ubiquitination) of the side chains of amino acids are enzymatically mediated (A review of the covalent modifications of histones and their role in transcriptional regulation can be found in Berger S L 2001 Oncogene 20, 3007-3013; See Grunstein, M 1997 Nature 389, 349-352; Wolffe A P 1996 Science 272, 371-372; and Wade P A et al 1997 Trends Biochem Sci 22, 128-132 for reviews of histone acetylation and transcription).

Acetylation of histones is associated with areas of chromatin that are transcriptionally active, whereas nucleosomes with low acetylation levels are, typically, transcriptionally silent. The acetylation status of histones is controlled by two enzyme classes of opposing activities; histone acetyltransferases (HATs) and histone deacetylases (HDACs). In transformed cells it is believed that inappropriate expression of HDACs results in silencing of tumour suppressor genes (For a review of the potential roles of HDACs in tumorigenesis see Gray S G and Teh B T 2001 Curr Mol Med 1, 401-429). Inhibitors of HDAC enzymes have been described in the literature and shown to induce transcriptional reactivation of certain genes resulting in the inhibition of cancer cell proliferation, induction of apoptosis and inhibition of tumour growth in animals (For review see Kelly, W K et al 2002 Expert Opin Investig Drugs 11, 1695-1713). Such findings suggest that HDAC inhibitors have therapeutic potential in the treatment of proliferative diseases such as cancer (Kramer, O H et al 2001 Trends Endocrinol 12, 294-300, Vigushin D M and Coombes R C 2002 Anticancer Drugs 13, 1-13).

In addition, others have proposed that aberrant HDAC activity or histone acetylation is implicated in the following diseases and disorders; polyglutamine disease, for example Huntingdon disease (Hughes R E 2002 Curr Biol 12, R141-R143; McCampbell A et al 2001 Proc Soc Natl Acad Sci 98, 15179-15184; Hockly E et al 2003 Proc Soc Natl Acad Sci 100, 2041-2046), other neurodegenerative diseases, for example Alzheimer disease (Hempen B and Brion J P 1996, J Neuropathol Exp Neurol 55, 964-972), autoimmune disease and organ transplant rejection (Skov S et al 2003 Blood 101, 1430-1438; Mishra N et al 2003 J Clin Invest 111, 539-552), diabetes (Mosley A L and Ozcan S 2003 J Biol Chem 278, 19660-19666) and diabetic complications, infection (including protozoal infection (Darkin-Rattray, S J et al 1996 Proc Soc Natl Acad Sci 93, 13143-13147)) and haematological disorders including thalassemia (Witt O et al 2003 Blood 101, 2001-2007). The observations contained in these manuscripts suggest that HDAC inhibition should have therapeutic benefit in these, and other related, diseases Many types of HDAC inhibitor compounds have been suggested, and several such compounds are currently being evaluated clinically, for the treatment of cancers. For example, the following patent publications disclose such compounds:

| | | |
|---|---|---|
| U.S. Pat. No. 5,369,108 and | WO 03/076395 | WO 04/110989 |
| WO 01/18171 | WO 03/076400 | WO 04/092115 |
| U.S. Pat. No. 4,254,220 | WO 03/076401 | WO 04/0224991 |
| WO 01/70675 | WO 03/076421 | WO 05/014588 |
| WO 01/38322 | WO 03/076430 | WO 05/018578 |
| WO 02/30879 | WO 03/076422 | WO 05/019174 |
| WO 02/26703 | WO 03/082288 | WO 05/004861 |
| WO 02/069947 | WO 03/087057 | WO 05/007091 |
| WO 02/26696 | WO 03/092686 | WO 05/030704 |
| WO 03/082288 | WO 03/066579 | WO 05/013958 |
| WO 02/22577 | WO 03/011851 | WO 05/028447 |
| WO 03/075929 | WO 04/013130 | WO 05/026907 |

Many of the HDAC inhibitors known in the art have a structural template, which may be represented as in formula (A):

(A)

wherein ring A is a carbocyclic or heterocyclic ring system with optional substituents R, and [Linker] is a linker radical of various types. The hydroxamate group functions as a metal binding group, interacting with the metal ion at the active site of the HDAC enzyme, which lies at the base of a pocket in the folded enzyme structure. The ring or ring system A lies within or at the entrance to the pocket containing the metal ion, with the -[Linker]- radical extending deeper into that pocket linking A to the metal binding hydroxamic acid group. In the art, and occasionally herein, the ring or ring system A is sometimes informally referred to as the "head group" of the inhibitor.

The use of prodrugs to enhance the delivery to target organs and tissues, or to overcome poor pharmacokinetic properties of the parent drug, is a well known medicinal chemistry approach. Administration of ester prodrugs, for example, which are hydrolysed by serum carboxylesterases in vivo to the active parent acids, can result in higher serum levels of the parent acid than administration of the acid itself.

BRIEF DESCRIPTION OF THE INVENTION

This invention is based on the finding that the introduction of an alpha amino acid ester grouping into the HDAC inhibitor molecular template (A) above facilitates penetration of the agent through the cell membrane, and thereby allows intracellular carboxylesterase activity to hydrolyse the ester to release the parent acid. Being charged, the acid is not readily transported out of the cell, where it therefore accumulates to increase the intracellular concentration of active HDAC inhibitor. This leads to increases in potency and duration of action. The invention therefore makes available a class of compounds whose structures are characterised by having an alpha amino acid ester moiety which is a substrate for intracellular carboxylesterase (also referred to herein as an "esterase motif") covalently linked to an HDAC inhibitor molecular template, and to the corresponding de-esterified parent acids, such compounds having pharmaceutical utility in the treatment of diseases such as cancers which benefit from intracellular inhibition of HDAC.

DETAILED DESCRIPTION OF THE INVENTION

According to the present invention there is provided a compound of formula (I) or a salt, N-oxide, hydrate or solvate thereof:

(I)

wherein $Y^1$ is a bond, —(C=O)—, —S(O$_2$)—, —C(=O)O—, —OC(=O)—, —(C=O)NR$_3$—, —NR$_3$(C=O)—, —S(O$_2$)NR$_3$—, —NR$_3$S(O$_2$)—, or —NR$_3$(C=O)NR$_5$—, wherein $R_3$ and $R_5$ are independently hydrogen or optionally substituted ($C_1$-$C_6$)alkyl, $L^1$ is a divalent radical of formula -(Alk$^1$)$_m$(Q)$_n$(Alk$^2$)$_p$ wherein m, n and p are independently 0 or 1, Q is (i) an optionally substituted divalent mono- or bicyclic carbocyclic or heterocyclic radical having 5-13 ring members, or (ii), in the case where p is 0, a divalent radical of formula -Q$^1$-X$^2$— wherein X$^2$ is —O—, —S— or NR$^A$— wherein R$^A$ is hydrogen or optionally substituted $C_1$-$C_3$ alkyl, and Q$^1$ is an optionally substituted divalent mono- or bicyclic carbocyclic or heterocyclic radical having 5-13 ring members, Alk$^1$ and Alk$^2$ independently represent optionally substituted divalent $C_3$-$C_7$ cycloalkyl radicals, or optionally substituted straight or branched, $C_1$-$C_6$ alkylene, $C_2$-$C_6$ alkenylene, or $C_2$-$C_6$ alkynylene radicals which may optionally contain or terminate in an ether (—O—), thioether (—S—) or amino (—NR$^A$—) link wherein R$^A$ is hydrogen or optionally substituted $C_1$-$C_3$ alkyl;

z is 0 or 1;

A represents an optionally substituted mono-, bi— or tricyclic carbocyclic or heterocyclic ring system; and -[Linker]- represents a divalent linker radical linking a ring atom in A with the hydroxamic acid group —CONHOH, the length of the linker radical, from the terminal atom linked to the ring atom of A to the terminal atom linked to the hydroxamic acid group, is equivalent to that of an unbranched saturated hydrocarbon chain of from 2-10 carbon atoms; and R is a radical of formula (X) or (Y):

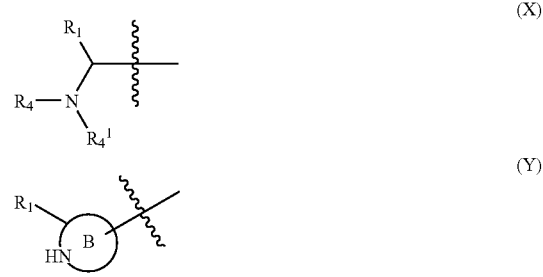

wherein $R_1$ is a carboxylic acid group (—COOH), or an ester group which is hydrolysable by one or more intracellular carboxylesterase enzymes to a carboxylic acid group;

$R_4$ is hydrogen; or optionally substituted $C_1$-$C_6$ alkyl, $C_3$-$C_7$ cycloalkyl, aryl, aryl($C_1$-$C_6$ alkyl)-, heteroaryl, heteroaryl($C_1$-$C_6$ alkyl)-, —(C=O)R$_3$, —(C=O)OR$_3$, or —(C=O)NR$_3$ wherein $R_3$ is hydrogen or optionally substituted ($C_1$-$C_6$)alkyl, $C_3$-$C_7$ cycloalkyl, aryl, aryl($C_1$-$C_6$ alkyl)-, heteroaryl, or heteroaryl($C_1$-$C_6$ alkyl)-;

$R_4^1$ is hydrogen or optionally substituted $C_1$-$C_6$ alkyl; and

B is a monocyclic heterocyclic ring of 5 or 6 ring atoms wherein $R_1$ is linked to a ring carbon adjacent the ring nitrogen shown, and ring B is optionally fused to a second carbocyclic or heterocyclic ring of 5 or 6 ring atoms in which case the bond shown intersected by a wavy line may be from a ring atom in said second ring;

Although the above definition potentially includes molecules of high molecular weight, it is preferable, in line with general principles of medicinal chemistry practice, that the compounds with which this invention is concerned should have molecular weights of no more than 600.

In another broad aspect the invention provides the use of a compound of formula (I) as defined above, or an N-oxide, salt, hydrate or solvate thereof in the preparation of a composition for inhibiting the activity of an HDAC enzyme.

The compounds with which the invention is concerned may be used for the inhibition of HDAC activity, particularly HDAC1 activity, ex vivo or in vivo.

In one aspect of the invention, the compounds of the invention may be used in the preparation of a composition for the treatment of cell-proliferation disease, for example cancer cell proliferation, polyglutamine diseases for example Huntingdon disease, neurodegenerative diseases for example Alzheimer disease, autoimmune disease for example rheumatoid arthritis, and organ transplant rejection, diabetes, haematological disorders, infection (including but not limited to protozoal and fungal), inflammatory disease, and cardiovascular disease, including atherosclerosis.

In another aspect, the invention provides a method for the treatment of the foregoing disease types, which comprises administering to a subject suffering such disease an effective amount of a compound of formula (I) as defined above.

The term "ester" or "esterified carboxyl group" means a group $R_9$O(C=O)— in which $R_9$ is the group characterising the ester, notionally derived from the alcohol $R_9$OH.

As used herein, the term "($C_a$-$C_b$)alkyl" wherein a and b are integers refers to a straight or branched chain alkyl radical having from a to b carbon atoms. Thus when a is 1 and b is 6, for example, the term includes methyl, ethyl, n-propyl, iso-propyl, n-butyl, isobutyl, sec-butyl, t-butyl, n-pentyl and n-hexyl.

As used herein the term "divalent ($C_a$-$C_b$)alkylene radical" wherein a and b are integers refers to a saturated hydrocarbon chain having from a to b carbon atoms and two unsatisfied valences.

As used herein the term "($C_a$-$C_b$)alkenyl" wherein a and b are integers refers to a straight or branched chain alkenyl moiety having from a to b carbon atoms having at least one double bond of either E or Z stereochemistry where applicable. The term includes, for example, vinyl, allyl, 1- and 2-butenyl and 2-methyl-2-propenyl.

As used herein the term "divalent ($C_a$-$C_b$)alkenylene radical" means a hydrocarbon chain having from a to b carbon atoms, at least one double bond, and two unsatisfied valences.

As used herein the term "$C_a$-$C_b$ alkynyl" wherein a and b are integers refers to straight chain or branched chain hydrocarbon groups having from two to six carbon atoms and having in addition one triple bond. This term would include for example, ethynyl, 1-propynyl, 1- and 2-butynyl, 2-methyl-2-propynyl, 2-pentynyl, 3-pentynyl, 4-pentynyl, 2-hexynyl, 3-hexynyl, 4-hexynyl and 5-hexynyl.

As used herein the term "divalent ($C_a$-$C_b$)alkynylene radical" wherein a and b are integers refers to a divalent hydrocarbon chain having from 2 to 6 carbon atoms, and at least one triple bond.

As used herein the term "carbocyclic" refers to a mono-, bi- or tricyclic radical having up to 16 ring atoms, all of which are carbon, and includes aryl and cycloalkyl.

As used herein the term "cycloalkyl" refers to a monocyclic saturated carbocyclic radical having from 3-8 carbon atoms and includes, for example, cyclopropyl, cyclobutyl, cyclopentyl, cyclohexyl, cycloheptyl and cyclooctyl.

As used herein the unqualified term "aryl" refers to a mono-, bi- or tri-cyclic carbocyclic aromatic radical, and includes radicals having two monocyclic carbocyclic aromatic rings which are directly linked by a covalent bond. Illustrative of such radicals are phenyl, biphenyl and napthyl.

As used herein the unqualified term "heteroaryl" refers to a mono-, bi- or tri-cyclic aromatic radical containing one or more heteroatoms selected from S, N and O, and includes radicals having two such monocyclic rings, or one such monocyclic ring and one monocyclic aryl ring, which are directly linked by a covalent bond. Illustrative of such radicals are thienyl, benzthienyl, furyl, benzfuryl, pyrrolyl, imidazolyl, benzimidazolyl, thiazolyl, benzthiazolyl, isothiazolyl, benzisothiazolyl, pyrazolyl, oxazolyl, benzoxazolyl, isoxazolyl, benzisoxazolyl, isothiazolyl, triazolyl, benztriazolyl, thiadiazolyl, oxadiazolyl, pyridinyl, pyridazinyl, pyrimidinyl, pyrazinyl, triazinyl, indolyl and indazolyl.

As used herein the unqualified term "heterocyclyl" or "heterocyclic" includes "heteroaryl" as defined above, and in its non-aromatic meaning relates to a mono-, bi— or tri-cyclic non-aromatic radical containing one or more heteroatoms selected from S, N and O, and to groups consisting of a monocyclic non-aromatic radical containing one or more such heteroatoms which is covalently linked to another such radical or to a monocyclic carbocyclic radical. Illustrative of such radicals are pyrrolyl, furanyl, thienyl, piperidinyl, imidazolyl, oxazolyl, isoxazolyl, thiazolyl, thiadiazolyl, pyrazolyl, pyridinyl, pyrrolidinyl, pyrimidinyl, morpholinyl, piperazinyl, indolyl, morpholinyl, benzfuranyl, pyranyl, isoxazolyl, benzimidazolyl, methylenedioxyphenyl, ethylenedioxyphenyl, maleimido and succinimido groups.

Unless otherwise specified in the context in which it occurs, the term "substituted" as applied to any moiety herein means substituted with up to four compatible substituents, each of which independently may be, for example, ($C_1$-$C_6$) alkyl, ($C_1$-$C_6$)alkoxy, hydroxy, hydroxy($C_1$-$C_6$)alkyl, mercapto, mercapto($C_1$-$C_6$)alkyl, ($C_1$-$C_6$)alkylthio, phenyl, halo (including fluoro, bromo and chloro), trifluoromethyl, trifluoromethoxy, nitro, nitrile (—CN), oxo, —COOH, —COOR$^A$, —COR$^A$, —SO$_2$R$^A$, —CONH$_2$, —SO$_2$NH$_2$, —CONHR$^A$, —SO$_2$NHR$^A$, —CONR$^A$R$^B$, —SO$_2$NR$^A$R$^B$, —NH$_2$, —NHR$^A$, —NR$^A$R$^B$, —OCONH$_2$, —OCONHR$^A$, —OCONR$^A$R$^B$, —NHCOR$^A$, —NHCOOR$^A$, —NR$^B$COOR$^A$, —NHSO$_2$OR$^A$, —NR$^B$SO$_2$OH, —NR$^B$SO$_2$OR$^A$, —NHCONH$_2$, —NR$^A$CONH$_2$, —NHCONHR$^B$, —NR$^A$CONHR$^B$, —NHCONR$^A$R$^B$ or —NR$^A$CONR$^A$R$^B$ wherein R$^A$ and R$^B$ are independently a ($C_1$-$C_6$)alkyl, ($C_3$-$C_6$) cycloalkyl, phenyl or monocyclic heteroaryl having 5 or 6 ring atoms. An "optional substituent" may be one of the foregoing substituent groups.

As used herein the term "salt" includes base addition, acid addition and quaternary salts. Compounds of the invention which are acidic can form salts, including pharmaceutically acceptable salts, with bases such as alkali metal hydroxides, e.g. sodium and potassium hydroxides; alkaline earth metal hydroxides e.g. calcium, barium and magnesium hydroxides; with organic bases e.g. N-methyl-D-glucamine, choline tris (hydroxymethyl)amino-methane, L-arginine, L-lysine, N-ethyl piperidine, dibenzylamine and the like. Those compounds (I) which are basic can form salts, including pharmaceutically acceptable salts with inorganic acids, e.g. with hydrohalic acids such as hydrochloric or hydrobromic acids, sulphuric acid, nitric acid or phosphoric acid and the like, and with organic acids e.g. with acetic, tartaric, succinic, fumaric, maleic, malic, salicylic, citric, methanesulphonic, p-toluenesulphonic, benzoic, benzenesunfonic, glutamic, lactic, and mandelic acids and the like.

Compounds of the invention which contain one or more actual or potential chiral centres, because of the presence of asymmetric carbon atoms, can exist as a number of diastereoisomers with R or S stereochemistry at each chiral centre. The invention includes all such diastereoisomers and mixtures thereof.

As stated above, the esters of the invention are primarily prodrugs of the corresponding carboxylic acids to which they are converted by intracellular carboxylesterases. However, for so long as they remain unhydrolised, the esters may have HDAC inhibitory activity in their own right. The compounds of the invention include not only the ester, but also the corresponding carboxylic acid hydrolysis products.

The Hydroxamate Group —C(=O)NHOH

In the compounds of the invention, the hydroxamate group functions as a metal binding group, interacting with the metal ion at the active site of the HDAC enzyme, which lies at the base of a pocket in the folded enzyme structure.

The Ring or Ring System A

Ring or ring system A is a mono- bi- or tri-cyclic carbocyclic or heterocyclic ring system, optionally substituted. In the compounds of the invention, when bound to the HDAC enzyme's active site, ring or ring system A lies within or at the entrance to the pocket containing the metal ion, with the -[Linker]- radical extending deeper into that pocket linking A to the metal binding hydroxamic acid group. In the art, the ring or ring system A is sometimes informally referred to as the "head group" of the inhibitor. Examples of ring systems A include the following:

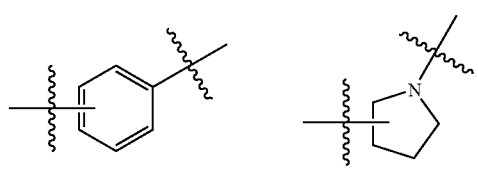

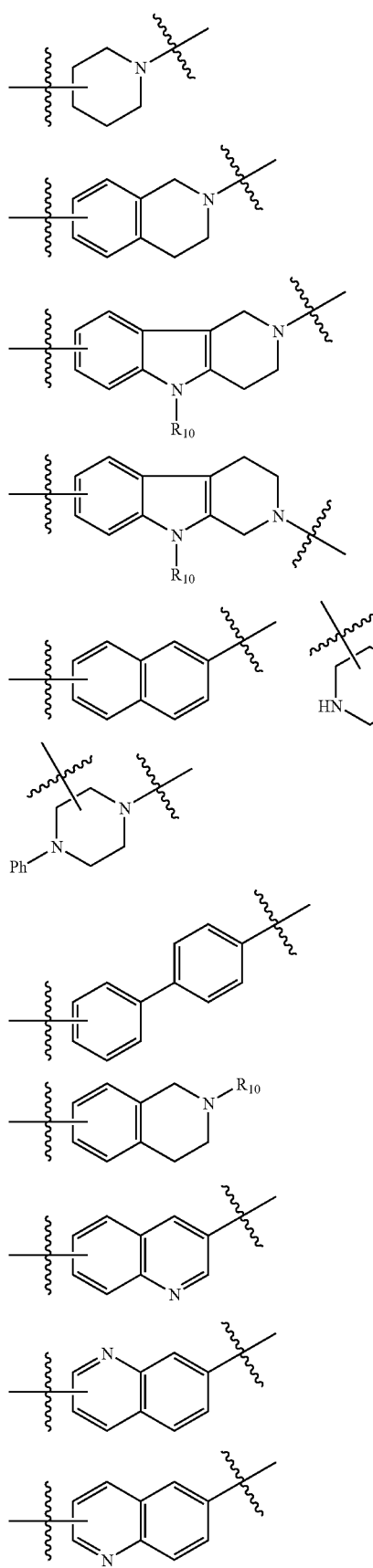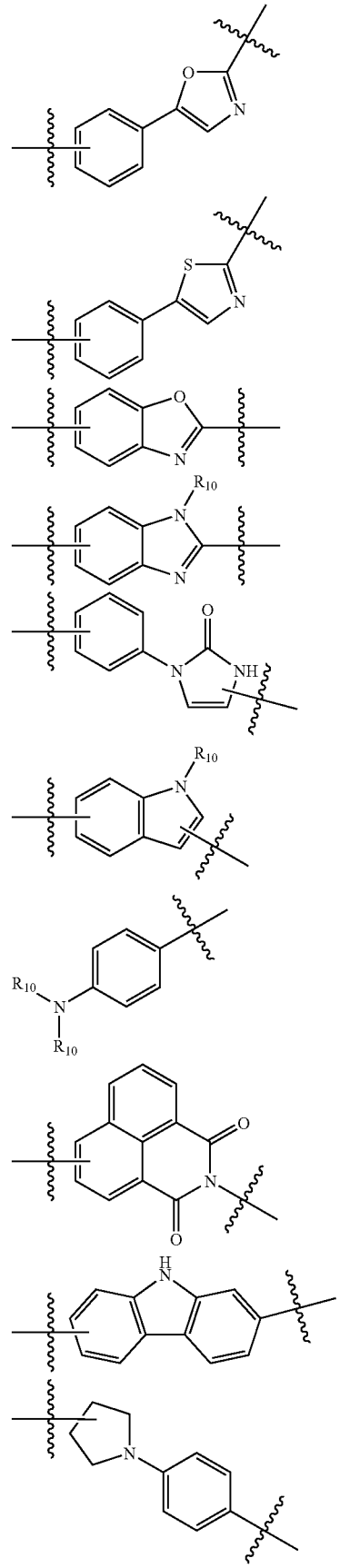

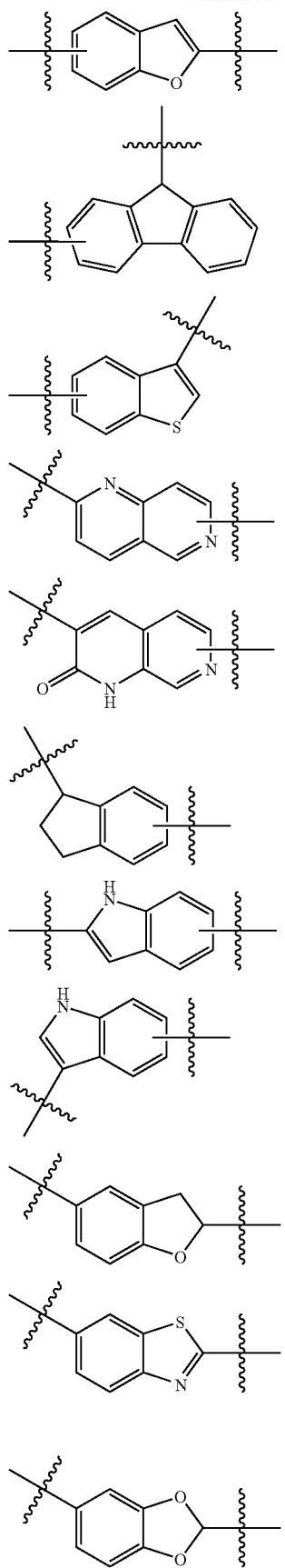
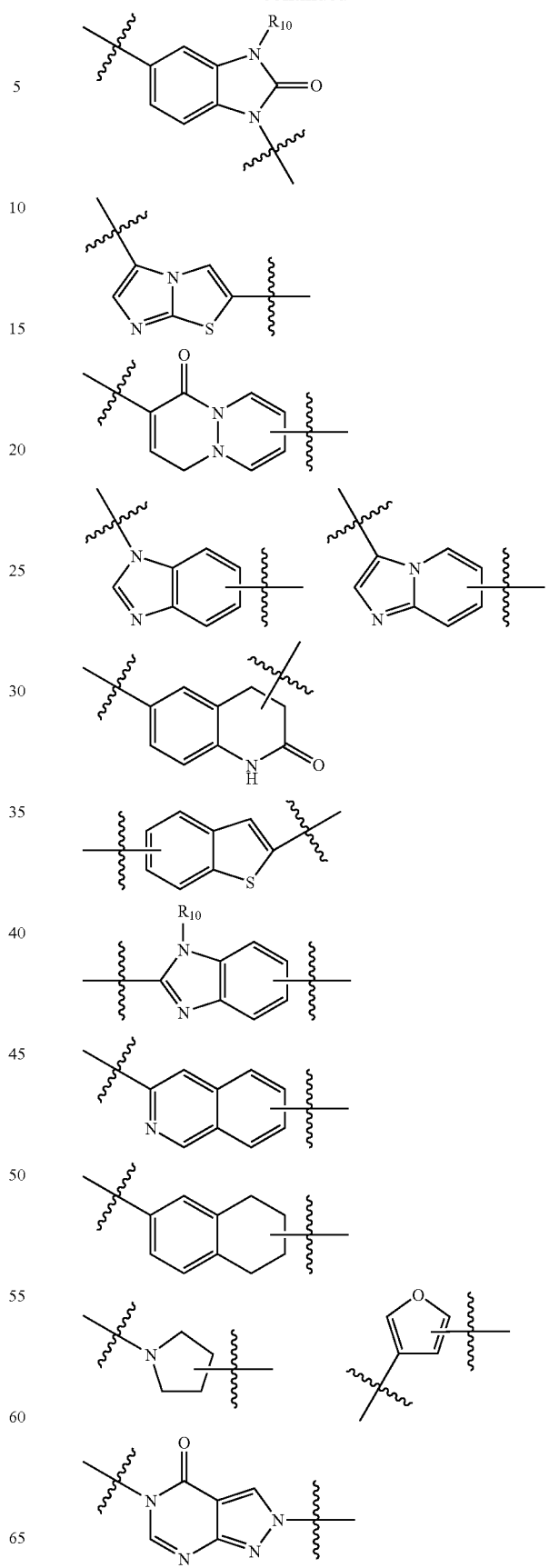

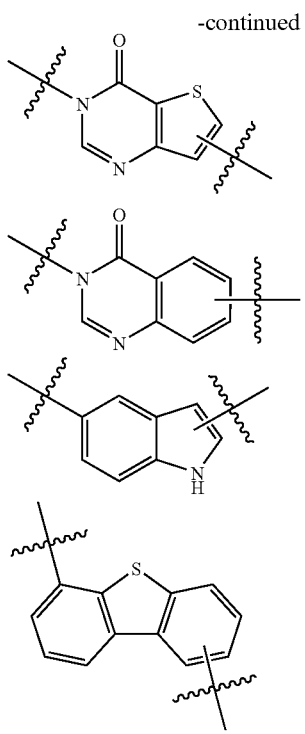

wherein $R_{10}$ is hydrogen or optionally substituted $C_1$-$C_6$ alkyl, the bond intersected by the wavy line connects to the Linker radical in the compounds (I), and wherein the grouping $RL^1Y^1[CH_2]_z$ in the compounds (I) is linked to any convenient ring atom of the ring system shown.

The -[Linker]- Radical

-[Linker]- represents a divalent linker radical linking a ring atom in A with the hydroxamic acid group CONHOH, the length of the linker radical, from the terminal atom linked to the ring atom of A to the terminal atom linked to the hydroxamic acid group, being equivalent to that of an unbranched saturated hydrocarbon chain of from 2-10 carbon atoms. An unbranched saturated hydrocarbon chain of 2 carbon atoms has a length of about 1.5 angstroms, and one of 10 carbon atoms has a length of about 11.3 angstroms. The length of any given -[Linker]- radical can be determined from data on atom radii and bond lengths in the literature, or can be determined using chemical structure modelling software such as DS ViewerPro (Accelrys, Inc). The defined length of the -[Linker]- radical reflects the fact that the head group A may lie at the entrance to, or within, the metal ion-containing pocket at the active site of the enzyme, and is therefore loosely related to the depth of that pocket. In many cases, the length of the linker will be equivalent to that of an unbranched saturated hydrocarbon chain of from 4 to 9 carbon atoms, for example 5, 6 or 7 carbon atoms. Specific general types of -[Linker]- radical are those discussed below as "Type 1", "Type 2", and "Type 3" linkers.

Type 1 Linkers

In this type, -[Linker]- represents a divalent radical of formula —$(CH_2)_x$—Z-$L^2$- wherein x is 0 or 1;

Z is a bond, —$NR_3$—, —$NR_3C(=O)$—, —$C(=O)NR_3$—, —$NR_4C(=O)$—$NR_3$—, —$C(=S)$—$NR_3$, —$C(=N)$—$NR_3$—$NR_3S(=O)_2$—, or —$S(=O)_2NR_3$— wherein $R_3$ is hydrogen or $C_1$-$C_6$ alkyl; —$C(=O)$; or —$S(=O)_2$—; and $L^2$ represents an optionally substituted, straight or branched, $C_3$-$C_7$ alkylene, $C_2$-$C_6$ alkenylene or $C_2$-$C_6$ alkynylene radicals which may optionally contain or terminate in an ether (—O—), thioether (—S—) or amino (—$NR^A$—) link wherein $R^A$ is hydrogen or optionally substituted $C_1$-$C_3$ alkyl.

In one sub-class of this type of linker, in any compatible combination, x is 0; Z is —C(=O)—, —NHC(=O)— or —(=O)NH— and $L^2$ is —$(CH_2)_5$—, —$(CH_2)_6$—, or —$(CH_2)_7$—.

Type 2 Linkers

In this type, -[Linker]- represents a divalent radical of formula —$(CH_2)_x$-$L^3$-$Ar^1$-$L^4$- wherein x is 0 or 1;

$L^3$ is Z or $L^2$ or Z-$L^2$ wherein Z is as defined in relation to Type 1 linkers and $L^2$ is a bond or an optionally substituted divalent $C_1$-$C_3$ alkylene radical;

$Ar^1$ is a divalent phenyl radical or a divalent mono-, or bi-cyclic heteroaryl radical having 5 to 13 ring members, and $L^4$ is a bond or optionally substituted —$CH_2$— or —CH=CH—.

In one sub-class of this type of linker, in any compatible combination, x is 0 or 1; $L^3$ is Z or Z-$L^2$, wherein Z is —NH—, —NHS(=O)$_2$—, —S(=O)$_2$NH— or —S(=O)$_2$—; $L^2$ is —$CH_2$— $L^4$ is a bond or —$CH_2$—; and $Ar^1$ is divalent radical selected from the following:

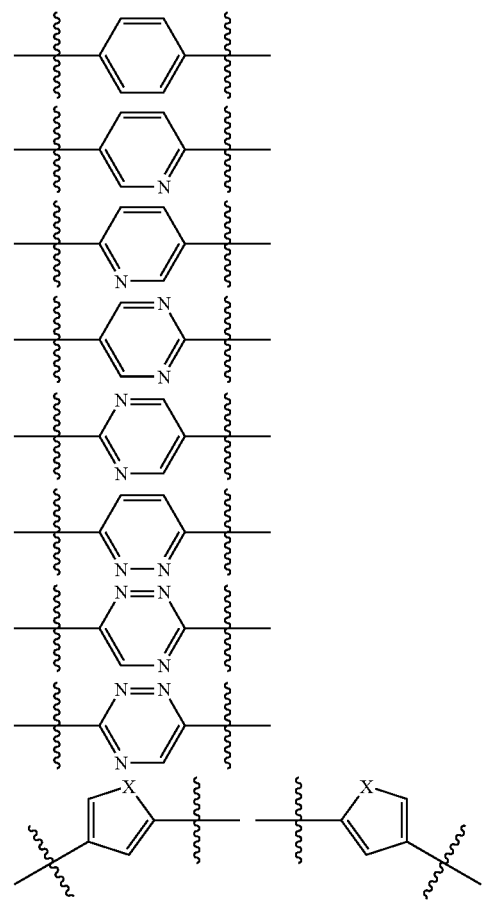

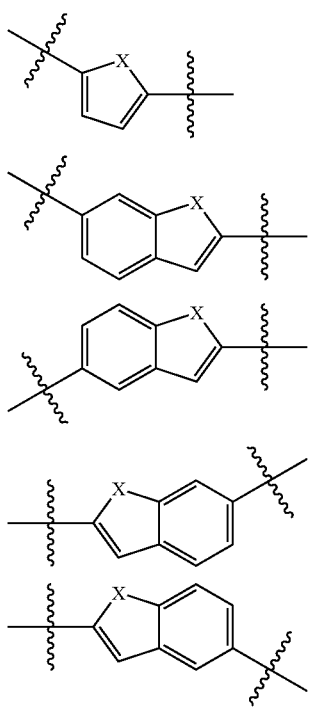

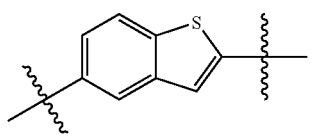

wherein X is O, S or NH.

Of the above Ar¹ radicals, the benzo[b]thiophen-6-yl radical

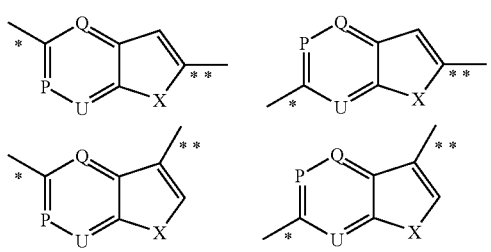

is a particular example.

In another sub-class of this type of linker, in any compatible combination, x is 0; $L^3$ is $L^2$, wherein $L^2$ is an straight chain $C_3$-$C_5$ alkylene radical which may optionally contain an ether (—O—), thioether (—S—) or amino (—$NR^A$—) link wherein $R^A$ is hydrogen or optionally substituted $C_1$-$C_3$ alkyl, for example hydroxyethyl; and Ar¹ is divalent radical selected from those listed in the preceding paragraph.

In yet another subclass of this type, x is 0, $L^3$ and $L^4$ are bonds, and Ar¹ is a divalent phenyl radical or a divalent bicyclic heteroaryl radical having 9 to 13 ring members, for example selected from the following:

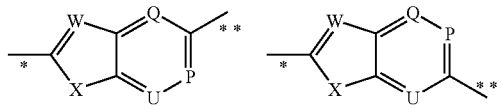

wherein X is selected from O, S and NH and P, Q, and U are independently selected from N and CH; and the bond marked ** is linked to the CONHOH group; and the bond marked * is linked to the ring or ring system A.

Type 3 Linkers

In this type, -[Linker]- represents a divalent radical of formula —$(CH_2)_x$-$L^3$-B—Ar¹-$L^4$- wherein x, Ar¹, $L^3$ and $L^4$ are as discussed with reference to Type 2 linkers above; and B is a mono- or bi-cyclic heterocyclic ring system.

In one subclass of this type of linker B is one of the following:

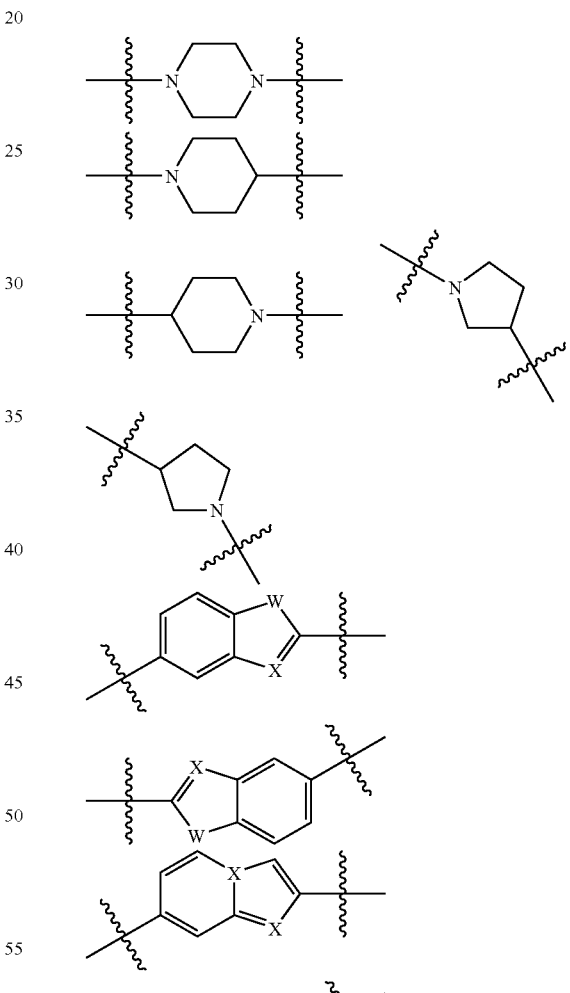

wherein X is N and W is NH, O or S.

The Ester Group $R_1$

The ester group $R_1$ must be one which in the compound of the invention is which is hydrolysable by one or more intracellular carboxylesterase enzymes to a carboxylic acid group.

Intracellular carboxylesterase enzymes capable of hydrolysing the ester group of a compound of the invention to the corresponding acid include the three known human enzyme isotypes hCE-1, hCE-2 and hCE-3. Although these are considered to be the main enzymes other enzymes such as biphenylhydrolase (BPH) may also have a role in hydrolysing the conjugates. In general, if the carboxylesterase hydrolyses the free amino acid ester to the parent acid it will, subject to the N-carbonyl dependence of hCE-2 and hCE-3 discussed below, also hydrolyse the ester motif when covalently conjugated to the modulator. Hence, the broken cell assay described herein provide a straightforward, quick and simple first screen for esters which have the required hydrolysis profile. Ester motifs selected in that way may then be re-assayed in the same carboxylesterase assay when conjugated to the HDAC inhibitor via the chosen conjugation chemistry, to confirm that it is still a carboxylesterase substrate in that background.

Subject to the requirement that they be hydroysable by intracellular carboxylesterase enzymes, examples of particular ester groups $R_1$ include those of formula —(C=O)$OR_9$ wherein $R_9$ is (i) $R_7R_8$CH— wherein $R_7$ is optionally substituted $(C_1-C_3)$alkyl-$(Z^1)_a$—$(C_1-C_3)$alkyl- or $(C_2-C_3)$alkenyl-$(Z^1)_a$—$(C_1-C_3)$alkyl- wherein a is 0 or 1 and $Z^1$ is —O—, —S—, or —NH—, and $R_8$ is hydrogen or $(C_1-C_3)$alkyl- or $R_7$ and $R_8$ taken together with the carbon to which they are attached form an optionally substituted $C_3-C_7$ cycloalkyl ring or an optionally substituted heterocyclic ring of 5- or 6-ring atoms; or (ii) optionally substituted phenyl or monocyclic heterocyclic having 5 or 6 ring atoms. Within these classes, $R_9$ may be, for example, methyl, ethyl, n- or iso-propyl, n- or sec-butyl, cyclohexyl, allyl, phenyl, benzyl, 2-, 3- or 4-pyridylmethyl, N-methylpiperidin-4-yl, tetrahydrofuran-3-yl or methoxyethyl. Currently preferred is where $R_9$ is cyclopentyl.

Macrophages are known to play a key role in inflammatory disorders through the release of cytokines in particular TNFα and IL-1 (van Roon et al Arthritis and Rheumatism, 2003, 1229-1238). In rheumatoid arthritis they are major contributors to the maintenance of joint inflammation and joint destruction. Macrophages are also involved in tumour growth and development (Naldini and Carraro Curr Drug Targets Inflamm Allergy, 2005, 3-8). Hence agents that selectively target macrophage cell proliferation could be of value in the treatment of cancer and autoimmune disease. Targeting specific cell types would be expected to lead to reduced side-effects. The inventors have discovered a method of targeting HDAC inhibitors to macrophages which is based on the observation that the way in which the esterase motif is linked to the HDAC inhibitor determines whether it is hydrolysed, and hence whether or not it accumulates in different cell types. Specifically it has been found that macrophages contain the human carboxylesterase HCE-1 whereas other cell types do not. In the general formula (I) when the nitrogen of the esterase motif is substituted but not directly bonded to a carbonyl group the ester will only be hydrolysed by HCE-1 and hence the HDAC inhibitors will only accumulate in macrophages. Herein, unless "monocyte" or "monocytes" is specified, the term macrophage or macrophages will be used to denote macrophages (including tumour associated macrophages) and/or monocytes.

The Group $R_4$

The group $R_4$ is present in the compounds of the invention when R in formula (I) is a radical of formula (X)

As mentioned above, if the modulator is intended to act only in cell types where hCE-1 is present, such as macrophages, the amino group of the carboxylesterase motif should be directly linked to a group other than carbonyl. In such cases $R_4$ may be optionally substituted $C_1-C_6$ alkyl, $C_3-C_7$ cycloalkyl, aryl or heteroaryl, for example methyl, ethyl, n- or isopropyl, cyclopropyl, cyclopentyl, cyclohexyl, phenyl, or pyridyl. In cases where macrophage specificity is not required, $R_4$ may be hydrogen or —(C=O)$R_3$, wherein $R_3$ is optionally substituted $C_1-C_6$ alkyl such as methyl, ethyl, n- or isopropyl, or n-, iso- or sec-butyl, $C_3-C_7$ cycloalkyl such as cyclopropyl, cyclopentyl, cyclohexyl, phenyl, pyridyl, thienyl, phenyl($C_1-C_6$ alkyl)-, thienyl($C_1-C_6$ alkyl)- or pyridyl ($C_1-C_6$ alkyl)- such as benzyl, 4-methoxyphenylmethylcarbonyl, thienylmethyl or pyridylmethyl.

$R_4$ may also be, for example —(C=O)$OR_3$, or —(C=O)$NHR_3$ wherein $R_3$ is hydrogen or optionally substituted $(C_1-C_6)$alkyl such as methyl, ethyl, or n- or isopropyl.

In general, $R_4^1$ may be, for example, hydrogen, methyl, ethyl, n- or isopropyl. Where macrophage selectivity is required, the following combinations of $R_4$ and $R_4^1$ are suitable: ether $R_4$ or $R_4^1$ is alkyl.

Of course, $R_4$ and $R_4^1$ may independently be hydrogen, and in one subset of the compounds of the invention both are hydrogen.

For compounds of the invention which are to be administered systemically, esters with a slow rate of esterase cleavage are preferred, since they are less susceptible to pre-systemic metabolism. Their ability to reach their target tissue intact is therefore increased, and the ester can be converted inside the cells of the target tissue into the acid product. However, for local administration, where the ester is either directly applied to the target tissue or directed there by, for example, inhalation, it will often be desirable that the ester has a rapid rate of esterase cleavage, to minimise systemic exposure and consequent unwanted side effects. If a carbon atom to which the group R is attached is unsubstituted, ie R is attached to a methylene (—CH$_2$)— radical, then the esters tend to be cleaved more rapidly than if that carbon is substituted, or is part of a ring system such as a phenyl or cyclohexyl ring.

The Ring or Ring System B

Ring or ring system B is present in the compounds of the invention when R is a radical of formula (Y) above In such cases, the ring or ring system B is preferably one chosen from the following:

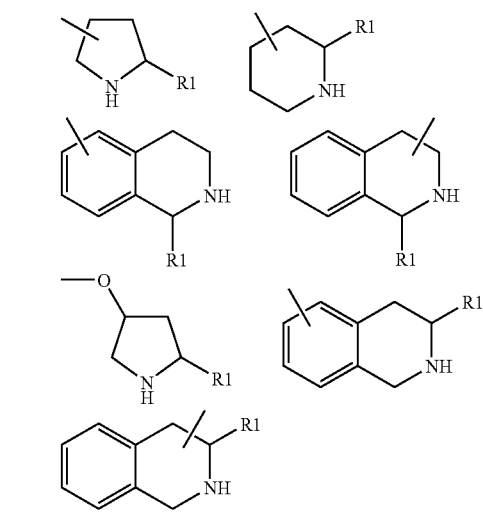

The Radical -$L^1$-$Y^1$—[CH$_2$]$_z$—

This radical (or bond) arises from the particular chemistry strategy chosen to link the amino acid ester motif R to the head group A of the inhibitor. Clearly the chemistry strategy for that coupling may vary widely, and thus many combinations of the variables $Y^1$, $L^1$, and z are possible. However, as mentioned above, when the inhibitor is bound to the HDAC enzyme at its active site, the head group A is located at the top of, or within, the metal-ion-containing pocket of the enzyme, so by linking the amino acid ester motif to the head group it generally extends in a direction away from that pocket, and thus minimises or avoids interference with the binding mode of the inhibitor template A-[Linker]-CONHOH. Hence the precise combination of variable making up the linking chemistry between the amino acid ester motif and the head group A will often be irrelevant to the primary binding mode of the compound as a whole. On the other hand, that linkage chemistry may in some cases pick up additional binding interactions with the enzyme at the top of, or adjacent to, the metal ion-containing pocket, thereby enhancing binding.

With the foregoing general observations in mind, taking the variables making up the radical -$L^1$-$Y^1$—$[CH_2]_z$— in turn:

z may be 0 or 1, so that a methylene radical linked to the head group A is optional;

$Y^1$ is may be, for example, —$NR_3$—, —S—, —O—, —C(=O)$NR_3$—, —$NR_3$C(=O)—, or —C(=O)O—, wherein $R_3$ is hydrogen or optionally substituted $C_1$-$C_6$ alkyl such as —$CH_2CH_2OH$;

In the radical $L^1$, examples of $Alk^1$ and $Alk^2$ radicals, when present, include —$CH_2$—, —$CH_2CH_2$— —$CH_2CH_2CH_2$—, —$CH_2CH_2CH_2CH_2$—, —CH=CH—, —CH=CHCH_2—, —CH_2CH=CH—, CH_2CH=CHCH_2—, —C≡C—, —C≡CCH_2—, CH_2C≡C—, and CH_2C=CCH_2. Additional examples of $Alk^1$ and $Alk^2$ include —$CH_2W$—, —$CH_2CH_2W$— —$CH_2CH_2WCH_2$—, —$CH_2CH_2WCH(CH_3)$—, —$CH_2WCH_2CH_2$—, —$CH_2WCH_2CH_2WCH_2$—, and —$WCH_2CH_2$— where W is —, —S—, —NH—, —N(CH_3)—, or —CH_2CH_2N(CH_2CH_2OH)CH_2—. Further examples of $Alk^1$ and $Alk^2$ include divalent cyclopropyl, cyclopentyl and cyclohexyl radicals.

In $L^1$, when n is 0, the radical is a hydrocarbon chain (optionally substituted and perhaps having an ether, thioether or amino linkage). Presently it is preferred that there be no optional substituents in $L^1$. When both m and p are 0, $L^1$ is a divalent mono- or bicyclic carbocyclic or heterocyclic radical with 5-13 ring atoms (optionally substituted). When n is 1 and at least one of m and p is 1, $L^1$ is a divalent radical including a hydrocarbon chain or chains and a mono- or bicyclic carbocyclic or heterocyclic radical with 5-13 ring atoms (optionally substituted). When present, Q may be, for example, a divalent phenyl, naphthyl, cyclopropyl, cyclopentyl, or cyclohexyl radical, or a mono-, or bi-cyclic heterocyclic radical having 5 to 13 ring members, such as piperidinyl, piperazinyl, indolyl, pyridyl, thienyl, or pyrrolyl radical, but 1,4-phenylene is presently preferred.

Specifically, in some embodiments of the invention, $L^1$, m and p may be 0 with n being 1. In other embodiments, n and p may be 0 with m being 1. In further embodiments, m, n and p may be all 0. In still further embodiments m may be 0, n may be 1 with Q being a monocyclic heterocyclic radical, and p may be 0 or 1. $Alk^1$ and $Alk^2$, when present, may be selected from —$CH_2$—, —$CH_2CH_2$—, and —$CH_2CH_2CH_2$— and Q may be 1,4-phenylene.

Specific preferred examples of the radical -$L^1$-$Y^1$—$[CH_2]_z$— include
—$(CH_2)_3NH$—, —$CH_2C(=O)NH$—, —$CH_2CH_2C(=O)NH$—, —$CH_2C(O)O$—, —$CH_2S$—, —$CH_2CH_2C(O)O$—, —$(CH_2)_4NH$—, —$CH_2CH_2S$—, —$CH_2O$, —$CH_2CH_2O$—,

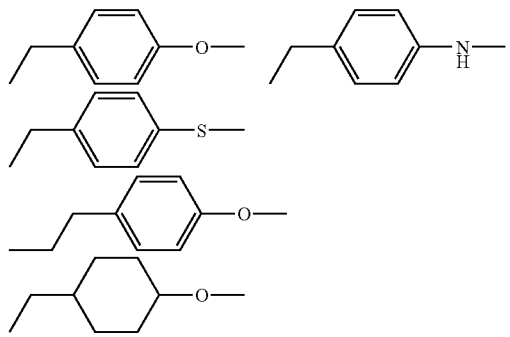

Examples of particular subsets of compounds of the invention include those of formulae (IA) to (IQ):

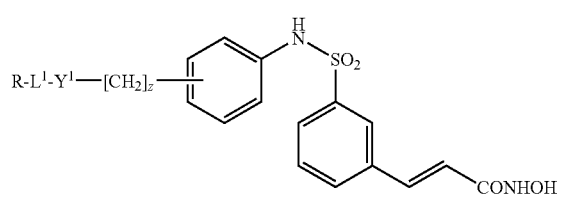

(IA)

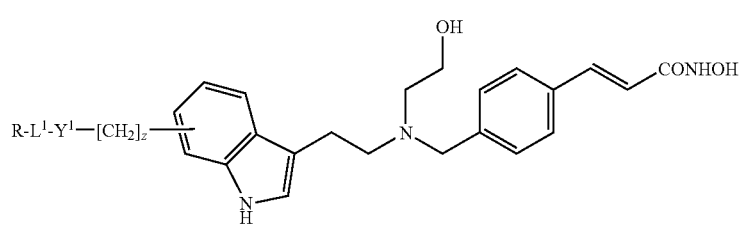

(IB)

-continued
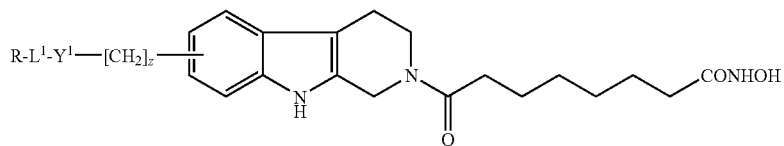
(IC)
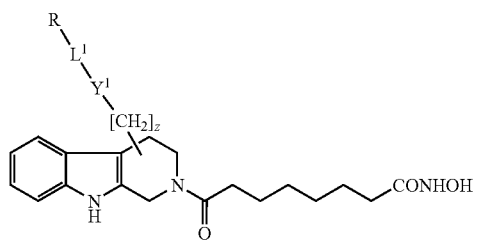
(ID)
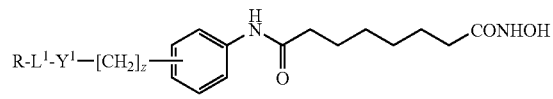
(IE)
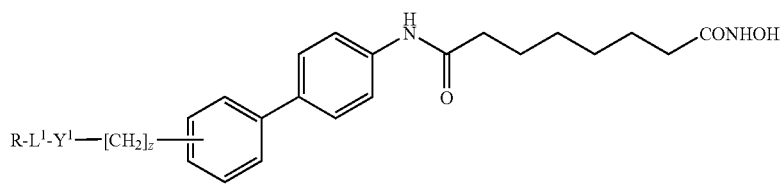
(IF)
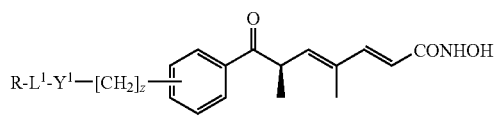
(IG)
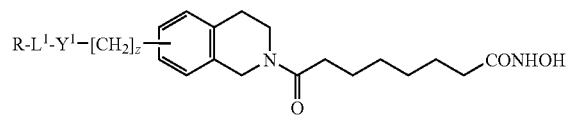
(IH)
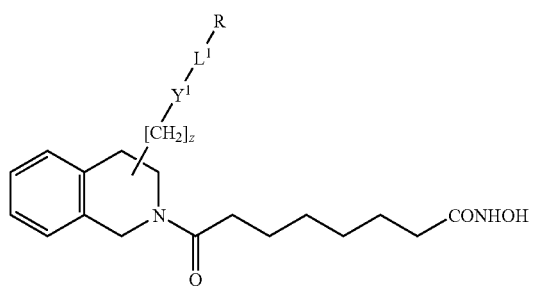
(IJ)
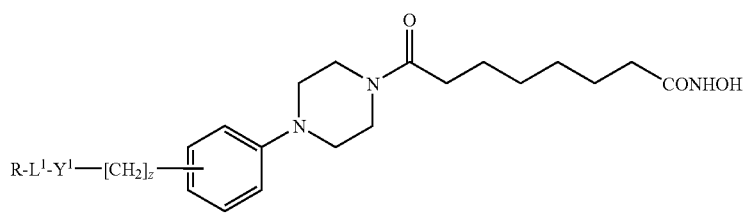
(IK)

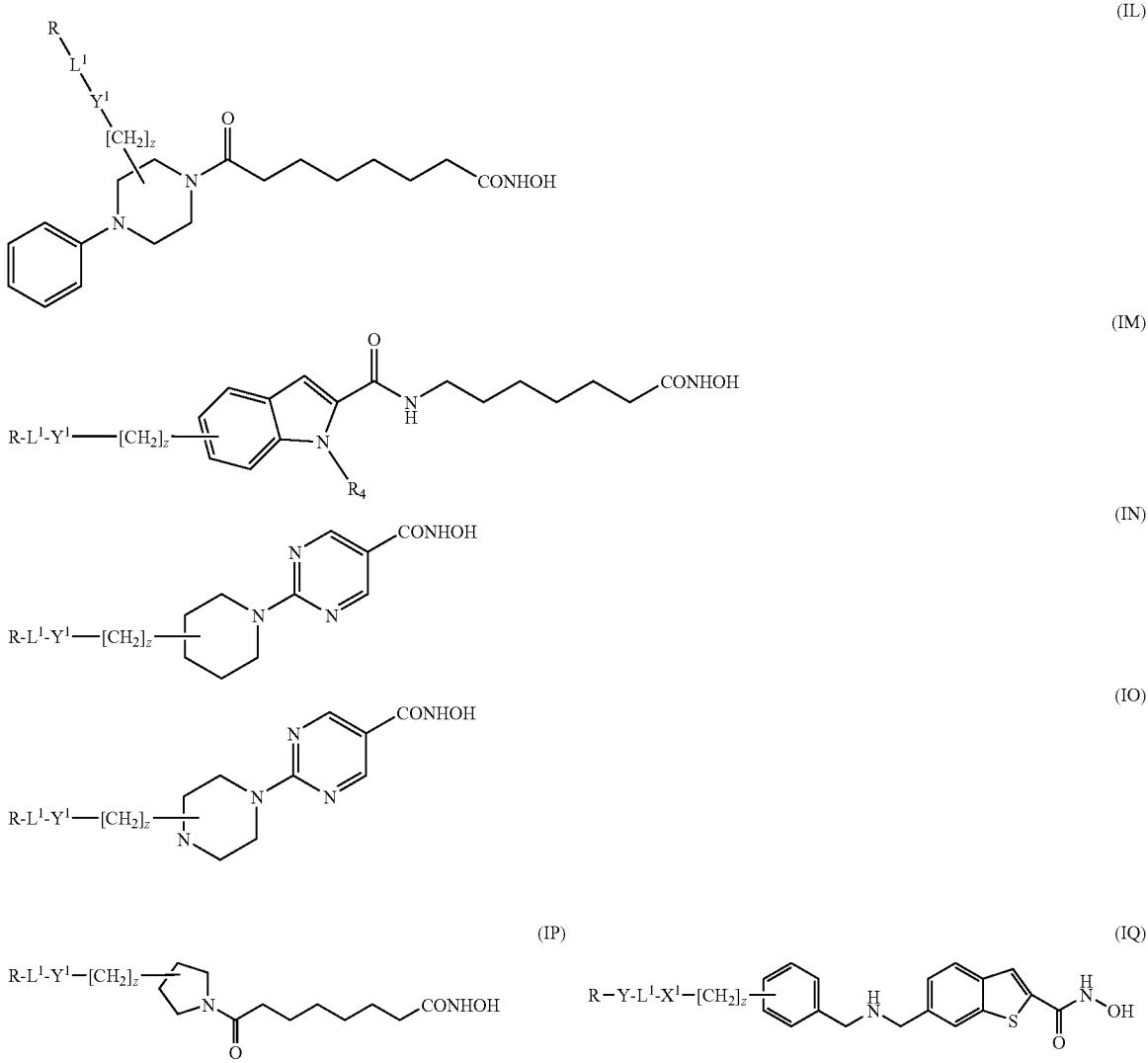

wherein z, R, $L^1$ and $Y^1$ are as defined in relation to formula (I), and as discussed above, including the preferences therefor.

Specific compounds of the invention include:

(S)-2-Amino-4-(4-{[(2-hydroxycarbamoyl-benzo[b]thiophen-6-ylmethyl)-amino]-methyl}-phenoxy)-butyric acid cyclopentyl ester (S)-2-Amino-5-(4-{[(2-hydroxycarbamoyl-benzo[b]thiophen-6-ylmethyl)-amino]-methyl}-phenoxy)-pentanoic acid cyclopentyl ester (R)-2-Amino-4-(4-{[(2-hydroxycarbamoyl-benzo[b]thiophen-6-ylmethyl)-amino]-methyl}-phenoxy)-butyric acid cyclopentyl ester (S)-2-Acetylamino-5-(4-{[(2-hydroxycarbamoyl-benzo[b]thiophen-6-ylmethyl)-amino]-methyl}-phenoxy)-pentanoic acid cyclopentyl ester (S)-Amino-[4-(4-{[(2-hydroxycarbamoyl-benzo[b]thiophen-6-ylmethyl)-amino]-methyl}-phenoxy)-phenyl]-acetic acid cyclopentyl ester (S)-2-Amino-3-[4-(4-{[(2-hydroxycarbamoyl-benzo[b]thiophen-6-ylmethyl)-amino]-methyl}-phenoxy)-phenyl]-propionic acid cyclopentyl ester and 2-(S)-Amino-3-[4-(4-{[(2-hydroxycarbamoyl-benzo[b]thiophen-6-ylmethyl)-amino]-methyl}-phenoxy)-cyclohexyl]-propionic acid cyclopentyl ester As mentioned above, the compounds with which the invention is concerned are inhibitors of HDAC enzyme activity, especially HDAC1 activity, ex vivo or in vivo.

It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing treatment. Optimum dose levels and frequency of dosing will be determined by clinical trial.

The compounds with which the invention is concerned may be prepared for administration by any route consistent with their pharmacokinetic properties. The orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application by inhalation, the drug may be formulated for aerosol delivery for example, by pressure-driven jet atomizers or ultrasonic atomizers, or preferably by propellant-driven metered aerosols or propellant-free administration of micronized powders, for example, inhalation capsules or other "dry powder" delivery systems. Excipients, such as, for example, propellants (e.g. Frigen in the case of metered aerosols), surface-active substances, emulsifiers, stabilizers, preservatives, flavorings, and fillers (e.g. lactose in the case of powder inhalers) may be present in such inhaled formulations. For the purposes of inhalation, a large number of apparata are available with which aerosols of optimum particle size can be generated and administered, using an inhalation technique which is appropriate for the patient. In addition to the use of adaptors (spacers, expanders) and pear-shaped containers (e.g. Nebulator®, Volumatic®), and automatic devices emitting a puffer spray (Autohaler®), for metered aerosols, in particular in the case of powder inhalers, a number of technical solutions are available (e.g. Diskhaler®, Rotadisk®, Turbohaler® or the inhalers for example as described in European Patent Application EP 0 505 321).

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

For topical application to the eye, the drug may be made up into a solution or suspension in a suitable sterile aqueous or non aqueous vehicle. Additives, for instance buffers such as sodium metabisulphite or disodium edeate; preservatives including bactericidal and fungicidal agents such as phenyl mercuric acetate or nitrate, benzalkonium chloride or chlorhexidine, and thickening agents such as hypromellose may also be included.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agent can be dissolved in the vehicle.

Compounds of the invention may be prepared, for example, by the methods described below and in the Examples herein.

Synthesis

There are multiple synthetic strategies for the synthesis of the compounds (I) with which the present invention is concerned, but all rely on known chemistry, known to the synthetic organic chemist. Thus, compounds according to formula (I) can be synthesised according to procedures described in the standard literature and are well-known to those skilled in the art. Typical literature sources are "Advanced Organic Chemistry", $4^{th}$ Edition (Wiley), J March, "Comprehensive Organic Transformation", $2^{nd}$ Edition (Wiley), R. C. Larock, "Handbook of Heterocyclic Chemistry", $2^{nd}$ Edition (Pergamon), A. R. Katritzky), review articles such as found in "Synthesis", "Acc. Chem. Res.", "Chem. Rev", or primary literature sources identified by standard literature searches online or from secondary sources such as "Chemical Abstracts" or "Beilstein".

For example, compounds of the invention may be prepared from the corresponding carboxylic acids (II)

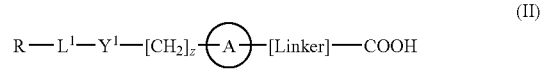

(II)

by reaction of an activated derivative thereof, such as the acid chloride, with hydroxylamine.

Alternatively, an N— or O-protected or N,O-diprotected precursor of the desired compound (I) may be deprotected. In a useful version of this method O-protection is provided by a resin support, from which the desired hydroxamic acid (I) may be cleaved, for example by acid hydrolysis.

Carboxyl protected derivatives of compounds (II), or O-linked resin-supported derivatives of compounds (II) of the invention may be synthesised in stages by literature methods, selected according to the particular structure of the desired compound. In that connection, the patent publications listed above provide information on the synthesis of HDAC inhibitors which are structurally similar to those of the present invention.

In one approach, suitable for compounds (I) wherein -[Linker]- represents a Type 1 divalent radical of formula —Z-$L^2$- wherein Z is —NHS(═O)$_2$— and $L^2$ is as defined and discussed above, an amine (III)

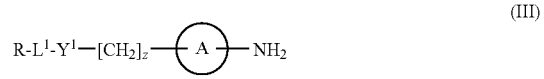

(III)

may be reacted with an activated derivative, for example the acid chloride, of a sulfonic acid HOSO$_2$-$L^2$-Z wherein Z is a protected carboxyl group, such as cleavable ester, or an O-linked resin-supported hydroxamic acid group.

In another approach, suitable for compounds (I) wherein -[Linker]- represents a Type 1 divalent radical of formula —Z-$L^2$- wherein Z is an amide radical —NHC(═O)—, an amine (III) may be reacted with an aldehyde HC(═O)-L-Z, Z being as defined in the preceding paragraph, in the presence of NaCNBH$_3$. Scheme A illustrates this route. (In the Scheme A and elsewhere herein, the symbol ● represents a solid phase resin support).

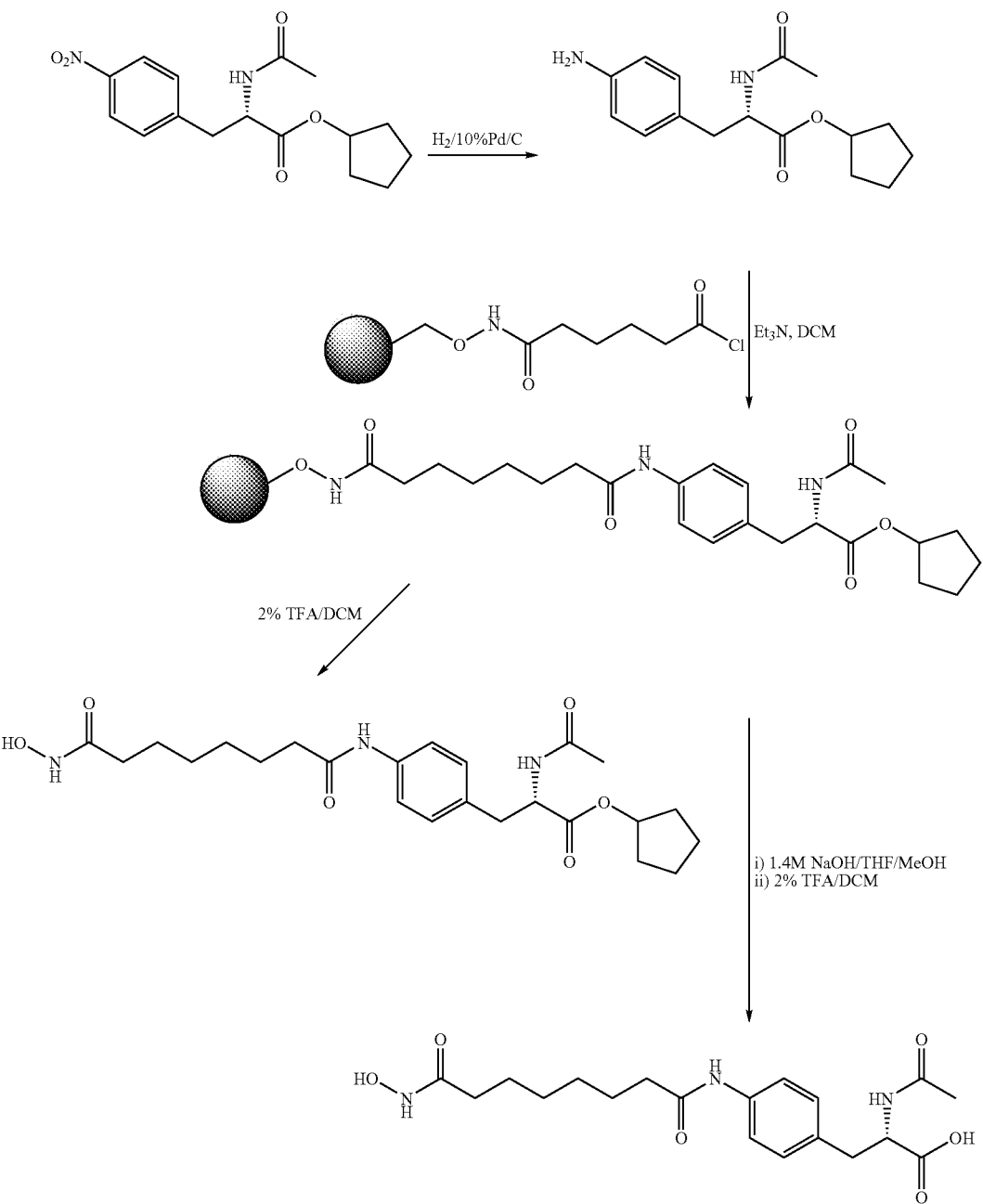
The 4-nitro phenyl derivative starting material of Scheme A may be prepared as in Scheme B:
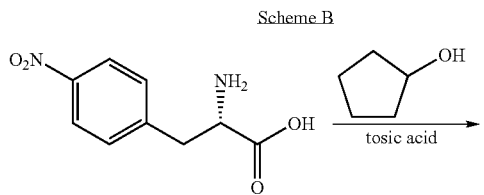
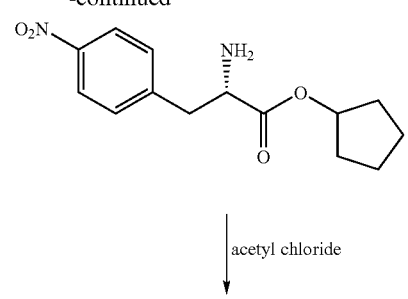

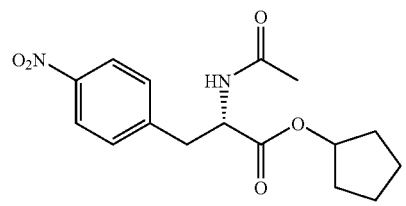

The case of compounds (I) where the ring or ring system A is linked to the -[Linker]-CONHOH moiety as a sulphonamide or amide formed at a ring nitrogen, the appropriate N-heterocycle (IV)

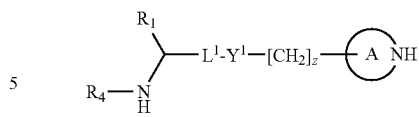

may be reacted with the corresponding carboxylic or sulfonic acid either as an activated derivative thereof such as the chloride, or in the presence of a carbodiimide coupling agent.

By way of further illustration of known literature chemistry which may be adapted for the synthesis of a variety of structural types of compounds of the invention, the following reaction schemes 1 to 10 are presented:

Scheme 1 uses a variety of substituted 2, 3 and 4-nitrobenzaldehyde starting materials, which can be accessed from the nitro-benzoic acid derivatives via reduction of the corresponding Weinreb amide.

Scheme 1

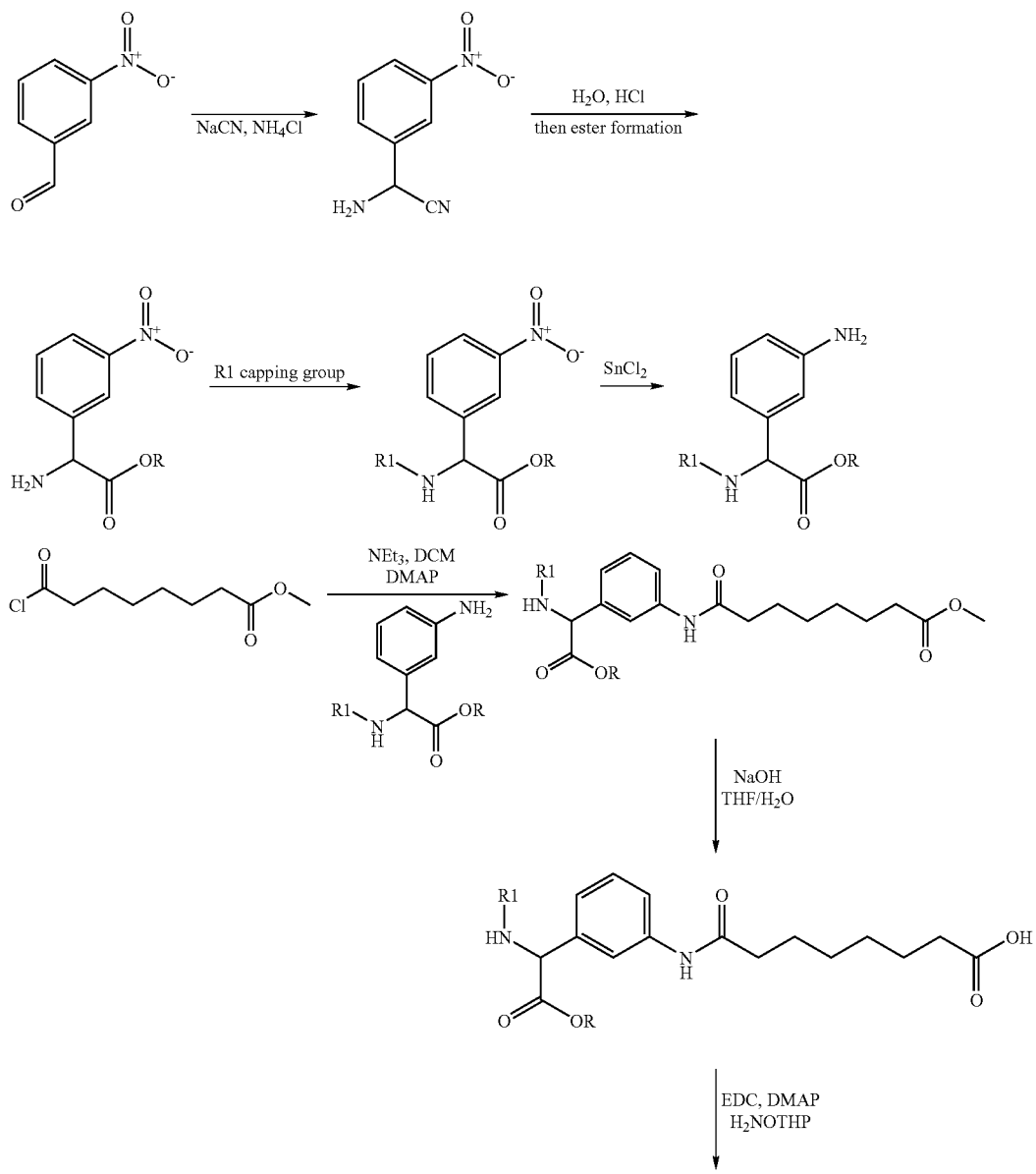

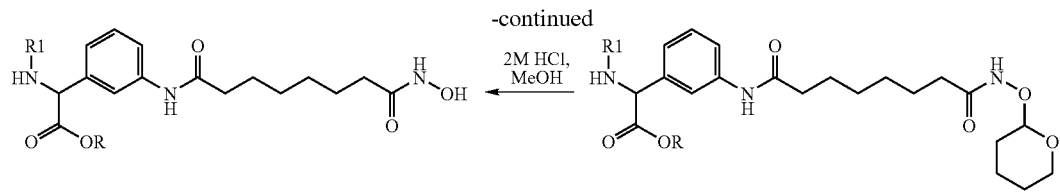

Scheme 2 illustrates a route to compounds of the invention which are 3-substituted β-carbolines, using N-Boc-D-tetrahydro-β-carboline-3-carboxylic acid (A). Treatment with TMSCl and methanol gives the protected carboxylic acid (as a methyl ester) with deprotection of the Boc protecting group. Reaction with the resin bound carboxylic acid intermediate followed by saponification, amide coupling with the amino acid ester and final resin cleavage gives the hydroxamic acid. The corresponding N-Boc-L-tetrahydro-β-carboline-3-carboxylic acid is also commercially available.

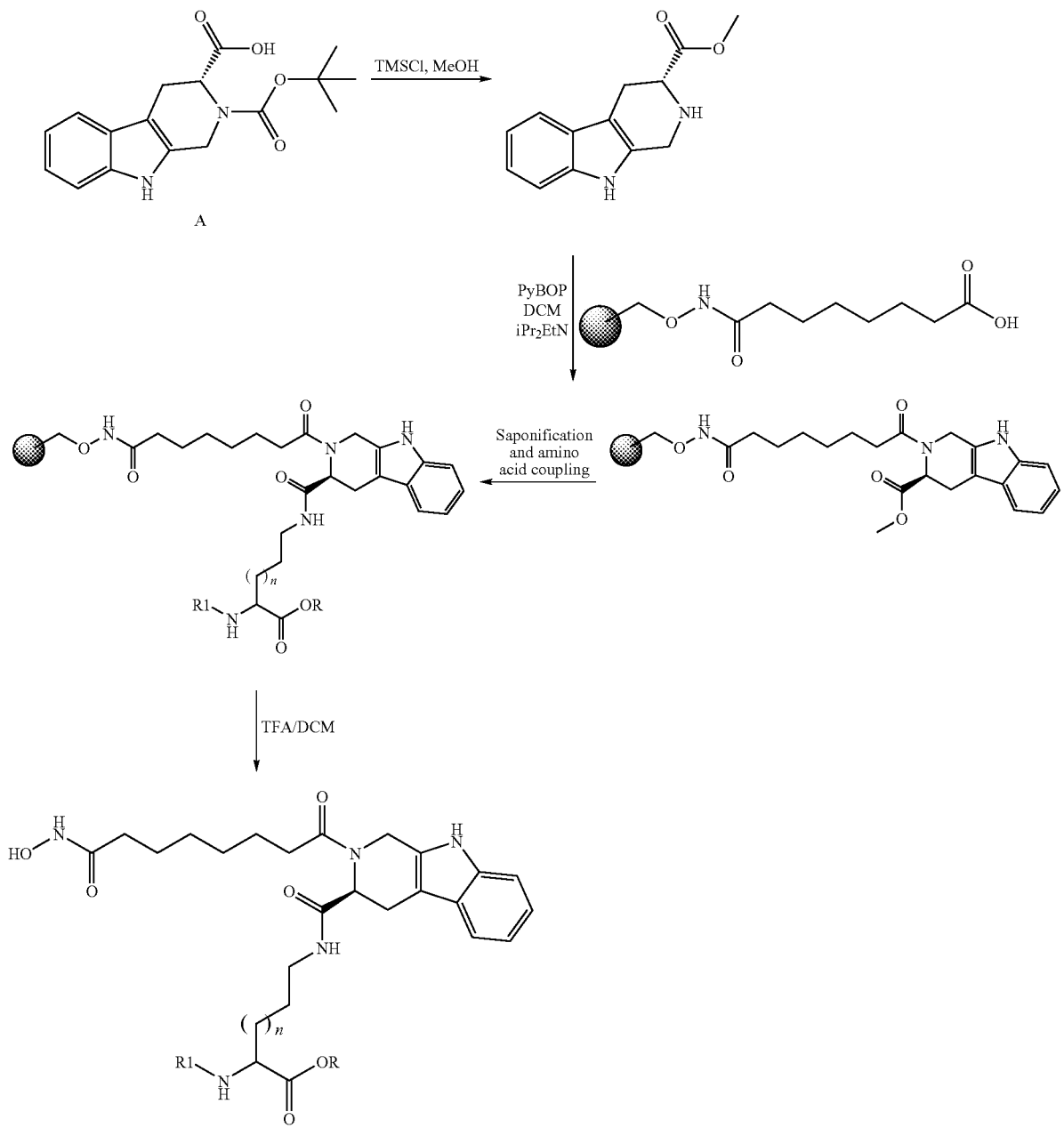

-continued
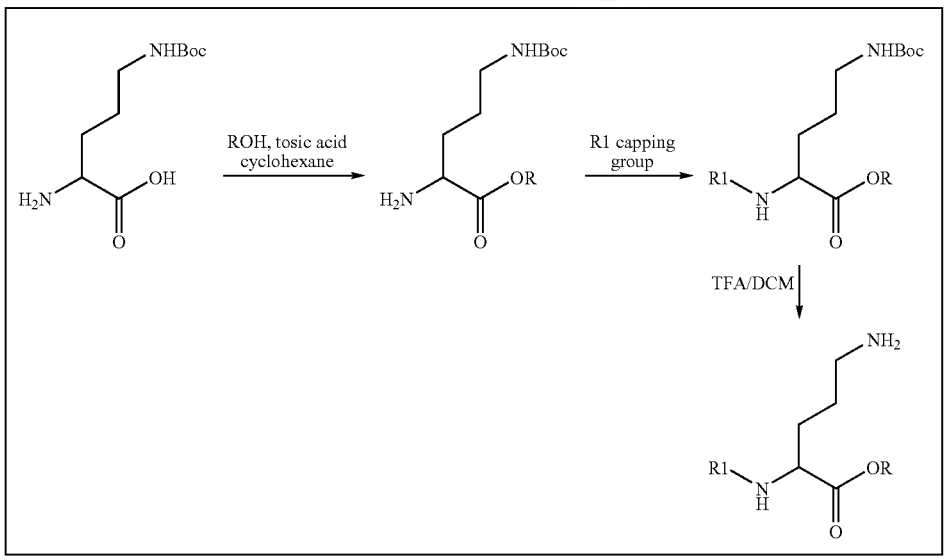
Scheme 3 illustrates an alternative route to 3-substituted β-carbolines of the invention, using linkage via a secondary amine, ether or thioether:
Scheme 3
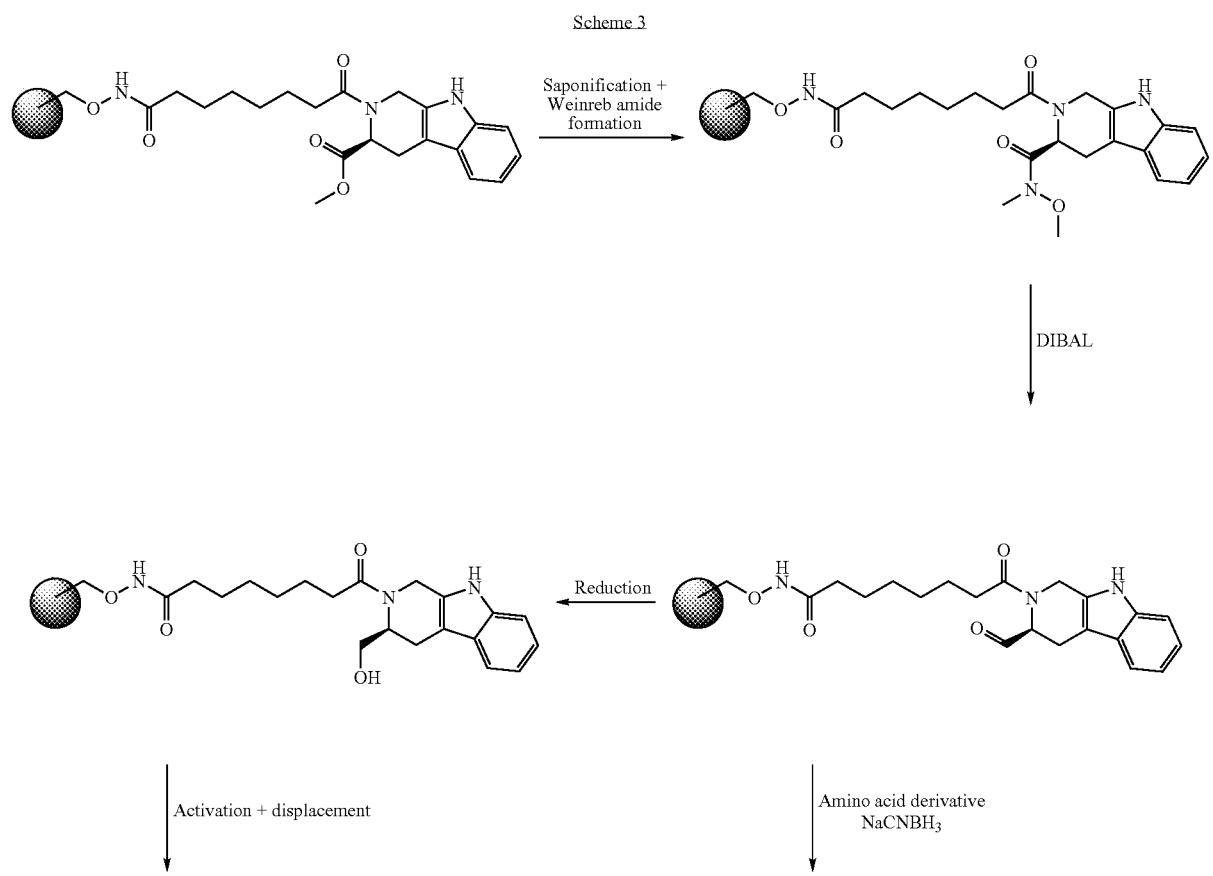

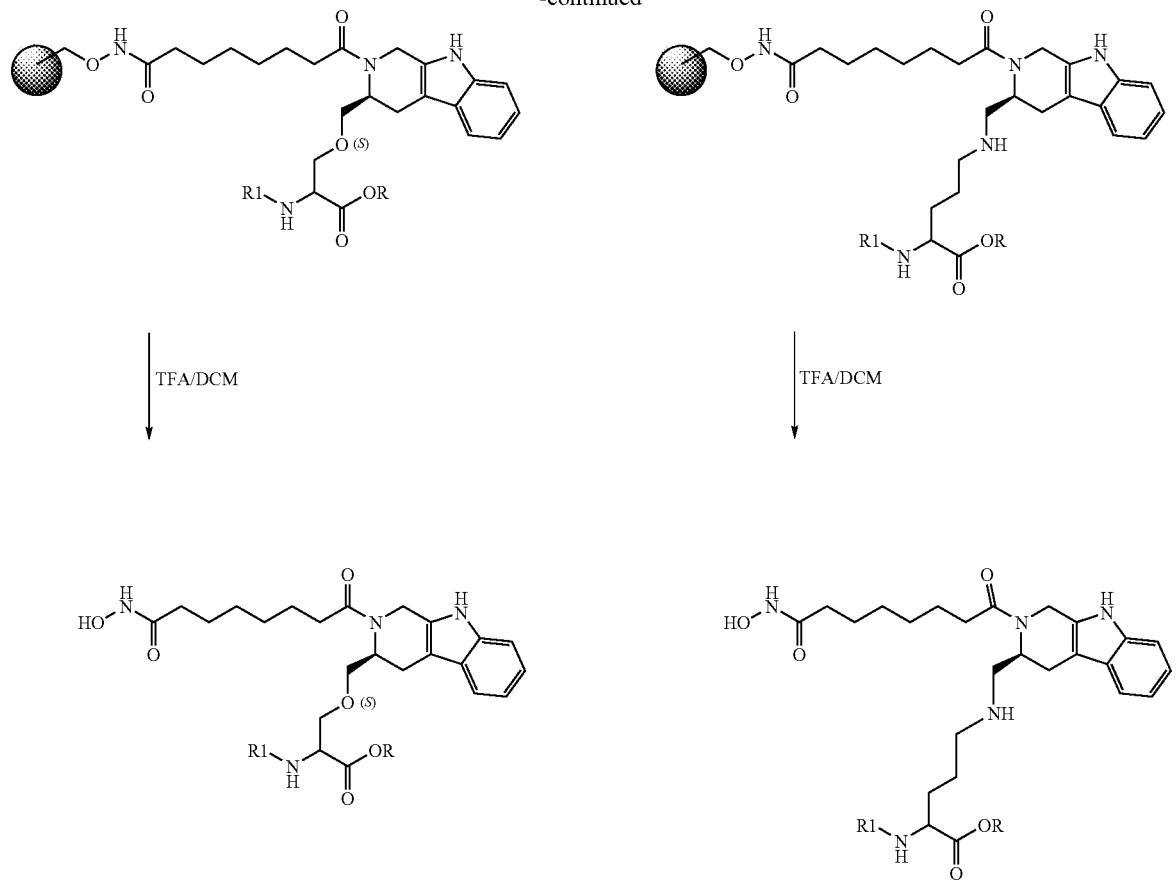
Scheme 4 illustrates a route to compounds of the invention which are 1-substituted β-carbolines:
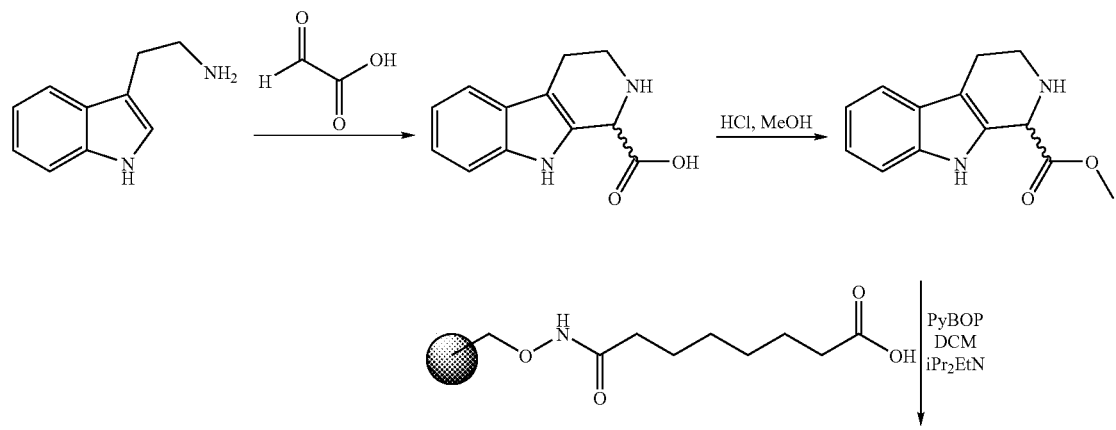

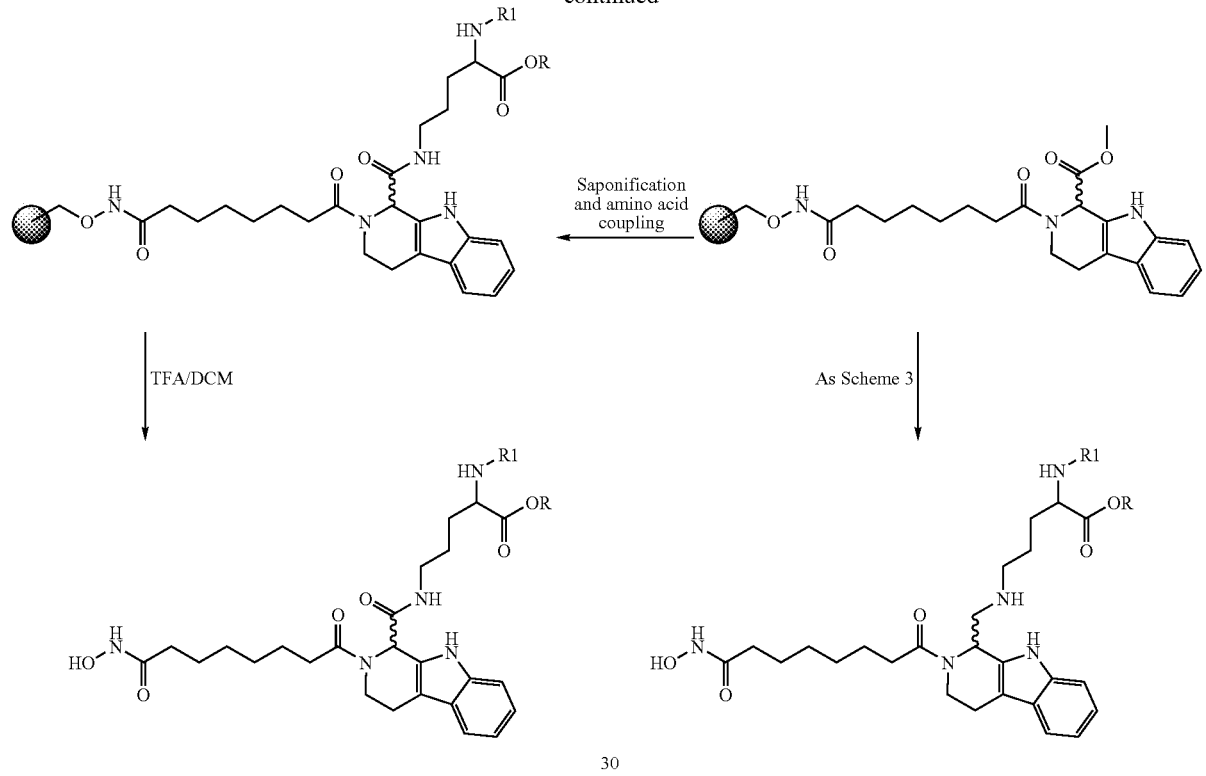
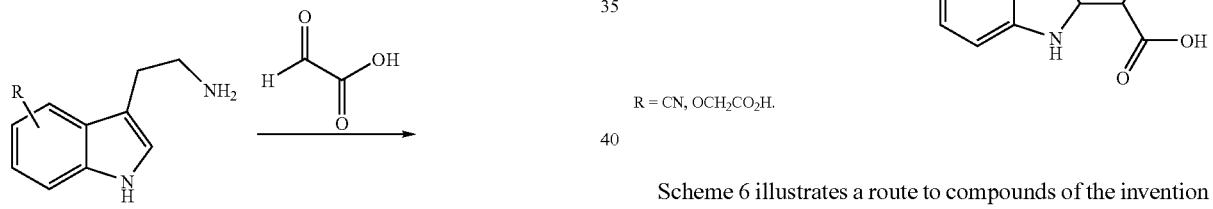
Substitution in the aryl ring can be accessed using appropriate tryptamine derivatives by the route shown in Scheme 5.
Scheme 5
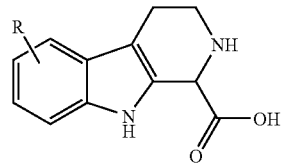
R = CN, OCH$_2$CO$_2$H.
Scheme 6 illustrates a route to compounds of the invention which are substituted tetrahydroisoquinoline derivatives:
Scheme 6
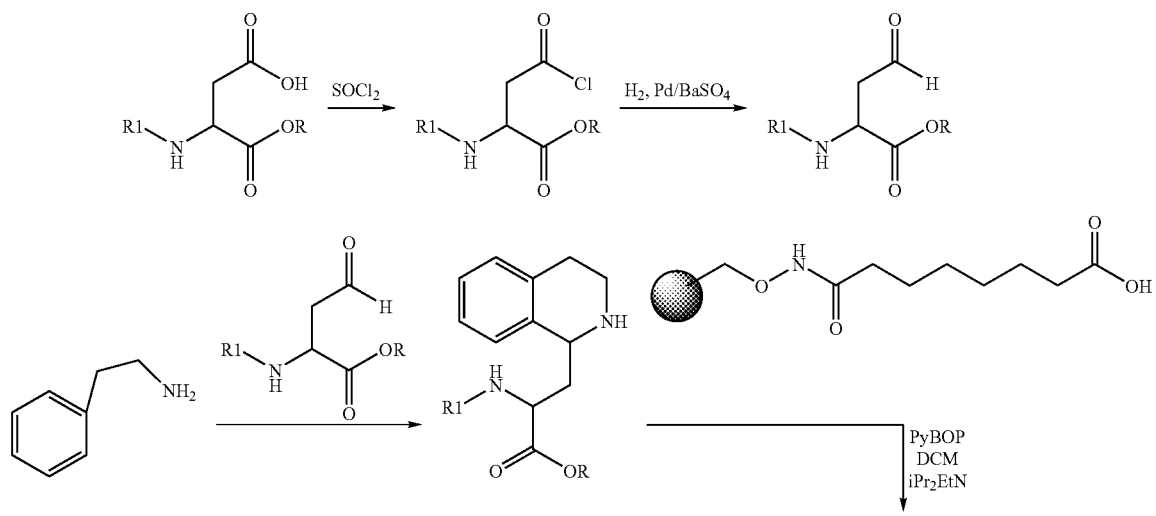

-continued
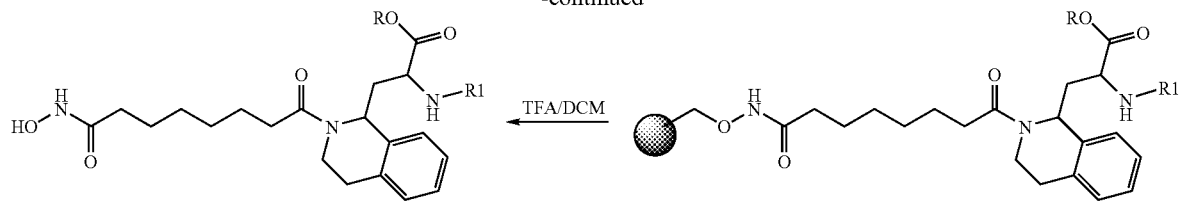
Scheme 7 illustrates a route to compounds of the invention wherein Z is —NHC(=O)— and L is $CH_2$—O:
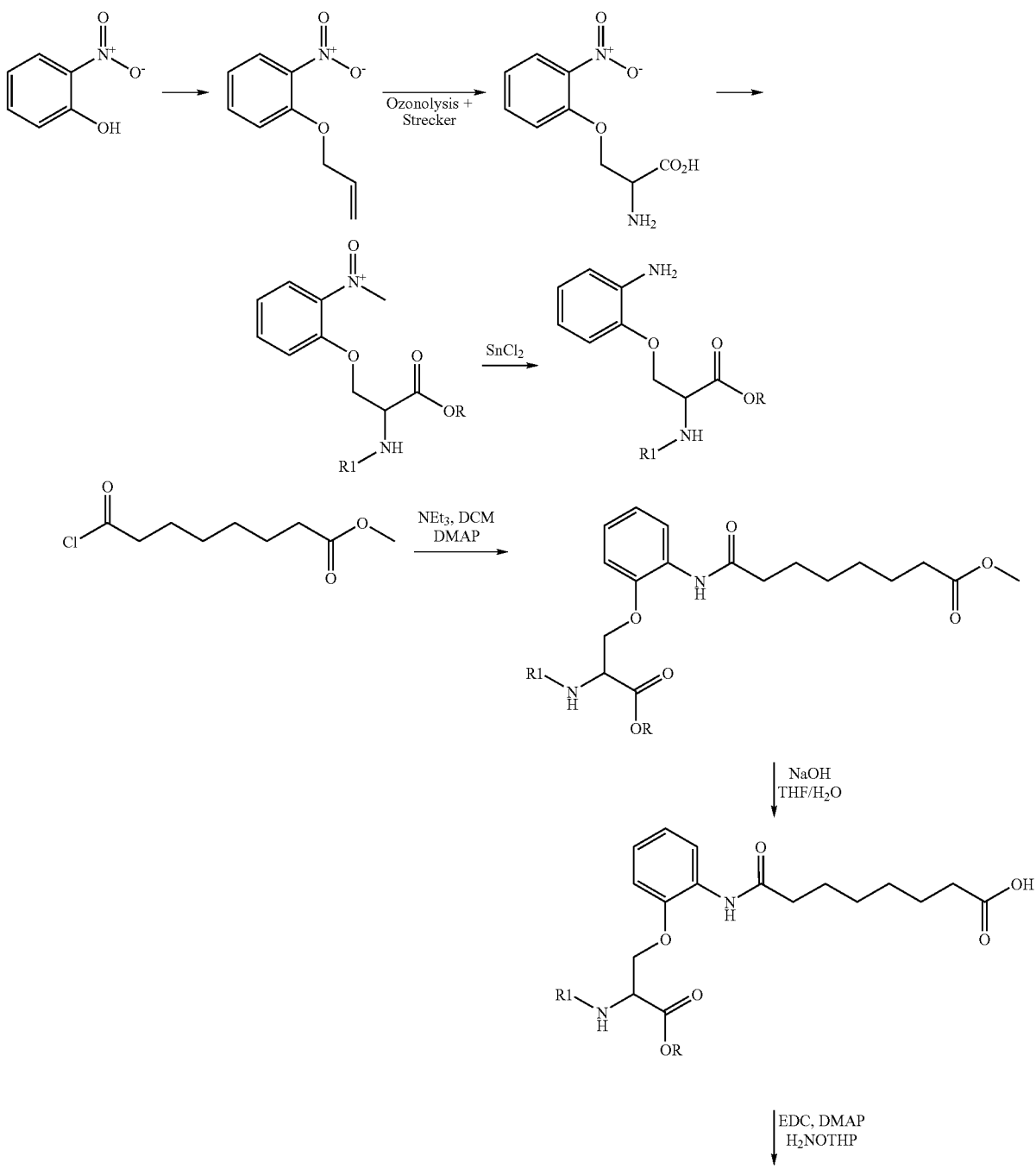

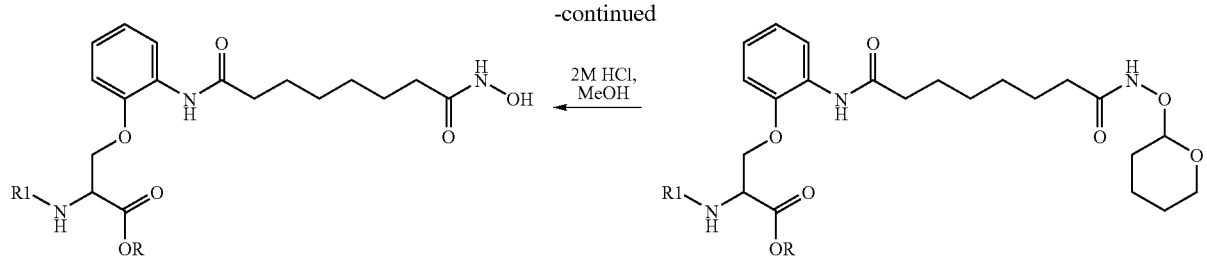
Scheme 8 illustrates a route to compounds of the invention which include a cyclic amino acid template, for example derived from proline:
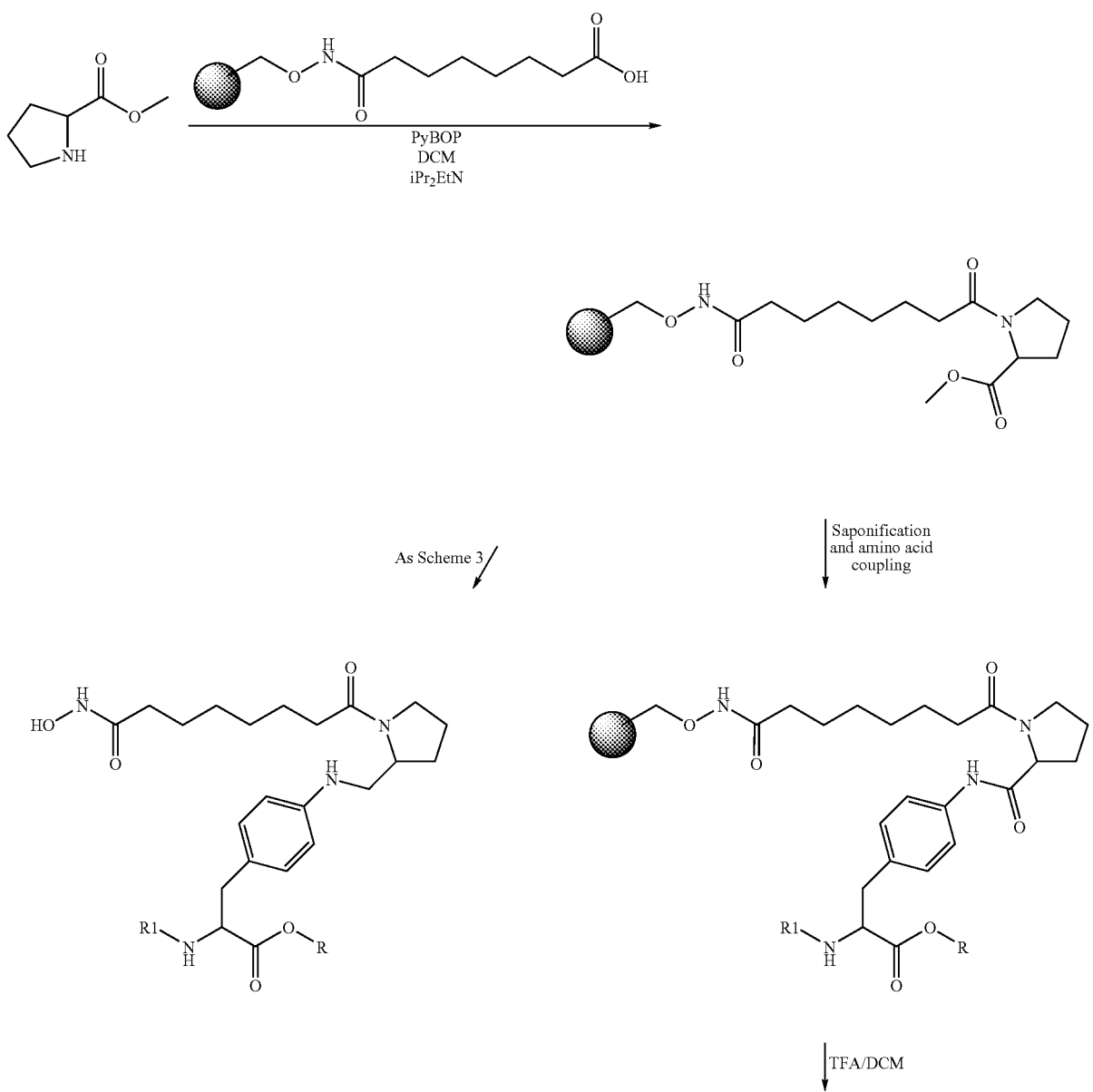

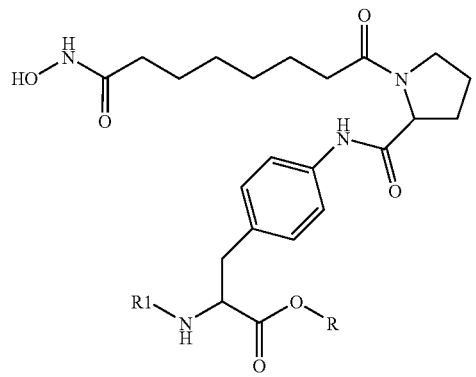

The following Examples illustrate the preparation of specific compounds of the invention, and the HDAC inhibitory properties thereof: In the Examples:

Commercially available reagents and solvents (HPLC grade) were used without further purification.

Microwave irradiation was carried out using a CEM Discover focused microwave reactor. Solvents were removed using a GeneVac Series I without heating or a Genevac Series II with VacRamp at 30° C. or a Buchi rotary evaporator.

Purification of compounds by flash chromatography column was performed using silica gel, particle size 40-63 µm (230-400 mesh) obtained from Silicycle. Purification of compounds by preparative HPLC was performed on Gilson systems using reverse phase ThermoHypersil-Keystone Hyperprep HS C18 columns (12 µm, 100×21.2 mm), gradient 20-100% B (A=water/0.1% TFA, B=acetonitrile/0.1% TFA) over 9.5 min, flow=30 ml/min, injection solvent 2:1 DMSO: acetonitrile (1.6 ml), UV detection at 215 nm.

$^1$H NMR spectra were recorded on a Bruker 400 MHz or 300 MHz AV spectrometer in deuterated solvents. Chemical shifts (δ) are in parts per million. Thin-layer chromatography (TLC) analysis was performed with Kieselgel 60 F$_{254}$ (Merck) plates and visualized using UV light.

Analytical HPLCMS was performed on Agilent HP1100, Waters 600 or Waters 1525 LC systems using reverse phase Hypersil BDS C18 columns (5 µm, 2.1×50 mm), gradient 0-95% B (A=water/0.1% TFA, B=acetonitrile/0.1% TFA) over 2.10 min, flow=1.0 ml/min. UV spectra were recorded at 215 nm using a Gilson G1315A Diode Array Detector, G1214A single wavelength UV detector, Waters 2487 dual wavelength UV detector, Waters 2488 dual wavelength UV detector, or Waters 2996 diode array UV detector. Mass spectra were obtained over the range m/z 150 to 850 at a sampling rate of 2 scans per second or 1 scan per 1.2 seconds using Micromass LCT with Z-spray interface or Micromass LCT with Z-spray or MUX interface. Data were integrated and reported using OpenLynx and OpenLynx Browser software The following abbreviations have been used:

| | |
|---|---|
| MeOH = | methanol |
| EtOH = | ethanol |
| EtOAc = | ethyl acetate |
| Boc = | tert-butoxycarbonyl |
| DCM = | dichloromethane |
| DMF = | dimethylformamide |
| DMSO = | dimethyl sulfoxide |
| TFA = | trifluoroacetic acid |
| THF = | tetrahydrofuran |
| Na$_2$CO$_3$ = | sodium carbonate |
| HCl = | hydrochloric acid |
| NaIO$_4$ = | sodium periodate |
| LiI = | Lithium iodide |
| DIPEA = | diisopropylethylamine |
| NaH = | sodium hydride |
| NaOH = | sodium hydroxide |
| NaHCO$_3$ = | sodium hydrogen carbonate |
| Pd/C = | palladium on carbon |
| TBME = | tert-butyl methyl ether |
| N$_2$ = | nitrogen |
| PyBop = | benzotriazole-1-yl-oxy-tris-pyrrolidino-phosphonium hexafluorophosphate |
| DMAP = | 4-Dimethylaminopyridine |
| Na$_2$SO$_4$ = | sodium sulphate |
| Et$_3$N = | triethylamine |
| NH$_3$ = | ammonia |
| TMSCl = | trimethylchlorosilane |
| NH$_4$Cl = | ammonium chloride |
| LiAlH$_4$ = | lithium aluminium hydride |
| pyBrOP = | Bromo-tris-pyrrolidino phosphonium hexafluorophosphate |
| MgSO$_4$ = | magnesium sulfate |
| $^n$BuLi = | n-butyllithium |
| CO$_2$ = | carbon dioxide |
| EDCl = | N-(3-Dimethylaminopropyl)-N-ethylcarbodiimide hydrochloride |
| Et$_2$O = | diethyl ether |
| LiOH = | lithium hydroxide |
| HOBt = | 1-hydroxybenzotriazole |
| ELS = | Evaporative Light Scattering |
| TLC = | thin layer chromatography |
| ml = | millilitre |
| g = | gram(s) |
| mg = | milligram(s) |
| mol = | moles |
| mmol = | millimole(s) |
| LCMS = | high performance liquid chromatography/mass spectrometry |
| NMR = | nuclear magnetic resonance |
| r.t. = | room temperature |

Preparation of Amino Acid Esters

The synthesis of (S)-2-tert-Butoxycarbonylamino-4-hydroxy-butyric acid cyclopentyl ester and (S)-4-Bromo-2-tert-butoxycarbonylamino-butyric acid cyclopentyl ester is outlined below in Scheme 9

The (R) enantiomers were prepared using the same methodology from the corresponding D-Homoserine.

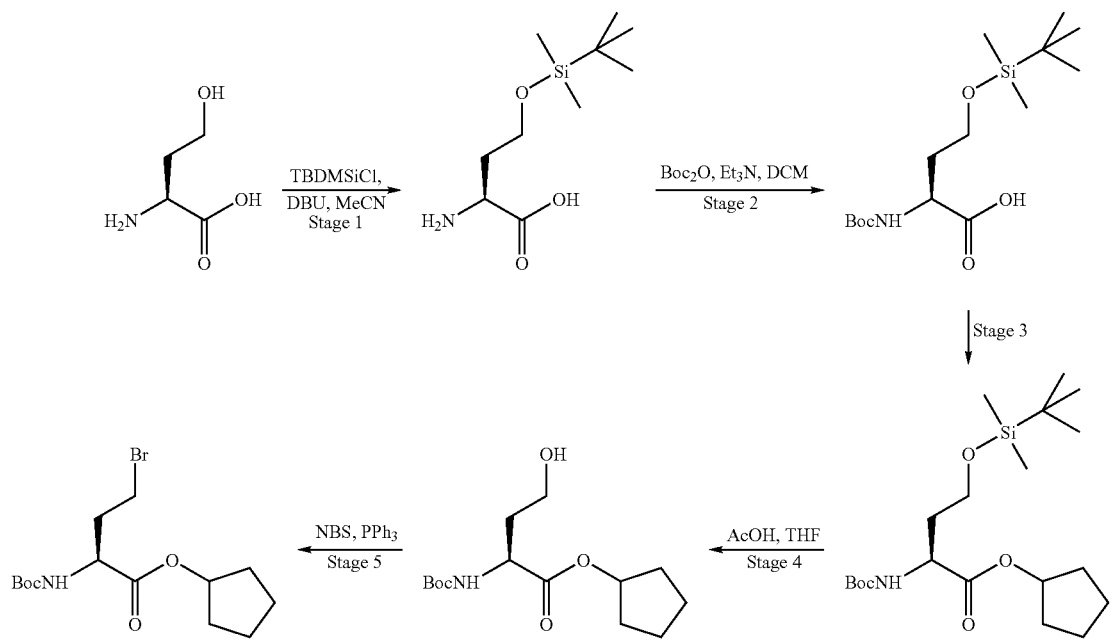

Scheme 9

Stage 1: (S)-2-Amino-4-(tert-butyl-dimethyl-silanyloxy)-butyric acid

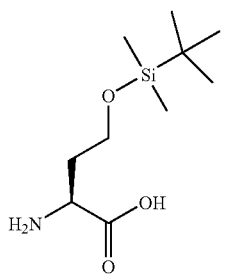

To a suspension of L-Homoserine (1 g, 8.4 mmol) in acetonitrile (10 ml) at 0° C. was added 1,8-Diazabicyclo[5.4.0]undec-7-ene (1.32 ml, 8.8 mmol). Tert-butyl-dimethyl-silyl chloride (1.33 g, 8.8 mmol) was then added portionwise over 5 minutes and the reaction mixture allowed to warm to room temperature and stirred for 16 hours. A white precipitate had formed which was filtered off and washed with acetonitrile before drying under vacuum. The title compound was isolated as a white solid (1.8 g, 92%). $^1$H NMR (300 MHz, DMSO), δ: 7.50 (1H, bs), 3.70 (1H, m), 3.35 (4H, bm), 1.95 (1H, m), 1.70 (1H, m), 0.90 (9H, s), 0.10 (6H, s).

Stage 2: (S)-2-tert-Butoxycarbonylamino-4-(tert-butyl-dimethyl-silanyloxy)-butyric acid

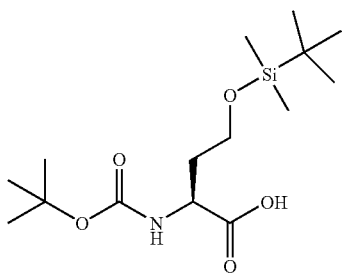

The suspension of Stage 1 product (1.8 g, 7.7 mmol) in DCM (100 ml) at 0° C. was treated with triethylamine (2.15 ml, 15.4 mmol) and Di-tert-butyl dicarbonate (1.77 g, 8.1 mmol). The reaction mixture was stirred at room temperature for 16 hours for complete reaction. The DCM was removed under reduced pressure and the mixture was treated with ethyl acetate/brine. The ethyl acetate layer was dried over magnesium sulphate and evaporated under reduced pressure. The crude product was taken forward to the next stage without further purification (2.53 g, 99%). $^1$H NMR (300 MHz, CDCl$_3$), δ: 7.50 (1H, bs), 5.85 (1H, d, J=6.5 Hz), 4.30 (1H, m), 3.75 (2H, m), 1.95 (2H, m), 1.40 (9H, s), 0.85 (9H, s), 0.10 (6H, s).

Stage 3: (S)-2-tert-Butoxycarbonylamino-4-(tert-butyl-dimethyl-silanyloxy)-butyric acid cyclopentyl ester

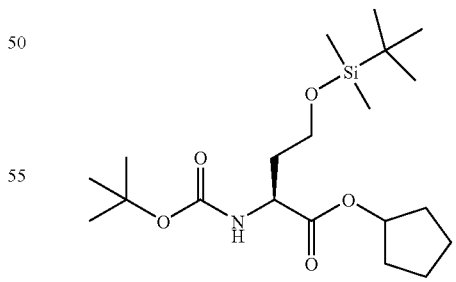

To a solution of (S)-2-tert-Butoxycarbonylamino-4-(tert-butyl-dimethyl-silanyloxy)-butyric acid (2.53 g, 7.6 mmol) in DCM (50 ml) at 0° C. was added cyclopentanol (1.39 ml, 15.3 mmol), EDC (1.61 g, 8.4 mmol) and DMAP (0.093 g, 0.76 mmol). The reaction mixture was stirred for 16 hours at room temperature before evaporation under reduced pressure. The crude residue was dissolved in ethyl acetate (100 ml) and washed with 1M HCl, 1M Na₂CO₃ and brine. The organic layer was then dried over magnesium sulphate and evaporated under reduced pressure. The product was purified by column chromatography using ethyl acetate/heptane (1:4) to give 2.24 g, 73% yield of title compound. LCMS purity 100%, m/z 402.5 [M⁺+H], ¹H NMR (300 MHz, CDCl₃), δ: 5.20 (1H, d, J=6.3 Hz), 5.15 (1H, m), 4.20 (1H, m), 3.6 (2H, m), 2.00 (1H, m), 1.95-1.55 (9H, bm), 1.40 (9H,s), 0.85 (9H,s), 0.10 (6H,s).

Stage 4:
(S)-2-tert-Butoxycarbonylamino-4-hydroxy-butyric acid cyclopentyl ester

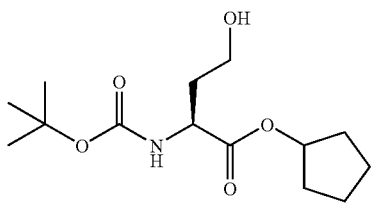

(S)-2-tert-Butoxycarbonylamino-4-(tert-butyl-dimethyl-silanyloxy)-butyric acid cyclopentyl ester (1.57 g, 3.9 mmol) was dissolved in acetic acid:THF:water (3:1:1, 100 ml). The reaction mixture was stirred at 30° C. for 16 hours for complete reaction. Ethyl acetate (200 ml) was added and washed with 1M Na₂CO₃, 1M HCl and brine. The ethyl acetate extracts were dried over magnesium sulphate and evaporated under reduced pressure to give the product as a clear oil which crystallised on standing (1.0 g, 95%). LCMS purity 100%, m/z 310.3 [M⁺+Na], ¹H NMR (300 MHz, CDCl₃), δ: 5.40 (1 H, d, J=6.5 Hz), 5.20 (1 H, m), 4.40 (1H, m), 3.65 (2H, m), 2.15 (1H, m), 1.90-1.55 (9H, bm), 1.45 (9H, s).

Stage: 5 (S)-4-Bromo-2-tert-butoxycarbonylamino-butyric acid cyclopentyl ester

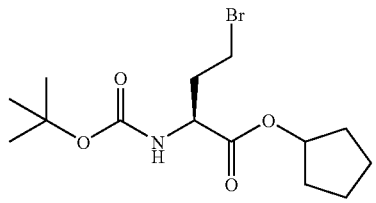

To a slurry of N-bromo succinimide (1.86 g, 10.4 mmol) in DCM (16.2 ml) was added a solution of triphenyl phosphine (2.56 g, 9.74 mmol) in DCM (7.2 ml). The solution was stirred for a further 5 minutes after addition. Pyridine (338 µl, 4.18 mmol) was added, followed by a solution of (S)-2-tert-butoxycarbonylamino-4-hydroxy-butyric acid cyclopentyl ester (1.0 g, 3.48 mmol) in DCM (8.8 ml). The solution was stirred for 18 hrs, concentrated in vacuo and the residual solvent azeotroped with toluene (3×16 ml). The residue was triturated with diethyl ether (10 ml) and ethyl acetate:heptane (1:9, 2×10 ml). The combined ether and heptane solutions was concentrated onto silica and purified by column chromatography using ethyl acetate/heptane (1:9-2:8) to provide 1.02 g (84% yield) of title compound. ¹H NMR (300 MHz, CDCl₃), δ: 5.30-5.05 (2 H, m), 4.45-4.30 (1H, m), 3.45 (2H, t, J=7.3 Hz), 2.50-2.30 (1H, m), 2.25-2.10 (1H, m), 1.95-1.60 (8H, b m), 1.47 (9H, s).

The Synthesis of (S)-2-tert-Butoxycarbonylamino-5-hydroxy-pentanoic acid cyclopentyl ester and (S)-5-Bromo-2-tert-butoxycarbonylamino-pentanoic acid cyclopentyl ester is Outlined Below In Scheme 10

The (R) enantiomers were prepared using the same methodology from the corresponding Boc-D-Glu(OBzl)-OH.

Additional literature references relating to this route can be found within *J. Org. Chem.* 1984, 49, 3527-3534.

Scheme 10

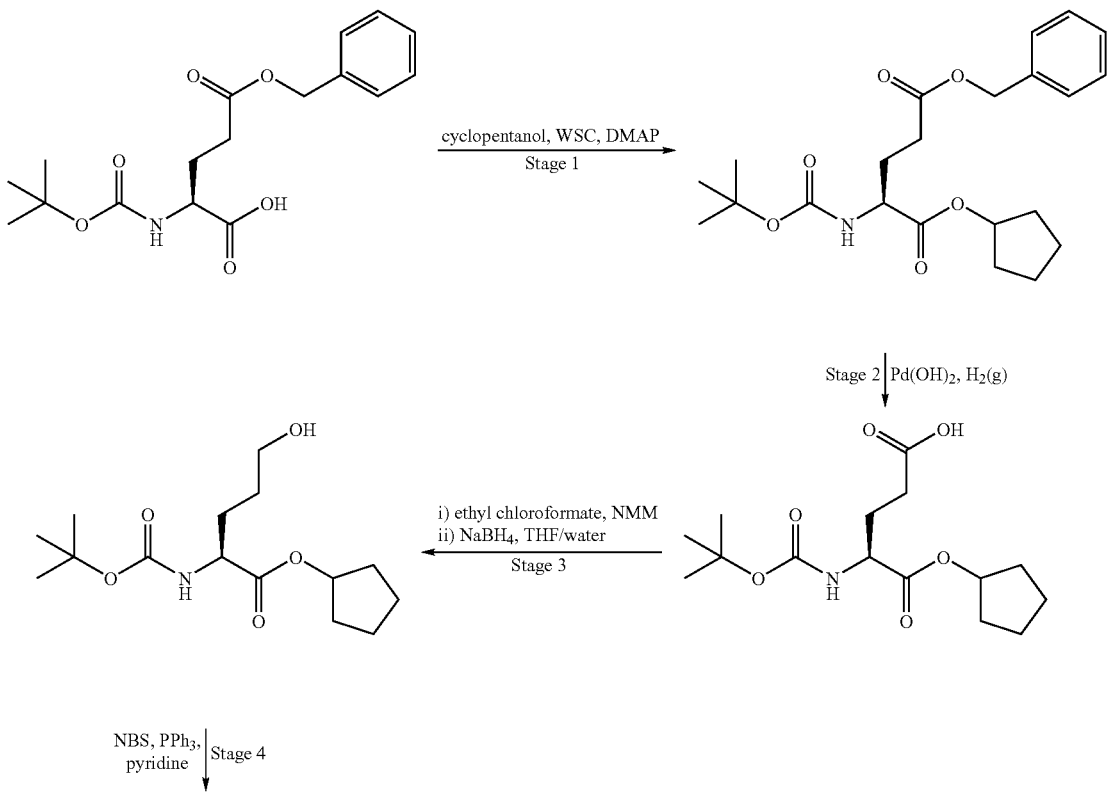

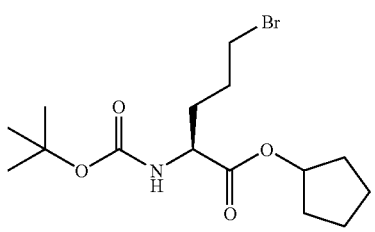

Stage 1:
(S)-2-tert-Butoxycarbonylamino-pentanedioic acid 5-benzyl ester 1-cyclopentyl ester

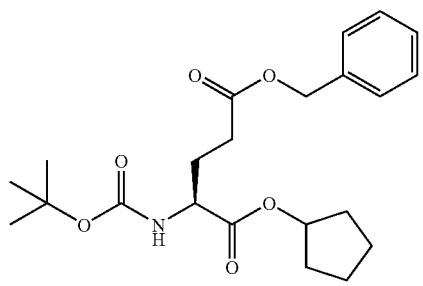

To a solution of Boc-L-Glu(OBzl)-OH (15 g, 44.5 mmol) in dichloromethane (220 ml) in an ice-bath, was added cyclopentanol (4.8 ml, 53.3 mmol), EDC (9.4 g, 48.9 mmol) and DMAP (543 mg, 4.4 mmol). The reaction mixture was allowed to warm to room temperature and stirred for 12 hours for complete reaction. The reaction mixture was diluted with DCM (200 ml) and washed with 1M HCl, 1M $Na_2CO_3$ and brine. The organic layer was then dried over magnesium sulphate and evaporated under reduced pressure. The product was purified by column chromatography using ethyl acetate/heptane (1:4) to give 12.4 g, 69% yield of title compound as a white solid. $^1$H NMR (300 MHz, $CDCl_3$), δ: 7.38 (5H, m), 5.70 (1H, m), 5.10 (2H, s), 5.05 (1H, m), 4.25 (1H, m), 2.47 (2H, m), 2.15 (1H, m), 1.95-1.55 (9H, bm), 1.47 (9H, s).

Stage 2:
(S)-2-tert-Butoxycarbonylamino-pentanedioic acid 1-cyclopentyl ester

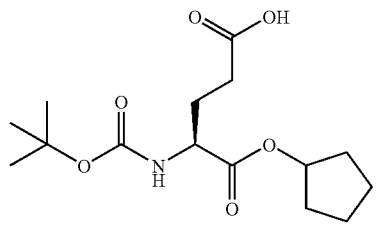

(S)-2-tert-Butoxycarbonylamino-pentanedioic acid 5-benzyl ester 1-cyclopentyl ester (12.4 g, 30.5 mmol) was dissolved in EtOAc (200 ml) and purged with nitrogen before addition of 20% $Pd(OH)_2$ on carbon catalyst (1.3 g). The reaction flask was then purged with hydrogen gas for a period of 5 minutes before leaving under a balloon of hydrogen for 5 hours for complete reaction. The catalyst was removed by filtration, washing with 50 ml EtOAc and the combined mother liquors were evaporated under reduced pressure. The title compound was isolated as a clear oil (7.73 g, 85%) and required no further purification. $^1$H NMR (300 MHz, $CDCl_3$), δ: 10.00 (1H, bs), 5.70 (2H, m), 4.28 (1H, m), 2.47 (2H, m), 2.15 (1H, m), 1.95-1.55 (9H, bm), 1.47 (9H, s).

Stage 3:
(S)-2-tert-Butoxycarbonylamino-5-hydroxy-pentanoic acid cyclopentyl ester

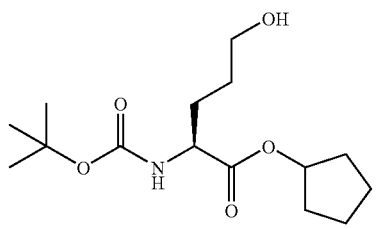

Ethyl chloroformate (2.45 ml, 25.6 mmol) was added at −20° C. to a stirred solution of (S)-2-tert-Butoxycarbonylamino-pentanedioic acid 1-cyclopentyl ester (6.73 g, 21.4 mmol) and N-methyl morpholine (3.05 ml, 27.8 mmol) in THF (50 ml). The reaction mixture became very thick with precipitation of a white solid. The reaction was therefore diluted further with THF (100 ml) to aid mixing and left stirring at −20° C. for 2 hours. The precipitated mass was filtered off and the filtrate was added over a period of 20 minutes to a solution of sodium borohydride (2.43 g, 64.1 mmol) in THF (20 ml) and water (5 ml) at 0° C. The reaction mixture was allowed to stir to room temperature and left for 4 hours for complete reaction. The mixture was acidified to pH 5 with 1M HCl and the THF removed under reduced pressure. The aqueous solution was extracted with EtOAc (3×100 ml) and dried over magnesium sulphate. The product was purified by column chromatography (DCM-5% MeOH/DCM) and isolated as a clear oil (5.0 g, 78%). $^1$H NMR (300 MHz, $CDCl_3$), δ: 5.20 (2H, m), 4.25 (1H, m), 3.65 (2H, m), 2.00-1.57 (12H, bm), 1.47 (9H, s).

Stage 4:
(S)-5-Bromo-2-tert-butoxycarbonylamino-pentanoic acid cyclopentyl ester

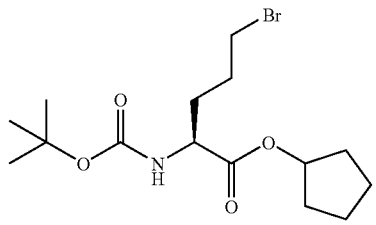

To a slurry of N-bromo succinimide (3.54 g, 19.9 mmol) in DCM (30 ml) was added a solution of triphenyl phosphine (4.87 g, 18.8 mmol) in DCM (15 ml). The solution was stirred for a further 5 minutes before addition of pyridine (644 μl, 7.96 mmol) and a solution of (S)-2-tert-Butoxycarbonylamino-5-hydroxy-pentanoic acid cyclopentyl ester (2.0 g, 6.64 mmol) in DCM (20 ml). The solution was stirred for 18 hrs, concentrated in vacuo and the residual solvent azeotroped with toluene (3×30 ml). The residue was triturated with diethyl ether (30 ml) and ethyl acetate:heptane (1:9, 2×30 ml). The combined ether and ethyl acetate/heptane solutions was concentrated onto silica and purified by column chromatography using ethyl acetate/heptane (1:9-2:8) to provide 1.34 g (55% yield) of title compound as a clear oil. $^1$H NMR (300 MHz, CDCl$_3$), δ 5.25 (1 H, m), 5.05 (1H, bd), 3.45 (2H, m), 2.00-1.55 (12H, bm), 1.45 (9H, s).

The Synthesis of (S)-tert-Butoxycarbonylamino-(4-hydroxyphenyl)-acetic acid cyclopentyl ester is Outlined Below in Scheme 11

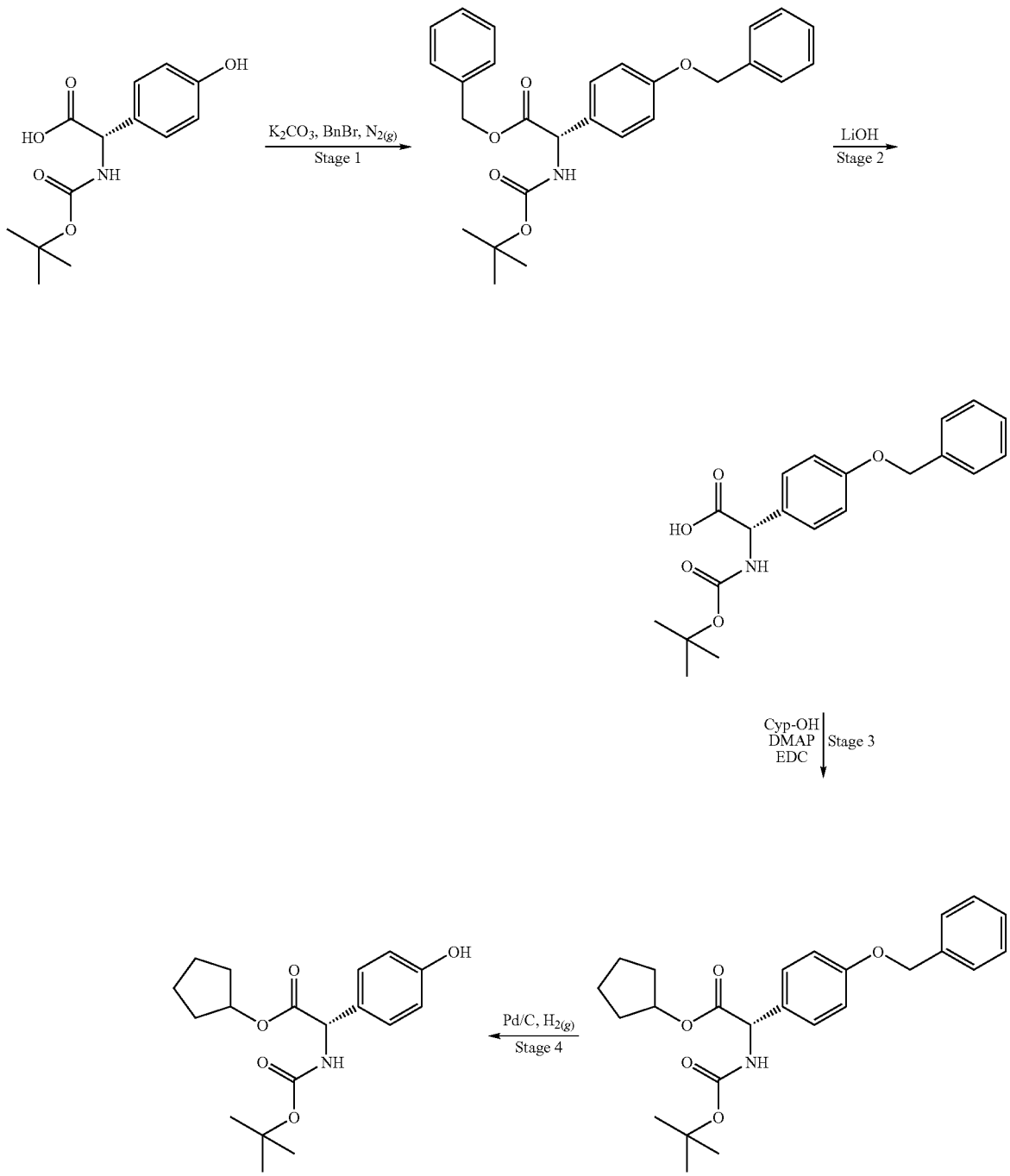

Stage 1: (S)-(4-Benzyloxy-phenyl)-tert-butoxycarbonylamino-acetic acid benzyl ester

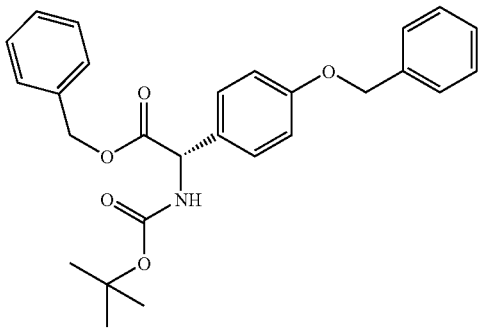

To a solution of (S)-tert-butoxycarbonylamino-(4-hydroxy-phenyl)-acetic acid (32.03 g, 120 mmol) in DMF (300 ml) was added potassium carbonate (35 g, 252 mmol) and benzylbromide (30 ml, 252 mmol). The reaction mixture was stirred at 50° C. under a nitrogen atmosphere for 17 h. The mixture was poured into water (1 l) and extracted with EtOAc (3×600 ml). The combined organic extracts were washed with water (3×600 ml), brine (600 ml), dried over magnesium sulfate, filtered and evaporated in vacuo to yield a yellow oil (49.4 g, 92%). LCMS purity 100%, m/z 470 [M$^+$+Na]$^+$.

Stage 2: (S)-(4-Benzyloxy-phenyl)-tert-butoxycarbonylamino-acetic acid

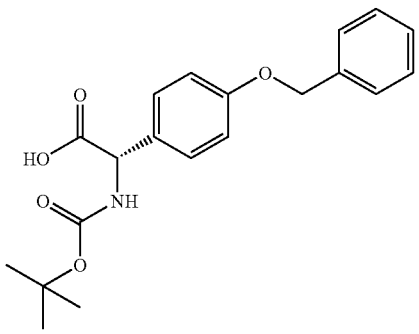

Stage 2 ester (49.4 g, 110.4 mmol) was dissolved in dioxane (250 ml) and water (250 ml) and lithium hydroxide (26.44 g, 1.10 mol) was added. The reaction mixture was stirred at r.t. for 2 h. EtOAc (500 ml) was added and the solid formed collected by filtration. It was suspended in water (1 l) and acidified to pH=3 with concentrated HCl. It was then extracted with EtOAc (3×500 ml), dried over magnesium sulfate and concentrated to dryness to yield a yellow oil (30.17 g, mixture of product and benzyl alcohol). The oil was taken up in 2N NaOH solution (200 ml) and washed with EtOAc (2×200 ml). The organics were combined and concentrated in vacuo to yield a thick yellow oil. This oil was triturated with a small amount of EtOAc to afford a solid collected by filtration and washed thoroughly with ether. The solid was suspended in water and the suspension acidified to pH=2 with concentrated HCl under vigorous stirring. The solid was collected by filtration and redissolved in EtOAc (250 ml). The organic solution was washed with brine (250 ml), dried over magnesium sulfate, filtered and concentrated under reduced pressure to yield the expected product as a white solid (17.49 g, 44%). LCMS purity 100%, m/z 380 [M$^+$+Na]$^+$.

Stage 3: (S)-(4-Benzyloxy-phenyl)-tert-butoxycarbonylamino-acetic acid cyclopentyl ester

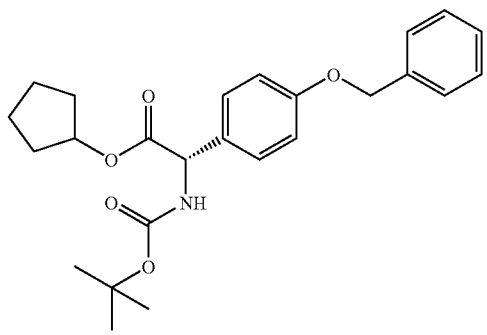

Stage 2 acid (10.64 g, 29.8 mmol) was dissolved in DCM (200 ml) and cooled down to 0° C. Cyclopentanol (5.4 ml, 59.5 mmol) was added, followed by DMAP (364 mg, 3.0 mmol) and EDC.HCl (6.28 g, 32.7 mmol). The reaction mixture was allowed to warm up to r.t. and then stirred for 2 h. The reaction mixture was washed with 1N HCl (200 ml), saturated aqueous Na$_2$CO$_3$ solution (200 ml), brine (200 ml), dried over magnesium sulfate, filtered and concentrated to dryness. The crude mixture was purified by column (heptane/EtOAc 9:1) to yield the expected product as a white solid (9.81 g, 77%). LCMS purity 100%, m/z 448 [M$^+$+Na]$^+$.

Stage 4: (S)-tert-Butoxycarbonylamino-(4-hydroxyphenyl)-acetic acid cyclopentyl ester

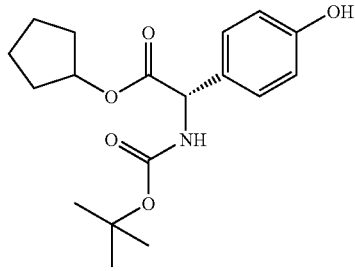

Stage 3 benzyl ether compound (1 g, 2.35 mmol) was dissolved in EtOAc (20 ml). Pd/C 10% (100 mg) was added. The flask was evacuated and placed under a hydrogen atmosphere and the reaction mixture was stirred overnight. The palladium residues were filtered over a pad of celite and the filtrate was evaporated to dryness to yield the expected product (808 mg, 100%). LCMS purity 100%, m/z 334 [M−H+$^+$]$^−$, $^1$H NMR (300 MHz, CDCl$_3$), δ: 1.45 (9 H, s, 3×CH$_3$), 1.50-1.62 (4H, m, 2×CH$_2$), 1.67-1.74 (2H, m, 2×CH$_2$), 5.16-5.22 (1H, m, OCH), 5.64 (1H, d, J=5.4 Hz, α-CH), 6.70 (2H, d, J=7.8 Hz, Ar), 7.16 (2H, d, J=8.4 Hz, Ar)

The Synthesis of (S)-2-tert-Butoxycarbonylamino-3-(4-hydroxy-phenyl)-propionic acid cyclopentyl ester is Outlined Below in Scheme 12

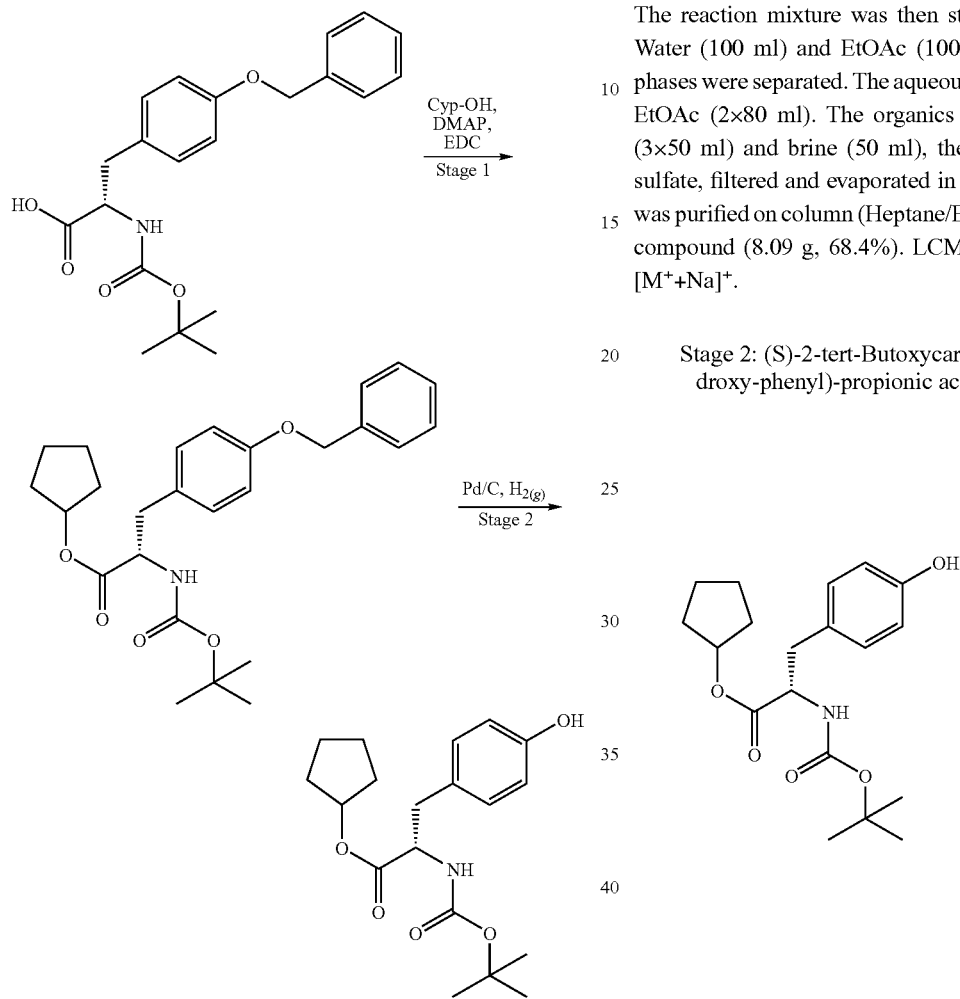

Stage 1: (S)-3-(4-Benzyloxy-phenyl)-2-tert-butoxycarbonylamino-propionic acid cyclopentyl ester

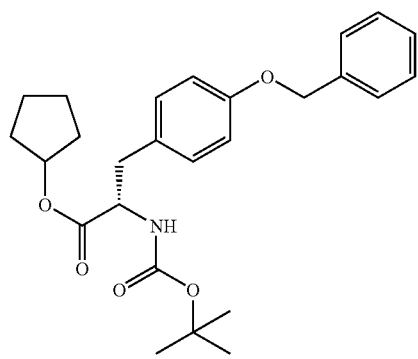

To a solution of (S)-3-(4-Benzyloxy-phenyl)-2-tert-butoxycarbonylamino-propionic acid (10 g, 26.9 mmol) in DMF (100 ml) was added cyclopentanol (4.6 g, 53.8 mmol) and DMAP (329 mg, 2.69 mmol). The solution was cooled down to 0° C. and EDC.HCl (5.4 g, 28.2 mmol) was added. The reaction mixture was then stirred at r.t. for 22 hours. Water (100 ml) and EtOAc (100 ml) were added and the phases were separated. The aqueous phase was extracted with EtOAc (2×80 ml). The organics were washed with water (3×50 ml) and brine (50 ml), then dried over magnesium sulfate, filtered and evaporated in vacuo. The crude product was purified on column (Heptane/EtOAc 7:3) to yield the title compound (8.09 g, 68.4%). LCMS purity 96.6%, m/z 462 $[M^++Na]^+$.

Stage 2: (S)-2-tert-Butoxycarbonylamino-3-(4-hydroxy-phenyl)-propionic acid cyclopentyl ester Stage 1 benzyl ether compound (8 g, 18.2 mmol) was dissolved in EtOAc (160 ml). Pd/C 10% (800 mg) was added. The flask was evacuated and placed under a hydrogen atmosphere and the reaction mixture was stirred for 30 hours after which TLC showed complete disappearance of starting material. The palladium residues were filtered over a pad of celite and the filtrate was evaporated to dryness to yield the expected product (5.57 g, 88%), $^1$H NMR (300 MHz, CDCl$_3$), δ: 1.43 (9 H, s, 3×CH$_3$), 1.52-1.74 (6H, m, 3×CH$_2$), 1.74-1.95 (2H, m, CH$_2$), 2.99 (2H, d, J=5.5 Hz, CH$_2$CH), 4.39-4.56 (1H, m, CHNH), 5.01 (1H, d, J=8.3 Hz, NH), 5.10-5.24 (1H, m, OCH), 6.73 (2H, d, J=8.1 Hz, Ar), 6.99 (2H, d, J=8.3 Hz, Ar)

The Synthesis of 6-formyl-benzo[b]thiophene-2-carboxylic acid (1-isobutoxy-ethoxy) amide is Outlined Below in Scheme 13.

Additional literature references relating to this route can be found within *Tetrahedron Letters*, 35, 2, 219-222 & WO 05/034880

Scheme 13

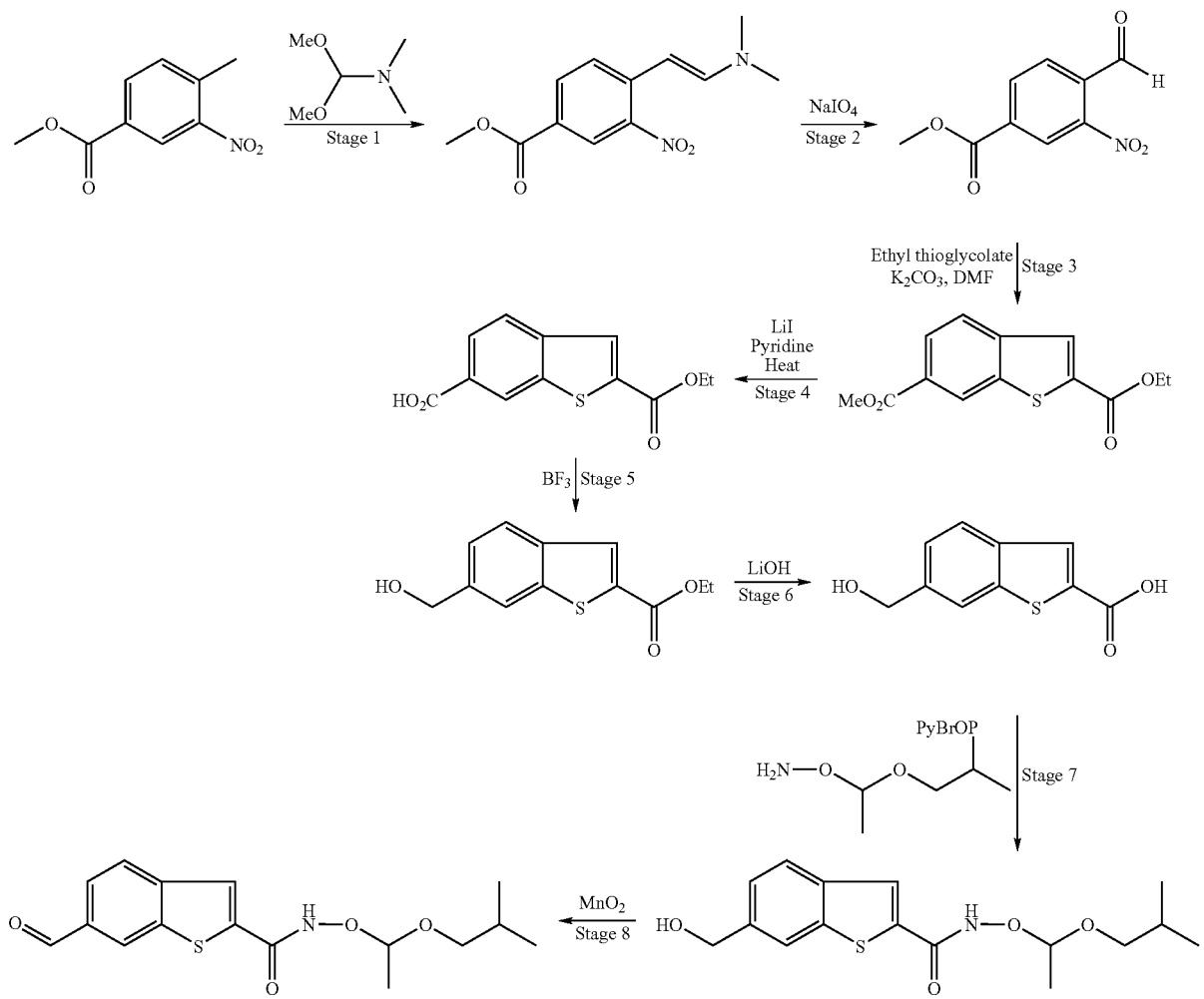

Stage 1: 4-(2-dimethylamino-vinyl)-3-nitrobenzoic acid methyl ester

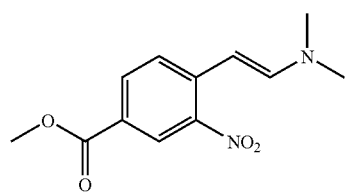

Methyl 4-methyl-3-nitrobenzoate (5 g, 25.6 mmol) was dissolved in DMF (25 mL, 5 vol) and to this was added N,N-dimethylformamide dimethylacetal (4.4 mL, 33.3 mmol). The mixture was allowed to stir at 140° C. for 3 h. The resulting deep red solution was allowed to cool and concentrated under vacuum. The residue was triturated with methanol and filtered. The filtrate was washed with methanol and dried on the sinter to yield 4-(2-dimethylamino-vinyl)-3-nitrobenzoic acid methyl ester (5.2 g, 80%). $^1$H NMR (300 MHz, DMSO), δ: 2.98 (6H, s, 2×CH$_3$), 3.87 (3H, s, CH$_3$), 5.58 (1H, m, CH), 7.72-7.83 (3H, m, ArH), 8.32 (1H, m, CH).

Stage 2: 4-Formyl-3-nitrobenzoic acid methyl ester

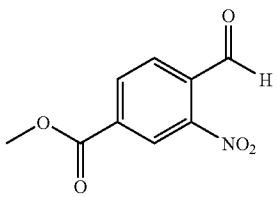

To a solution of the enamine (5 g, 20.0 mmol) in THF (50 mL, 10 vol) and water (50 mL, 10 vol) was added sodium periodate (12.8 g, 60.0 mmol) and the mixture allowed to stir for 2 h. The mixture was filtered and the resulting solids washed with EtOAc (500 mL). The organic layer was isolated, washed with NaHCO$_3$ (3×100 mL) and dried (MgSO$_4$). Concentration under vacuum afforded 4-formyl-3-nitrobenzoic acid methyl ester (3.9 g, 93%). LCMS m/z 210 [M$^+$+H]$^+$, $^1$H NMR (300 MHz, DMSO), δ: 3.96 (3H, s, OMe), 8.01 (1H, d, ArH), 8.39 (1H, d, ArH), 8.54 (1H, s, ArH), 10.31 (1H, s, CHO).

Stage 3: Benzo[b]thiophene-2,6-dicarboxylic acid 2-ethyl ester 6-methyl ester

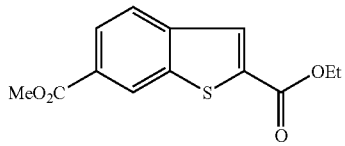

A mixture of 4-formyl-3-nitrobenzoic acid methyl ester (3.9 g, 18.7 mmol), mercapto-acetic acid ethyl ester (2.2 mL, 20.4 mmol) and $K_2CO_3$ (3.3 g, 24 mmol) in DMF (40 ml, 10 vol) was heated to 50° C. overnight. After cooling to r.t. the mixture was poured onto ice-cold water (250 mL) and the resulting mixture stirred for 40 min. The solid formed was isolated by filtration, washed with water (4×50 mL) and dried under vacuum to afford the title compound (3.9 g, 80%). LCMS m/z 265 $[M^++H]^+$, $^1H$ NMR (300 MHz, $CDCl_3$) δ: 1.40 (3H, t J=6.8 Hz, $CH_3$), 3.95 (3H, s, OMe), 4.40 (2H, q J=7.2 Hz, $CH_2$), 7.88 (1H, d J=8.0 Hz, ArH), 7.97-8.09 (2H, m. ArH), 8.56 (1H, s, ArH).

Stage 4: Benzo[b]thiophene-2,6-dicarboxylic acid 2-ethyl ester

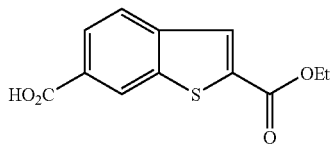

A mixture of benzo[b]thiophene-2,6-dicarboxylic acid 2-ethyl ester 6-methyl ester (3.9 g, 14.77 mmol) and LiI (10 g, 74.6 mmol) in anhydrous pyridine (30 ml, 9 vol) was stirred at reflux for 16 h. After cooling to r.t., the mixture was added (either as a melt or chipped out) to ice-cold 2N HCl (200 mL). The solid formed was isolated by filtration and washed with water (3×50 mL). The product was purified by recrystallisation from methanol to give the title compound (1.8 g, 49%). LCMS m/z 251 $[M^++H]^+$, $^1H$ NMR (300 MHz, DMSO), δ: 1.35 (3H, t J=6.9 Hz, $CH_3$), 4.38 (2H, q J=7.1 Hz, $CH_2$), 7.99 (1H, d J=8.3 Hz, ArH), 8.12 (1H, d J=8.3 Hz, ArH), 8.27 (1H, s, ArH), 8.70 (1H, s, ArH).

Stage 5: 6-Hydroxymethyl-benzo[b]thiophene-2-carboxylic acid ethyl ester

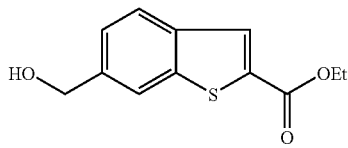

A solution of benzo[b]thiophene-2,6-dicarboxylic acid 2-ethyl ester (1.6 g, 6.4 mmol) in anhydrous THF (40 mL, 25 vol) was cooled to 0° C. To this $BH_3$ (1M in THF, 30 mL, 30.0 mmol) was added slowly. The reaction was allowed to warm to r.t. and stirred for 3 h. The solution was then cooled to 0° C. and quenched using 1N HCl (7.5 mL). The reaction mixture was concentrated under vacuum to remove all THF and the resulting solid isolated by filtration and dried under vacuum to give 6-hydroxymethyl-benzo[b]thiophene-2-carboxylic acid ethyl ester (1.3 g, 87%). LCMS m/z 237 $[M^++H]^+$, $^1H$ NMR (300 MHz, DMSO), δ: 1.34 (3H, t J=6.9 Hz, $CH_3$), 4.35 (2H, q J=7.1 Hz, $CH_2$), 4.65 (2H, s, $CH_2$), 6.53 (1H, br s, OH), 7.42 (1H, d J=9.4 Hz), 7.98 (3H, m, ArH), 8.18 (1H, s, ArH).

Stage 6: 6-Hydroxymethyl-benzo[b]thiophene-2-carboxylic acid

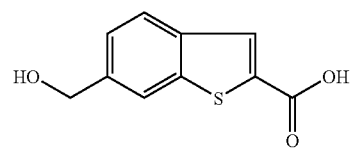

6-Hydroxymethyl-benzo[b]thiophene-2-carboxylic acid ethyl ester (2.4 g, 9.6 mmol, 1 eq) was dissolved in THF (10 mL, 4 vol) and water added (10 mL) along with LiOH (0.69 g, 28.8 mmol). The reaction mixture was stirred at 50° C. for 3 h and then concentrated to dryness and taken onto the next stage without purification.

Stage 7: 6-hydroxymethyl-benzo[b]thiophene-2-carboxylic acid (1-isobutoxy-ethoxy) amide

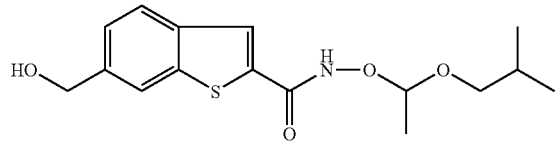

To a solution of 6-hydroxymethyl-benzo[b]thiophene-2-carboxylic acid (1.76 g, 8.4 mmol, 1 eq) in DMF was added PyBrOP (4.3 g, 9.2 mmol), O-(isobutoxy-ethyl)-hydroxylamine (11.5 mL, 84.0 mmol) (prepared via procedure in WO0160785) and DIPEA (2.9 mL, 16.7 mmol). The reaction mixture was allowed to stir at r.t. for 2 h then diluted with water (40 mL) and EtOAc (40 mL). The organic layer was isolated, washed with brine (50 mL) and concentrated. The residue was purified by chromatography on silica gel eluting with EtOAc/heptane (1:1) to afford the title compound (1.8 g, 67% over 2 steps). LCMS m/z 322 $[M^+–H]^+$, $^1H$ NMR (300 MHz, MeOD), δ: 0.83 (6H, d J=6.6 Hz, 2×$CH_3$), 1.32 (3H, d J=5.9 Hz, $CH_3$), 1.75 (1H, m, CH), 3.38 (2H, m, $CH_2$), 4.63 (2H, s, $CH_2$), 4.95 (1H, m, CH), 7.32 (1H, d J=8.2 Hz, ArH), 7.77 (3H, m, ArH).

Stage 8: 6-formyl-benzo[b]thiophene-2-carboxylic acid (1-isobutoxy-ethoxy)amide

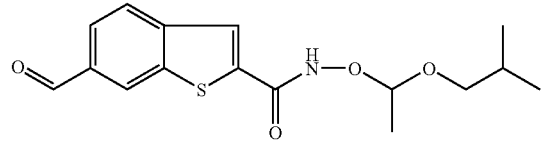

To a solution of 6-hydroxymethyl-benzo[b]thiophene-2-carboxylic acid (1-isobutoxy-ethoxy) amide (600 mg, 1.86 mmol) in DCM (3 mL) was added MnO$_2$ (2.1 g, 24.1 mmol). The mixture was stirred at ambient temperature for 30 min and then filtered through celite. The filtrate was concentrated to afford the title compound (435 mg, 82%). LCMS m/z 320 [M$^+$–H]$^+$, $^1$H NMR (300 MHz, MeOD), δ: 0.94 (6H, d J=6.7 Hz, 2×CH$_3$), 1.45 (3H, d J=5.3 Hz, CH$_3$), 1.87 (1H, m, CH), 3.40 (2H, m, CH$_2$), 5.08 (1H, dd J=5.2, 10.6 Hz, CH), 7.89-8.09 (3H, m, ArH), 8.55 (1H, s, ArH), 10.11 (1H, s, CHO). Synthesis of Compounds in FIG. 1 Exemplified by: Compound (1) and Compound (2).

Figure 1

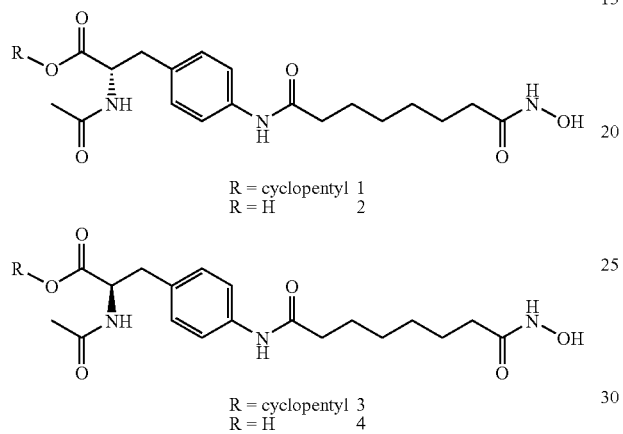

Stage 1: (S)-2-Amino-3-p-tolyl-propionic acid cyclopentyl ester

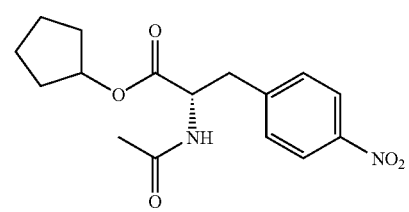

To a round bottomed flask fitted with a Dean-Stark apparatus and condenser was added *(S)-2-Amino-3-p-tolyl-propionic acid (10 g, 0.0475 mol), p-toluenesulfonic acid monohydrate (9.95 g, 0.052 mol), cyclopentanol (42.7 ml) and cyclohexane (75 ml) the reaction heated to 120° C. for 48 hrs. The flask was cooled and the precipitate collected by filtration and washed with TBME yielding the required ester as the tosyl salt 19.1 g.

*For compounds 3 and 4, (R)-2-Amino-3-p-tolyl-propionic acid was used.

Stage 2: (S)-2-Acetylamino-3-p-tolyl-propionic acid cyclopentyl ester

To (S)-2-Amino-3-p-tolyl-propionic acid cyclopentyl ester p-toluenesulfonic acid salt prepared in the above stage (10 g, 0.022 mol) was added dichloromethane 200 ml) under nitrogen. Triethylamine (6.29 ml, 0.044 mol) was added dropwise with stirring. Acetyl chloride (1.72 ml, 0.022 mol) in dichloromethane (50 ml) was added dropwise to the reaction. Acetyl chloride (0.1 ml) in DCM (0.5 ml) was added after 20 mins and the reaction reached completion after 1 hr. The organic phase was washed with saturated sodium bicarbonate (3×200 ml), dried (Na$_2$SO$_4$) and the solvent removed in vacuo. The required product was obtained 6.62 g, 93% yield and was used in the next step without further purification. m/z 321 [M$^+$+H]$^+$ Stage 3: (S)-2-Acetylamino-3-(4-amino-phenyl)-propionic acid cyclopentyl ester

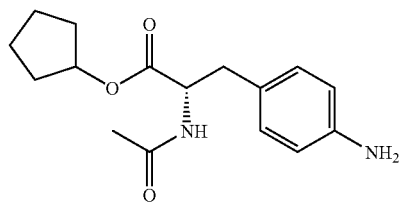

To a round bottomed flask was added ethyl acetate (30 ml), (S)-2-Acetylamino-3-p-tolyl-propionic acid cyclopentyl ester (0.45 g, 1.4 mmol) and Pd/C (0.45 g). The flask was evacuated and filled with hydrogen (balloon). The reaction mixture was stirred for 2 h under a hydrogen atmosphere. The solution was filtered through celite and the celite washed with ethyl acetate. The solvent was removed to yield the required product (0.332 g, 81% yield), which was used in the next step without further purification. m/z 291 [M$^+$+H]$^+$; 313 [M$^+$+Na]$^+$ Stage 4: Immobilisation of linker with chlorotrityl-O—NH$_2$ resin

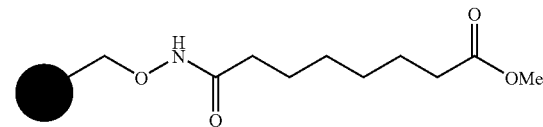

To a round bottomed flask charged with chlorotrityl-O—NH$_2$ resin (6 g, loading 1.14 mmol/g) and DCM (60 ml) was added diisopropylethylamine (5.30, 41.0 mmol). Methyl 8-chloro-8-oxooctanoate (4.2 g, 20.5 mmol) was slowly added to the reaction mixture with orbital shaking and the reaction mixture shaken for 48 hours. The resin was filtered and washed using the standard washed procedure, DMF, MeOH, DMF, MeOH, DCM, MeOH, DCM, MeOH×2, TBME×2. The resin was dried under vacuum.

Stage 5: Saponification

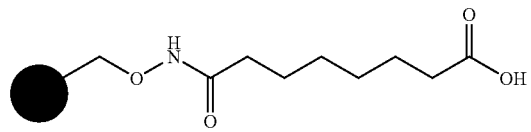

To a round bottomed flask charged with stage 4 resin (4 g, loading 1.14 mmol/g, 4.56 mmol) was added THF (16 ml) and MeOH (16 ml). To the reaction was added a solution of NaOH (0.91 g, 22.8 mmol) in water (16 ml). The reaction mixture was shaken for 48 hours. The resin was filtered and washed with water×2, MeOH×2, followed by a standard wash procedure. The resin was dried under vacuum.

Stage 6: (S)-2-Acetylamino-3-[4-(7-hydroxycarbam-oyl-heptanoylamino)-phenyl]-propionic acid cyclopentyl ester (1)

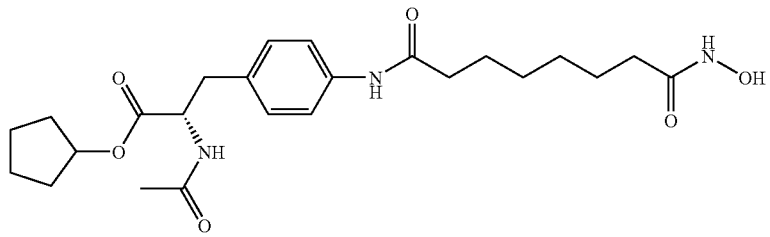

Hydroxylamine 2-chlorotrityl resin loaded with hexane-1,6-dicarboxylic acid (Stage 5 resin) (0.16 g, 1.14 mmol/g) was swollen in dichloromethane (5 ml). The resin was cooled to 0° C. and 1-Chloro-N,N,2-trimethyl-1-propenylamine (0.072 ml, 0.5 mmol) added dropwise. The reaction was allowed to reach room temperature and was shaken for 1.5 h. N-Acetyl-4-amino-L-phenylalanine cyclopentyl ester (0.159 g, 0.55 mmol) was added in anhydrous dichloromethane (10 ml) followed by triethylamine (0.102 ml). The reaction was shaken for a further 30 minutes. The resin was washed, DCM, DMF (×2), DCM, MeOH (×2), MeOH, TBME and dried. The required product was cleaved from resin with 2% TFA/DCM. The solvent was removed and the crude product purified by preparative HPLC. m/z 462 [M$^+$+H]$^+$, $^1$H NMR (400 MHz, d6-DMSO) δ: 1.25-1.26, 1.44-1.58, 1.7-1.75 (16H, 3×m, 8×CH$_2$), 1.76 (3H, s, CH$_3$CO), 1.93 (2H, t, CH$_2$), 2.27 (2 H, t, CH$_2$), 2.66 (2 H, ddd, ArCH$_2$), 4.66 (1 H, q, NHCH), 5.00 (1 H, m, CHO), 7.11, 7.48 (4 H, 2×d, Ar), 8.27 (1H, d, NHCO), 9.8 (1H, s), 10.34 (1H, s).

Stage 7: (S)-2-Acetylamino-3-[4-(7-hydroxycarbam-oyl-heptanoylamino)-phenyl]-propionic acid (2)

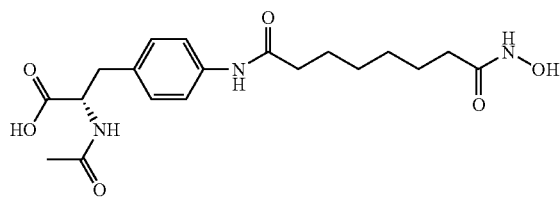

Stage 6 resin loaded with Compound 1 (0.3 g, 1.14 mmol/g) was treated with sodium hydroxide (0.068 g), in water (2 ml, 0.85 M) and the reaction shaken for 4 hrs. The resin was washed, DCM, DMF (×2), DCM, MeOH (×2), MeOH, TBME and dried. The required product was cleaved with 2% TFA/DCM to give crude compound 2, which was further purified by preparative HPLC. m/z 394 [M$^+$+H]$^+$, $^1$H NMR (400 MHz, d4-MeOH) δ: 1.39-1.44 (4H, m, 2×CH$_2$), 1.63-1.71 (4H, m, 2×CH$_2$), 1.90 (3H, s, CH$_3$CO), 2.11 (2H, t, CH$_2$), 2.37 (2 H, t, CH$_2$), 2.92 (1 H, dd, ArCH), 3.17 (1 H, dd, ArCH), 4.65 (1 H, q, NHCH), 7.19 (2 H, 2 d, Ar), 7.48 (2 H, d, Ar).

The analogous enantiomers (R)-2-Acetylamino-3-[4-(7-hydroxycarbamoyl-heptanoylamino)-phenyl]-propionic acid cyclopentyl ester (3) and (R)-2-Acetylamino-3-[4(7-hydroxycarbamoyl-heptanoylamino)-phenyl]-propionic acid (4) were prepared as Above.

Synthesis of Compound (5) and Compound (6)

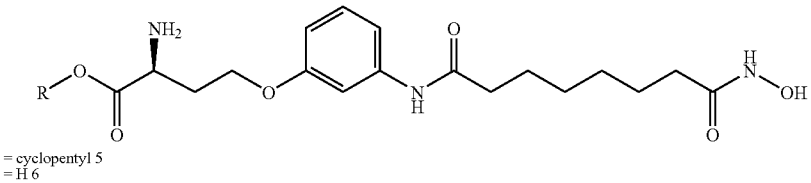

R = cyclopentyl 5
R = H 6

Stage 1: (S)-2-tert-Butoxycarbonylamino-4-(3-nitro-phenoxy)-butyric acid cyclopentyl ester

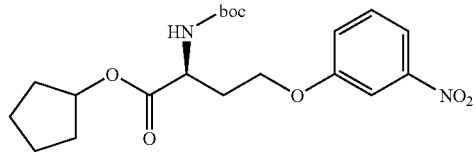

To a slurry of 3-nitrophenol (1.2 g, 8.4 mmol) in anhydrous DCM (60 ml) at 0° C. was added (S)-2-tert-butoxycarbonylamino-4-hydroxy-butyric acid cyclopentyl ester (2 g, 7 mmol) (see Scheme 9) in DCM (10 ml), triphenyl phosphine (7.5 g, 28.7 mmol) followed by slow addition of DIAD (5.8 g, 28.7 mmol). The reaction was allowed to warm to room temperature and stirred for 16 h. The solvent was removed and the crude material purified by column chromatography. (EtOAc:heptane, 1:9), (1.6 g, 56%). LCMS purity 95%, m/z 309 [M$^+$+H-boc]$^+$.

Stage 2: (S)-4-(3-Amino-phenoxy)-2-tert-butoxycar-bonylamino-butyric acid cyclopentyl ester

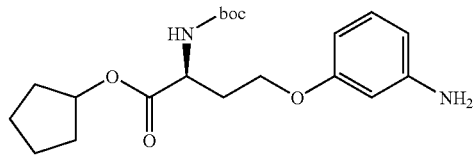

Stage 1 nitro analogue (1.5 g, 3.7 mmol) was dissolved in ethanol (50 ml) before addition of Pd/carbon (200 mg). The reaction was stirred under an atmosphere of hydrogen (balloon pressure) for 16 h at room temperature. The reaction mixture was filtered through a pad of celite and the solvent removed to give the required product 1.3 g (94% yield). LCMS purity 91%, m/z 379 [M$^+$+H]$^+$.

Stage 3: Resin Loading

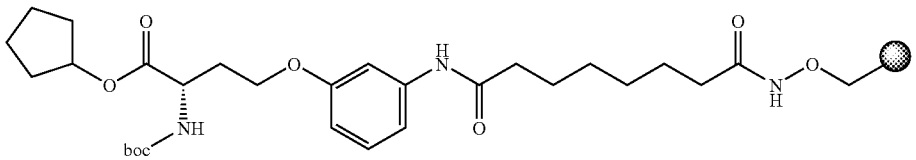

Suberic acid derivatised hydroxylamine 2-chlorotrityl resin (see stages 4-5 above) (1.5 g, loading, 0.94 mmol/g) was swollen in DCM/DMF (1:1, 40 ml). PyBOP (1.8 g, 3.44 mmol) and diisopropyl ethylamine (2.5 ml, 14.1 mmol) were added. (S)-4-(3-Amino-phenoxy)-2-tert-butoxycarbony-lamino-butyric acid cyclopentyl ester (Scheme 9) (1.03 g, 3.44 mmol) pre-dissolved in DMF (40 ml) was then added and the reaction shaken for 2 days followed by filtration, standard wash of resin and air drying.

Stage 4: (S)-2-Amino-4-[3-(7-hydroxycarbamoyl-heptanoylamino)-phenoxy]-butyric acid cyclopentyl ester (5)

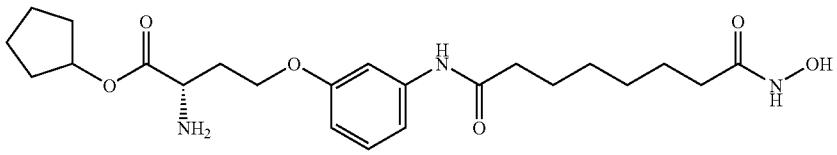

Stage 3 resin (600 mg) was cleaved with 2% TFA/DCM (10 ml) for 10 minutes before filtering the resin and evaporating the filtrate under reduced pressure. The process was repeated (×3). The residue was re-suspended in 20% TFA/DCM and allowed to stand for 30 minutes to fully remove the boc group before purification by preparative HPLC to give Compound 5 (28.7 mg) LCMS purity 95%, m/z 450 [M$^+$+H]$^+$, $^1$H NMR (400 MHz, MeOD), δ: 1.35-1.45 (4 H, m, alkyl), 1.55-1.85 (10 H, m, alkyl), 1.90 (2 H, m, CH$_2$), 2.10 (2 H, t, CH$_2$) 2.40 (4 H, m, 2×CH$_2$), 4.20 (3 H, 2×t, CH$_2$+CH), 5.35 (1 H, m, CH), 6.70 (1 H, d, Ar), 6.95 (1 H, d, Ar), 7.25 (1 H, t, Ar), 7.50 (1 H, s, Ar)

Stage 5: (S)-2-Amino-4-[3-(7-hydroxycarbamoyl-heptanoylamino)-phenoxy]-butyric acid (6)

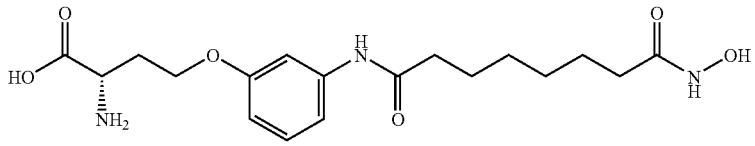

Stage 3 resin (500 mg) was swollen in THF (15 ml) and aqueous 2M NaOH (1.2 ml) added. The reaction was shaken at room temperature for 16 h. The resin was subjected to standard wash and dried. The resin was cleaved with 2% TFA/DCM (10 ml) for 10 minutes before filtering the resin and evaporating the filtrate under reduced pressure. The process was repeated three times. The residue was re-suspended in 20% TFA/DCM and allowed to stand for 30 minutes to fully remove the boc group and following evaporation Compound 6 (25.3 mg) was obtained by preparative HPLC purification. LCMS purity 95%, m/z 382 [M$^+$+H]$^+$, $^1$H NMR (400 MHz, MeOD), δ: 1.35-1.45 (4 H, m, alkyl), 1.60-1.80 (4 H, m, alkyl), 2.10 (2 H, t, CH$_2$) 2.40 (3 H, t+m, CH$_2$+CH), 2.45 (1 H, m, alkyl), 4.25 (3 H, m, CH$_2$+CH), 6.75 (1H, d, Ar), 6.95 (1 H, d, Ar), 7.25 (1 H, t, Ar), 7.45 (1 H, s, Ar).

Synthesis of Compound (7) and Compound (8)

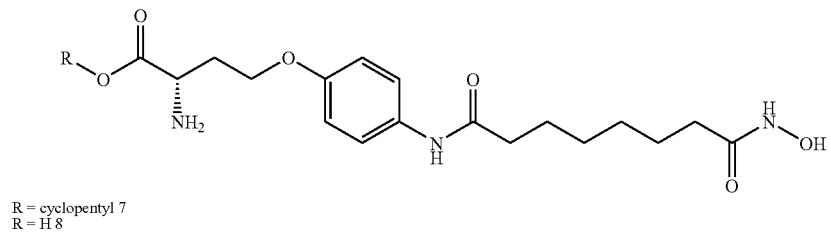

R = cyclopentyl 7
R = H 8

Stage 1: (S)-2-tert-Butoxycarbonylamino-4-(4-nitro-phenoxy)-butyric acid cyclopentyl ester

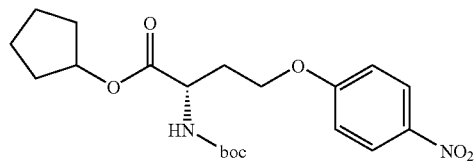

To a slurry of 4 nitrophenol (0.32 g, 2.3 mmol) in anhydrous DCM (100 ml) at 0° C. was added (S)-2-tert-butoxycarbonylamino-4-hydroxy-butyric acid cyclopentyl ester (1 g, 3.5 mmol) (Scheme 9) in DCM (100 ml), triphenyl phosphine (2.5 g, 9.5 mmol) followed by slow addition of DIAD (1.9 ml, 9.6 mmol). The reaction was allowed to warm to room temperature and stirred for 16 h. The solvent was removed and the crude material purified by column chromatography to furnish the desired product. (EtOAc:heptane, 1:9), (0.45 g, 48%). LCMS purity 97%, m/z 309 [M$^+$+H-boc]$^+$.

Stage 2: (S)-4-(3-Amino-phenoxy)-2-tert-butoxycarbonylamino-butyric acid cyclopentyl ester

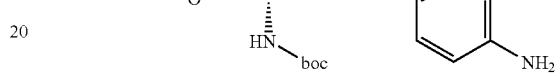

Stage 1 nitro analogue (90 mg, 0.22 mmol) was dissolved in ethanol (10 ml) before addition of Pd/carbon (20 mg). The reaction was stirred under an atmosphere of hydrogen (balloon pressure) for 16 h at room temperature. The reaction mixture was filtered through a pad of celite and the solvent removed to give the required product (85 mg, 100%). LCMS purity 92%, m/z 279 [M$^+$+H-boc]$^+$.

Stage 3: Resin Loading

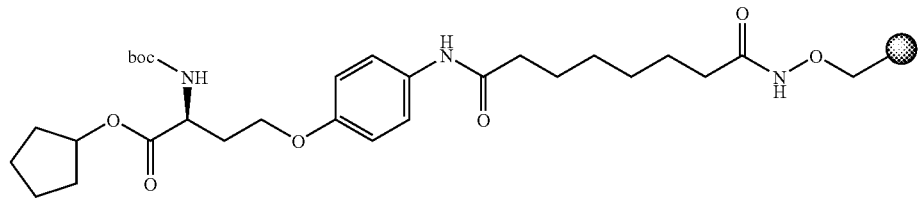

[1]Suberic acid derivatised hydroxylamine 2-chlorotrityl resin (790 mg, loading 0.94 mmol/g) was swollen in DCM/DMF (1:1, 30 ml). PyBOP (1.16 g, 2.23 mmol) and diisopropylethylamine (0.9 ml, 5.17 mmol) were added. (S)-4-(3-Amino-phenoxy)-2-tert-butoxycarbonylamino-butyric acid cyclopentyl ester (Scheme 9) (420 mg, 1.11 mmol) dissolved in DCM/DMF (1:1, 4 ml) was added and the reaction shaken for 6 days before filtration and standard wash of resin which was dried under air.

[1] See stages 4-5, compound 1

Stage 4: (S)-2-Amino-4-[4-(7-hydroxycarbamoyl-heptanoylamino)-phenoxy]-butyric acid cyclopentyl ester (7)

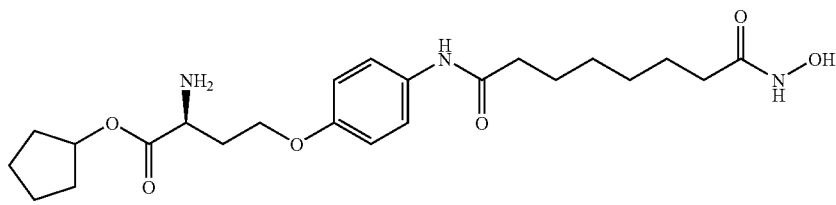

Stage 3 resin (160 mg) was cleaved with 2% TFA/DCM (5 ml) for 10 minutes before filtering the resin and evaporating the filtrate under reduced pressure. The process was repeated (×3). The residue was re-suspended in 20% TFA/DCM and stood for 30 minutes to fully remove the boc group and the residue purified by preparative HPLC to give Compound 7 (25.2 mg). LCMS purity 100%, m/z 450 [M+ +H]+, $^1$H NMR (400 MHz, MeOD), δ: 1.54-1.56 (4 H, m, alkyl), 1.79-1.87 (10 H, m, alkyl), 2.05 (2 H, m, CH$_2$), 2.25 (2 H, t, J=7.6 Hz, CH$_2$) 2.50 (4 H, m, 2×CH$_2$), 4.32 (2 H, t, J=5.6 Hz, CH$_2$), 4.38 (1 H, t, J=6.5 Hz, CH), 5.48 (1 H, m, CH), 7.07 (2 H, d, J=9.1 Hz Ar), 7.61 (2 H, d, J=9 Hz, Ar)

Stage 5: (S)-2-Amino-4-[4-(7-hydroxycarbamoyl-heptanoylamino)-phenoxy]-butyric Acid (8)

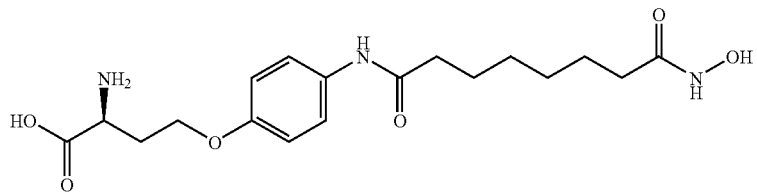

Stage 3 resin (580 mg) was swollen in THF/MeOH (1:1, 4 ml) and aqueous 2M NaOH (2 ml) added. The reaction was shaken at room temperature for 16 h. The resin was subjected to standard wash and dried. The resin was cleaved with 2% TFA/DCM (10 ml) for 10 minutes before filtering the resin and evaporating the filtrate under reduced pressure. The process was repeated (×3). The residue was re-suspended in 20% TFA/DCM and allowed to stand for 30 minutes to fully remove the boc group and following evaporation Compound 8 (17.1 mg) was obtained by preparative HPLC. LCMS purity 92%, m/z 382 [M+ +H]+, $^1$H NMR (400 MHz, MeOD), δ: 1.40-1.5 (4 H, m, alkyl), 1.60-1.80 (4 H, m, alkyl), 2.12 (2 H, t, J=11.5 Hz, CH$_2$), 2.40 (4 H, m, 2×CH$_2$), 4.20 (3 H, m, CH$_2$+CH), 7.94 (2 H, d, J=14.4 Hz, Ar), 7.61 (2 H, d, J=14.6 Hz, Ar)

Synthesis of the Compounds in FIG. 2 Exemplified by: Compound (9) and Compound (10)

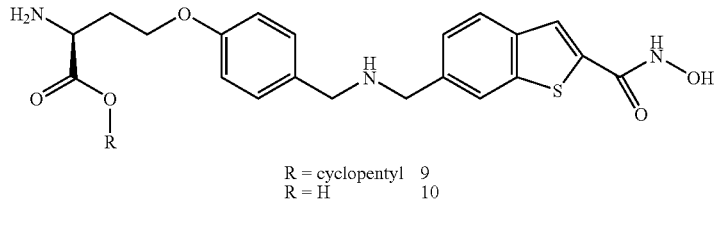

Figure 2

R = cyclopentyl 9
R = H 10

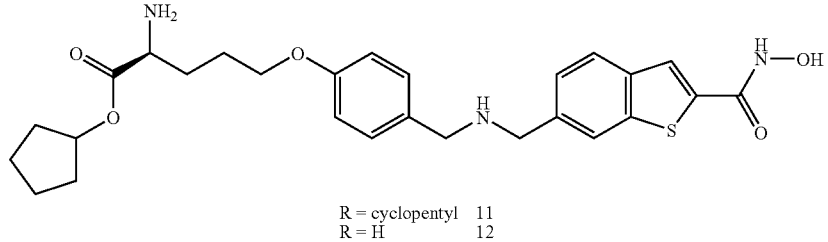

R = cyclopentyl 11
R = H 12

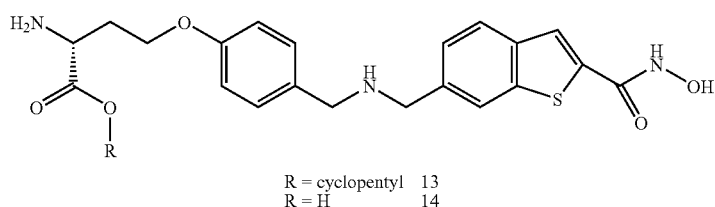

R = cyclopentyl 13
R = H 14

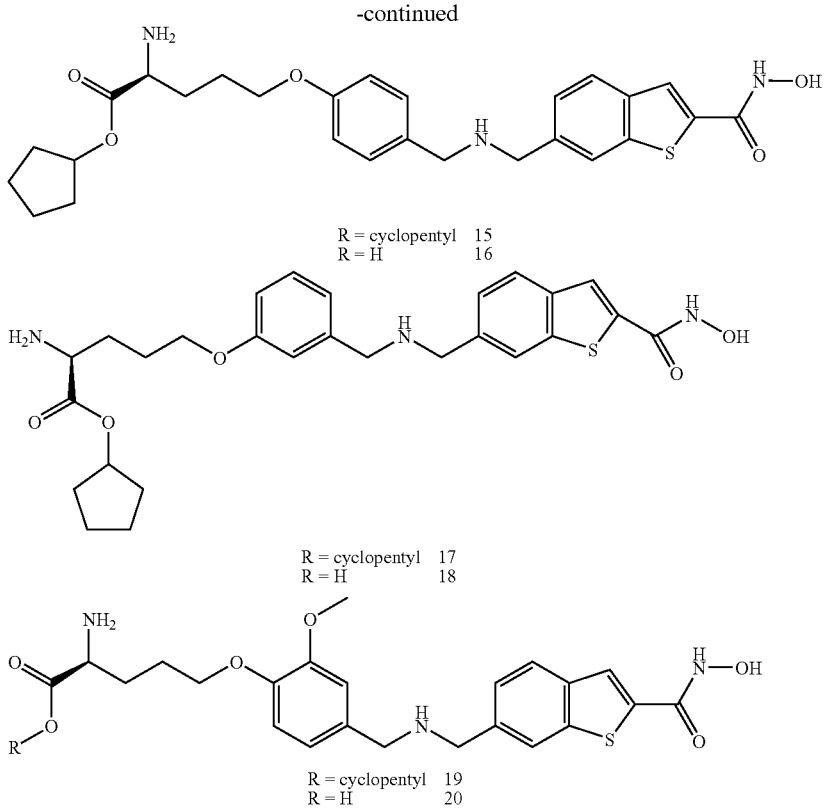

R = cyclopentyl 15
R = H 16

R = cyclopentyl 17
R = H 18

R = cyclopentyl 19
R = H 20

Stage 1: (4-Hydroxybenzyl)-carbamic acid benzyl ester

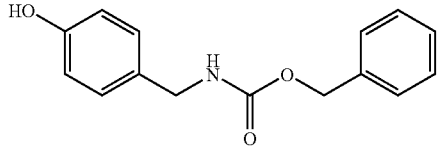

To a stirred solution of 4-aminomethylphenol (1 g, 8.13 mmol) in tetrahydrofuran/water (1:1 ratio, 20 ml) at 0° C. was added solid NaHCO$_3$ (0.888 g, 10.16 mmol) followed by dropwise addition of benzyl chloroformate (1.16 ml, 8.13 mmol). The mixture was stirred at 0° C. for 10 minutes then allowed to warm slowly to r.t. After stirring the mixture for 90 minutes the tetrahydrofuran was removed in vacuo. The aqueous layer was extracted with EtOAc (2×10 ml). The organic layer was washed with water (2×10 ml), dried (MgSO$_4$), and the solvent removed in vacuo to a residue. Trituration with heptane gave the product as a white solid (2.10 g, 100% yield). LCMS purity 100%, m/z 258 [M$^+$+H]$^-$.

Stage 2: (S)-4-[4-Benzyloxycarbonylaminomethyl)-phenoxy]-2-tert-butoxycarbony-lamino-butyric acid cyclopentyl ester

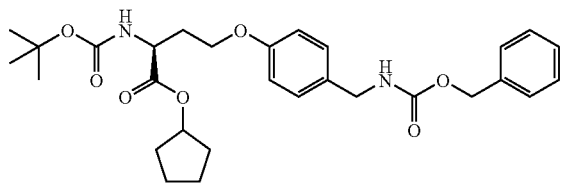

To a stirred solution of (4-hydroxybenzyl)-carbamic acid benzyl ester (0.164 g, 0.64 mmol) in DMF (10 ml) was added potassium carbonate (0.113 g, 0.82 mmol) and (S)-4-Bromo-2-tert-butoxycarbonylamino-butyric acid cyclopentyl ester (Scheme 9) (0.25 g, 0.71 mmol). The mixture was heated at 50° C. for 18 hours, cooled and the solvent removed in vacuo. The residue was partitioned (EtOAc/water [10 ml/10 ml]), the organic layer was washed with water (2×10 ml), dried (MgSO$_4$), and the solvent removed in vacuo. Purification by column chromatography (1:1 EtOAc/heptane) gave the product as a colourless oil (0.290 g, 78% yield). LCMS purity 100%, m/z 549 [M$^+$+Na]$^+$.

Stage 3: (S)-4-(4-Aminomethyl-phenoxy)-2-tert-butoxycarbonylamino-butyric acid cyclopentyl ester

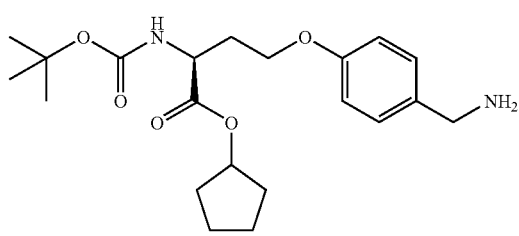

To a stirred solution of (S)-4-[4-benzyloxycarbonylaminomethyl)-phenoxy]-2-tert-butoxycarbonylamino-butyric acid cyclopentyl ester (0.21 g, 0.40 mmol) in EtOAc (5 ml) was added palladium on carbon (10% w/w, 40 mg). The reaction was put under a hydrogen atmosphere for 2 hours. Filtration of the reaction through Celite and removal of the solvent in vacuo gave the product as a colourless oil (156 mg, 100% yield). LCMS purity 100%, m/z 393 [M$^+$+H]$^+$.

Stage 4: (S)-2-Amino-4-(4-{[(2-hydroxycarbamoyl-benzo[b]thiophen-6-ylmethyl)-amino]-methyl}-phenoxy)-butyric acid cyclopentyl ester (9)

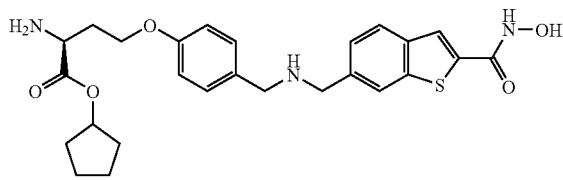

To a stirred solution of 6-formyl-benzo[b]thiophene-2-carboxylic acid (1-isobutoxy-ethoxy) amide (Scheme 13) (0.128 g, 0.40 mmol) in DCE (5 ml) was added (S)-4-(4-aminomethyl-phenoxy)-2-tert-butoxycarbonylamino-butyric acid cyclopentyl ester (0.156 g, 0.40 mmol) followed by sodium triacetoxyborohydride (0.253 g, 1.1 g mmol) and glacial acetic acid (0.023 ml, 0.40 mmol). After stirring for 18 hours the mixture was quenched using saturated aqueous NaHCO$_3$ solution (5 ml). The organic layer was separated, washed further with saturated aqueous NaHCO$_3$ solution (2×5 ml), dried (MgSO$_4$) and the solvent removed in vacuo to give a yellow residue. The residue was redissolved in a TFA/DCM solution (1:1, 5 ml). After stirring the solution for 45 minutes the solvent was removed in vacuo. Purification by preparative HPLC gave the product as a white solid (0.030 g, 15% yield). LCMS purity 96.1%, m/z 498 [M$^+$+H]$^+$, $^1$H NMR (300 MHz, DMSO), δ: 1.50-1.90 (9H, m, CH$_2$×4, CH), 2.25 (2H, m, CH$_2$), 4.10-4.40 (7H, m, CH$_2$×3, CH), 5.20 (1H, m, CH), 6.95 (2H, d, ArH×2, J=8.6 Hz), 7.45 (2H, d, ArH×2, J=8.6 Hz), 7.55 (1H, d, ArH, J=7.8 Hz), 8.00 (2H, m, ArH×2), 8.15 (1H, s, ArH), 8.40 (2H, br s, ArH×2), 9.20 (2H, m ArH×2).

Stage 5: (S)-2-Amino-4-(4-{[(2-hydroxycarbamoyl-benzo[b]thiophen-6-ylmethyl)-amino]-methyl}-phenoxy)-butyric acid (10)

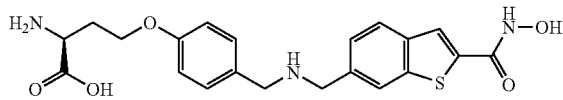

To a stirred solution of (S)-2-Amino-4-(4-{[(2-hydroxycarbamoyl-benzo[b]thiophen-6-ylmethyl)-amino]-methyl}-phenoxy)-butyric acid cyclopentyl ester (0.043 g, 0.086 mmol) in tetrahydrofuran/water (4 ml/1 ml) was added lithium hydroxide (0.006 g, 0.26 mmol). The mixture was heated at 45° C. for 2 hours. The solvent was removed in vacuo to give a white residue. Purification by preparative HPLC gave the product as a pink solid (0.020 g, 54% yield). LCMS purity 85.7%, m/z 430 [M$^+$+H]$^+$, $^1$H NMR (300 MHz, DMSO), δ: 2.00-2.20 (2H, m, CH$_2$), 3.45 (1H, m, CH), 4.15 (4H, m, CH$_2$×2), 6.95 (2H, d, ArH×2, J=8.4 Hz), 7.40 (2H, d, ArH×2, J=8.4 Hz), 7.50 (1H, d, ArH, J=7.6 Hz), 7.95 (2H, m, ArH×2), 8.05 (1H, br s, ArH).

The following compounds were prepared in a similar manner to Compound (9) and Compound (10) using the appropriate intermediates (see Schemes 9, 10 and 13) and commercial materials.

(S)-2-Amino-5-(4-{[(2-hydroxycarbamoyl-benzo[b]thiophen-6-ylmethyl)-amino]-methyl}-phenoxy)-pentanoic acid cyclopentyl ester (11)

LCMS purity 96.1%, m/z 512 [M$^+$+H]$^+$, $^1$H NMR (300 MHz, DMSO), δ: 1.50-1.90 (9H, m, CH$_2$×4, CH), 4.00-4.40 (6H, m, CH$_2$×3), 5.20 (1H, m, CH), 7.00 (2H, d, ArH×2, J=8.5 Hz), 7.40 (2H, d, ArH×2, J=8.5 Hz), 7.55 (1H, d, ArH, J=7.6 Hz), 8.00 (2H, m, ArH×2), 8.15 (1H, s, ArH), 8.35 (2H, br s, ArH×2), 9.20 (2H, m ArH×2).

(S)-2-Amino-5-(4-{[(2-hydroxycarbamoyl-benzo[b]thiophen-6-ylmethyl)-amino]-methyl}-phenoxy)-pentanoic acid (12)

LCMS purity 86.1%, m/z 444 [M$^+$+H]$^+$, $^1$H NMR (300 MHz, DMSO), δ: 1.80 (4H, m, CH$_2$×2), 3.45 (1H, m, CH), 3.95 (4H, m, CH$_2$×2), 4.15 (2H, m, CH$_2$), 6.95 (2H, d, ArH×2, J=8.6 Hz)), 7.40 (3H, m, ArH×3), 8.00 (3H, m, ArH×3).

(R)-2-Amino-4-(4-{[(2-hydroxycarbamoyl-benzo[b]thiophen-6-ylmethyl)-amino]-methyl}phenoxy)-butyric acid cyclopentyl ester (13)

LCMS purity 97.9%, m/z 498 [M$^+$+H]$^+$, $^1$H NMR (300 MHz, MeOD), δ: 1.65-2.00 (9H, m, CH$_2$×4, CH), 2.40 (1H, m, CH), 4.17-4.28 (4H, m, CH$_2$×2), 4.38 (2H, s, CH$_2$), 4.85 (2H, s, CH$_2$), 4.98 (2H, s, CH$_2$), 5.28-5.37 (1H, m, ArH), 7.07 (2H, d, ArH×2, J=8.7 Hz), 7.47 (2H, d, ArH×2, J=8.7 Hz), 7.53 (1H, dd, ArH, J=8.3, 1.5 Hz), 7.90 (1H, s, ArH), 7.98-8.07 (2H, m, ArH×2).

(S)-2-Amino-4-(4-{[(2-hydroxycarbamoyl-benzo[b]thiophen-6-ylmethyl)-amino]-methyl}-phenoxy)-butyric acid (14)

LCMS purity 100.0%, m/z 430 [M$^+$+H]$^+$, $^1$H NMR (300 MHz, MeOD), δ: 2.15-2.44 (2H, m, CH$_2$), 3.97 (1H, t, CH, J=6.2 Hz), 4.05-4.21 (4H, m, CH$_2$×2), 4.60 (2H, s, CH$_2$), 6.96 (2H, d, ArH×2, J=8.7 Hz), 7.33 (2H, d, ArH×2, J=8.5 Hz), 7.42 (1H, d, ArH, J=8.3 Hz), 7.77 (1H, s, ArH), 7.89 (1H, d, ArH, J=8.1 Hz), 7.95 (1H, s, ArH).

(R)-2-Amino-5-(4-{[(2-hydroxycarbamoyl-benzo[b]thiophen-6-ylmethyl)-amino]-methyl}-phenoxy)-pentanoic acid cyclopentyl ester (15)

LCMS purity 100.0%, m/z 512 [M$^+$+H]$^+$, $^1$H NMR (300 MHz, MeOD), δ: 1.62-2.01 (12H, m, CH$_2$×6), 3.97 (3H, m, CH$_2$, CH), 4.13 (2H, s, CH$_2$), 4.27 (2H, s, CH$_2$), 5.20 (1H, m, CH), 6.90 (2H, d, ArH×2, J=8.6 Hz), 7.34 (2H, d, ArH×2, J=8.6 Hz), 7.55 (1H, dd, ArH, J=8.3, 0.8 Hz), 7.77 (1H, s, ArH), 7.89 (1H, d, ArH, J=8.3 Hz), 7.96 (1H, s, ArH).

(R)-2-Amino-5-(4-{[(2-hydroxycarbamoyl-benzo[b]thiophen-6-ylmethyl)-amino]-methyl}-phenoxy)-pentanoic acid (16)

LCMS purity 95.0%, m/z 444 [M$^+$+H]$^+$, $^1$H NMR (300 MHz, MeOD), δ: 2.01-2.10 (4H, m, CH$_2$×2), 4.05 (3H, m, CH$_2$, CH), 4.24 (2H, s, CH$_2$), 4.38 (2H, s, CH$_2$), 7.04 (2H, d, ArH×2, J=8.7 Hz), 7.44 (2H, d, ArH×2, J=8.5 Hz), 7.53 (1H, dd, ArH, J=8.2, 1.4 Hz), 8.01 (1H, d, ArH, J=8.2 Hz), 8.06 (1H, s, ArH).

(S)-2-Amino-5-(4-{[(2-hydroxycarbamoyl-benzo[b]thiophen-6-ylmethyl)-amino]-methyl}-phenoxy)-pentanoic acid cyclopentyl ester (17)

LCMS purity 94.0%, m/z 512 [M$^+$+H]$^+$, $^1$H NMR (300 MHz, MeOD), δ: 1.31-2.09 (14H, m, CH$_2$×7), 4.08 (3H, m+d, J=5.5 Hz, CH$_2$, CH), 4.27 (2H, s, CH$_2$), 4.40 (1H, s, CH), 5.32 (1H, m, CH), 7.04 (3H, m, ArH×3), 7.39 (1H, t, J=7.7 Hz, ArH), 7.55 (1H, d, J=7.7 Hz, ArH), 7.88 (1H, s, ArH), 7.99 (1H, d J=7.8 Hz, ArH), 8.07 (1H, s, ArH).

(S)-2-Amino-5-(4-{[(2-hydroxycarbamoyl-benzo[b]thiophen-6-ylmethyl)-amino]-methyl}-phenoxy)-pentanoic acid (18)

LCMS purity 100.0%, m/z 444 [M$^+$+H]$^+$, $^1$H NMR (300 MHz, MeOD), δ: 1.97-2.41 (4H, m, CH$_2$×2), 4.06 (3H, m, CH$_2$, CH), 4.26 (2H, s, CH$_2$), 4.40 (2H, s, CH$_2$), 7.04 (3H, m, ArH×3), 7.39 (1H, t, J=7.6 Hz, ArH), 7.55 (1H, d, J=7.5 Hz, ArH), 7.88 (1H, s, ArH), 7.98 (1H, d, J=7.8 Hz, ArH), 8.07 (1H, s, ArH).

(S)-2-Amino-5-(4-{[(2-hydroxycarbamoyl-benzo[b]thiophen-6-ylmethyl)-amino]-methyl}-2-methoxyphenoxy)-pentanoic acid cyclopentyl ester (19)

LCMS purity 85.9%, m/z 542 [M$^+$+H]$^+$, $^1$H NMR (300 MHz, MeOD), δ: 1.61-2.26 (12H, m, CH$_2$×6), 3.85-3.91 (3H, m, CH$_2$, CH), 4.04-4.18 (3H, m, CH$_2$, CH), 4.23 (2H, s, CH$_2$), 4.34-4.39 (2H, m, CH$_2$), 5.27-5.36 (1H, m, CH), 6.98-7.16 (2H, m, ArH×2), 7.49-7.72 (2H, m, ArH×2), 7.83-8.07 (3H, m, ArH×3).

(S)-2-Amino-5-(4-{[(2-hydroxycarbamoyl-benzo[b]thiophen-6-ylmethyl)-amino]-methyl}-2-methoxyphenoxy)-pentanoic acid (20)

LCMS purity 86.4%, m/z 474 [M$^+$+H]$^+$, $^1$H NMR (300 MHz, MeOD), δ: 1.88-2.32 (4H, m, CH$_2$×2), 3.85-3.92 (3H, m, CH$_2$, CH), 4.05-4.17 (3H, m, CH$_2$, CH), 4.25 (2H, s, CH$_2$), 4.35-4.42 (2H, m, CH$_2$), 7.01-7.09 (2H, m, ArH×2), 7.13 (1 H, s, ArH), 7.54 (1H, dd, ArH, J=8.3, 1.5 Hz), 7.88 (1H, s, ArH), 8.00 (1H, d, ArH, J=8.3 Hz), 8.06 (1H, s, ArH).

Synthesis of Compound (21)

Stage 1: (S)-2-Amino-5-[4-benzyloxycarbonylaminomethyl)-phenoxy]-pentanoic acid cyclopentyl ester

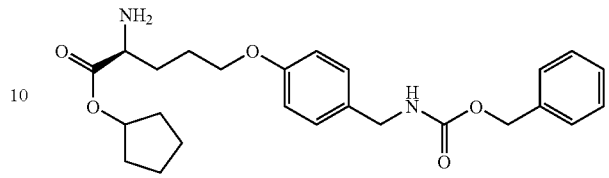

(S)-5-[4-Benzyloxycarbonylaminomethyl)-phenoxy]-2-tert-butoxycarbonylamino-pentanoic acid cyclopentyl ester (Compound (11), Stage 2) (0.150 g, 0.28 mmol) was dissolved in a TFA/DCM solution (1:1, 4 ml). The solution was stirred for 1 hour then the solvent was removed in vacuo. The resultant residue was dissolved in EtOAc (10 ml), washed with saturated aqueous NaHCO$_3$ solution (3×5 ml), dried (MgSO$_4$) and the solvent removed in vacuo to give a colourless oil (0.100 g, 82% yield). LCMS purity 100%, m/z 441 [M$^+$+H]$^+$.

Stage 2: (S)-2-Acetylamino-5-[4-benzyloxycarbonylaminomethyl)-phenoxy]-pentanoic acid cyclopentyl ester

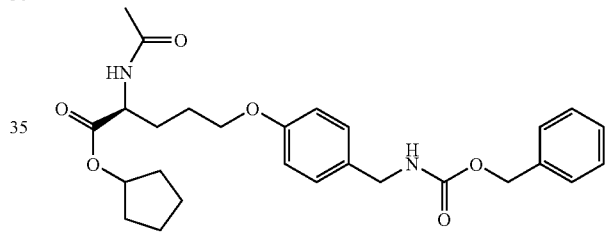

To a stirred solution of (S)-2-Amino-5-[4-benzyloxycarbonylaminomethyl)-phenoxy]-pentanoic acid cyclopentyl ester (0.100 g, 0.23 mmol) in DCM (5 ml) at 0° C. was added triethylamine (0.064 ml, 0.45 mmol) followed by dropwise addition of acetyl chloride (0.024 ml, 0.34 mmol). After stirring the mixture at r.t. for 2 hours, the reaction was quenched with water (5 ml). The organic layer was separated, dried (MgSO$_4$), and the solvent removed in vacuo to give a residue. Purification by column chromatography (EtOAc) gave the product as an oil (62 mg, 57% yield). LCMS purity 100%, m/z 483 [M$^+$+H]$^+$.

This intermediate was processed through the stages 2-4 as shown for compound 9.

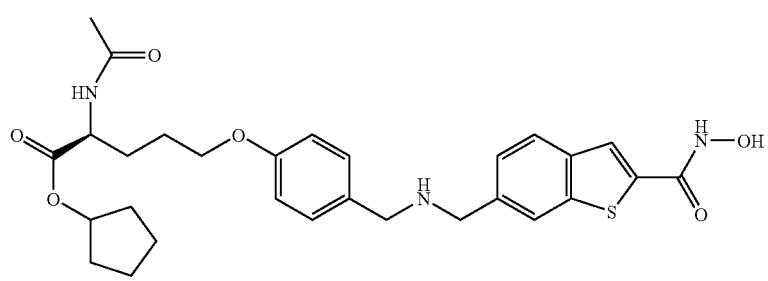

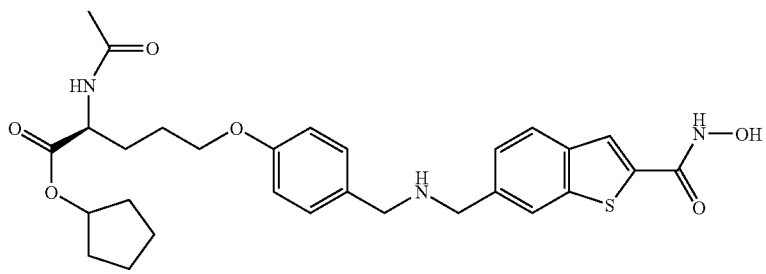

(S)-2-Acetylamino-5-(4-{[(2-hydroxycarbamoyl-benzo[b]thiophen-6-ylmethyl)-amino]-methyl}-phenoxy)-pentanoic acid cyclopentyl ester (21)

LCMS purity 100.0%, m/z 554 [M$^+$+H]$^+$, $^1$H NMR (300 MHz, MeOD), δ: 1.42-1.97 (16H, m, CH$_3$, CH$_2$×6, CH), 3.93 (2H, t, CH$_2$), 4.11 (2H, s, CH$_2$), 4.21-4.33 (3H, m, CH$_2$, CH), 5.03-5.11 (1H, m, CH), 6.90 (2H, d, ArH×2, J=8.7 Hz), 7.30 (2H, d, J=8.7 Hz, ArH×2), 7.42 (1H, dd, J=8.3, 1.5 Hz, ArH), 7.77 (1H, s, ArH), 7.89 (1H, d, J=8.3 Hz, ArH), 7.95 (1H, s, ArH), 8.29 (1H, d, ArH, J=7.5 Hz).

Synthesis of Compound (22) and Compound (23)

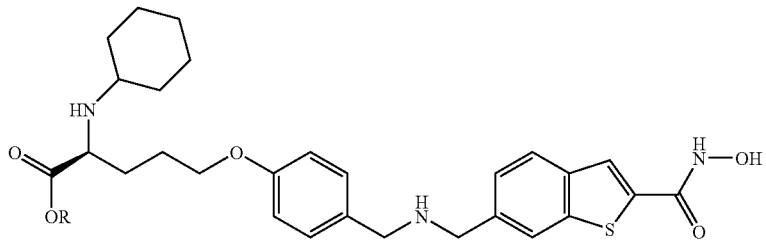

R = cyclopentyl 22
R = H 23

Stage 2: (S)-4-[4-Benzyloxycarbonylaminomethyl)-phenoxy]-2-cyclohexylamino-pentanoic acid cyclopentyl ester

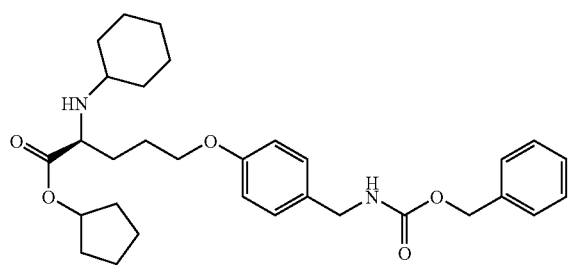

To a stirred solution of (S)-2-Amino-4-[4-benzyloxycarbonylaminomethyl)-phenoxy]-pentanoic acid cyclopentyl ester (Stage 1, Compound 21) (0.452 g, 1.03 mmol) in DCE (6 ml) was added cyclohexanone (0.082 g, 0.79 mmol) followed by sodium triacetoxyborohydride (0.653 g, 2.37 mmol) and glacial acetic acid (0.068 ml, 0.79 mmol). After stirring for 1 hour the mixture was quenched using saturated aqueous NaHCO$_3$ solution (5 ml). The organic layer was separated, washed further with saturated aqueous NaHCO$_3$ solution (2×5 ml), dried (MgSO$_4$) and the solvent removed in vacuo to give a yellow residue. Purification by column chromatography (1:1 EtOAc/heptane) gave the product as an oil (0.331 g, 62% yield). LCMS purity 96.1%, m/z 523 [M$^+$+H]$^+$.

This intermediate was processed through Stages 2-4 as shown for Compound 9.

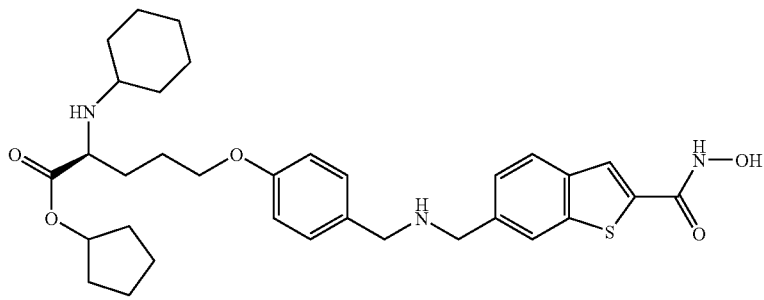

(S)-2-Cyclohexylamino-S-(4-{[(2-hydroxycarbam-oyl-benzo[b]thiophen-6-ylmethyl)-amino]-methyl}-phenoxy)-pentanoic acid cyclopentyl ester (22)

LCMS purity 100.0%, m/z 594 [M$^+$+H]$^+$, $^1$H NMR (300 MHz, MeOD), δ: 1.13-1.48 (6H, m, CH×6), 1.55-2.26 (19H, m CH$_3$, CH$_2$×8), 4.09 (1H, t, CH, J=5.5 Hz), 4.21-4.29 (2H, m, CH$_2$), 4.38 (2H, s, CH$_2$), 5.32-5.40 (1H, m, CH), 7.02 (2H, d, ArH×2, J=8.9 Hz), 7.44 (1H, d, J=8.5 Hz, ArH), 7.53 (1H, d, J=8.7 Hz, ArH), 7.88 (1H, s, ArH), 7.96-8.06 (2H, m, ArH×2).

(S)-2-Cyclohexylamino-5-(4-{[(2-hydroxycarbam-oyl-benzo[b]thiophen-6-ylmethyl)-amino]-methyl}-phenoxy)-pentanoic acid (23)

Compound 23 was prepared by the hydrolysis of Compound 22 (see Stage 5, Compound 9) LCMS purity 96.2%, m/z 526 [M$^+$+H]$^+$, $^1$H NMR (300 MHz, DMSO), δ: 0.95-2.14 (15H, m, CH$_2$×7, CH), 2.88-3.08 (2H, m, CH$_2$), 3.99-4.06 (1H, m, CH), 4.09-4.17 (2H, m, CH$_2$), 4.22-4.31 (2H, m, CH$_2$), 6.99 (2H, d, ArH×2, J=10.0 Hz), 7.51-7.62 (1H, m, ArH), 7.89-8.09 (2H, m, ArH×2), 8.14 (1H, s, ArH), 9.34 (2H, br s, ArH×2).

Synthesis of the Compounds in FIG. 3 Exemplified by: Compound (24) and Compound (25)

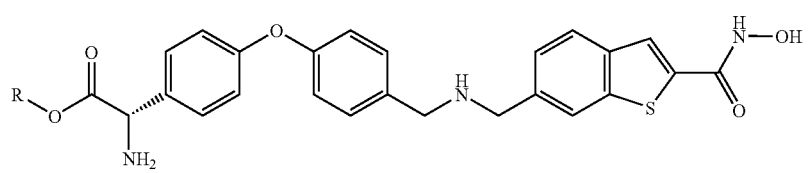

Figure 3

R = cyclopentyl 24
R = H 25

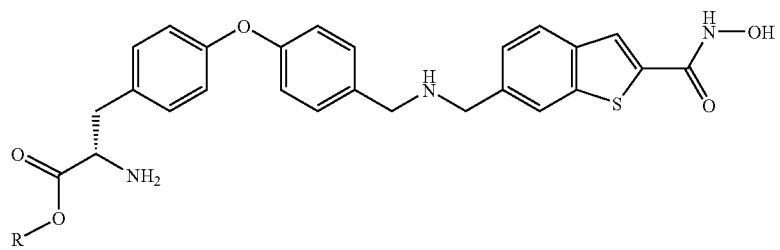

R = cyclopentyl 26
R = H 27

Stage 1: (4-Bromo-benzyl)-carbamic acid benzyl ester

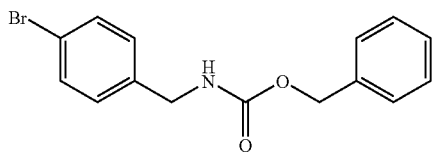

A solution of 4-bromobenzylamine (5 g, 26.9 mmol) in THF (50 ml) and water (50 ml) was cooled down to 0° C. with sodium hydroxide (1.13 g, 28.2 mmol). Benzyl chloroformate (4.0 ml, 28.2 mmol) was added slowly and the reaction mixture was stirred at 0° C. for 1 h and at r.t. for 18 hours. Brine (50 ml) and EtOAc (50 mL) were added and the phases were separated. The aqueous phase was extracted with EtOAc (40 mL). The organic phase was dried over magnesium sulfate, filtered and concentrated to dryness to yield a light pink solid (9.27 g, 100%). $^1$H NMR (300 MHz, CDCl$_3$), δ: 4.34 (2 H, d, J=6.0 Hz, CH$_2$NH), 5.14 (2 H, s, OCH$_2$), 7.17 (2 H, d, J=8.1 Hz, Ar), 7.33-7.40 (5 H, m, Ar), 7.46 (2 H, d, J=8.3 Hz, Ar)

Stage 2: α-Benzyloxycarbonylamino-p-toluoylboronic acid

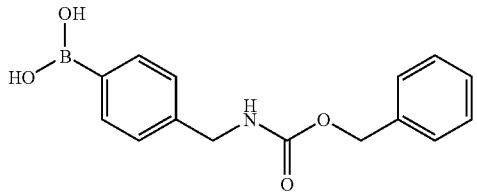

Stage 1 bromo compound (5 g, 15.6 mmol) was dissolved in anhydrous THF (50 ml) and cooled down to −78° C. n-BuLi 2.5M in hexane (12.5 ml, 31.2 mmol) was added dropwise while maintaining the temperature below −75° C. The reaction mixture was stirred at this temperature for 45 to 60 min and tri(isopropyl)borate (3.6 ml, 15.6 mmol) was added slowly while maintaining the temperature below −70° C. and the mixture was stirred for 1 h at −78° C. and slowly warmed up to r.t. A saturated solution of ammonium chloride (50 ml) was added followed by water (20 ml) and diethyl ether (50 ml) while stirring vigorously. The phases were separated and the aqueous extracted with EtOAc (50 ml). The organic phase was dried over magnesium sulfate, filtered and evaporated in vacuo. The crude product was purified on column (DCM/EtOAc 9:1 then flush with IPA) to yield the expected product (2.45 g, 55%). LCMS purity 77%, m/z 286 [M$^+$+H]$^+$.

Stage 3: {4-[4-(Benzyloxycarbonylamino-methyl)-phenoxy]-phenyl}-(S)-tert-butoxycarbonylamino-acetic acid cyclopentyl ester

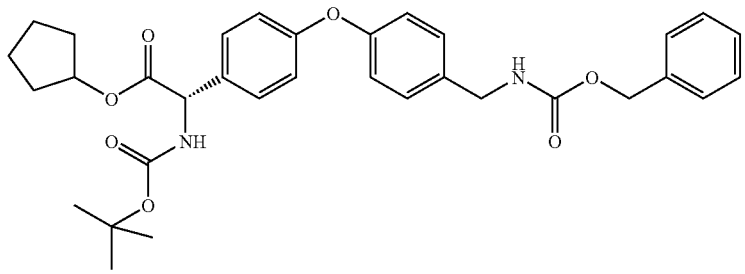

Stage 3 boronic acid (500 mg, 1.75 mmol) and (S)-tert-butoxycarbonylamino-(4-hydroxy-phenyl)-acetic acid cyclopentyl ester (Scheme 11) (294 mg, 0.88 mmol) were stirred in DCM (10 ml) with copper acetate (159 mg, 0.88 mmol) and molecular sieves. Pyridine (0.36 ml, 4.4 mmol) and triethylamine (0.62 ml, 4.4 mmol) were added and reaction mixture was stirred for 4.5 h at r.t. under an ambient atmosphere. The reaction mixture was filtered, the residue washed with DCM (2×10 ml) and the filtrate was evaporated in vacuo. The crude product was purified on silica (DCM/EtOAc 9:1 to 1:1) to yield the expected product (479 mg, 95% yield). LCMS purity 87%, m/z 597 [M$^+$+Na]$^+$.

Stage 4: (S)-[4-(4-Aminomethyl-phenoxy)-phenyl]-tert-Butoxycarbonylamino-acetic acid cyclopentyl ester

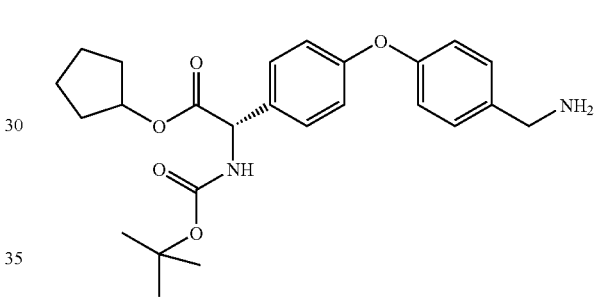

Stage 3 Cbz protected amine (478 mg, 1.1 mmol) was stirred in EtOAc (20 ml) in the presence of Pd/C 10% wet (48 mg) under a hydrogen atmosphere overnight. The mixture was filtered through a pad of celite and the filtrate was evaporated in vacuo to yield the expected product (261 mg, 56% yield). LCMS purity 85%, m/z 441 [M$^+$+H]$^+$.

Stage 5: (S)-tert-Butoxycarbonylamino-{4-[4-({[2-(1-isobutoxy-ethoxycarbamoyl)-benzo[b]thiophen-6-ylmethyl]-amino}-methyl)-phenoxy]-phenyl}-acetic acid cyclopentyl ester

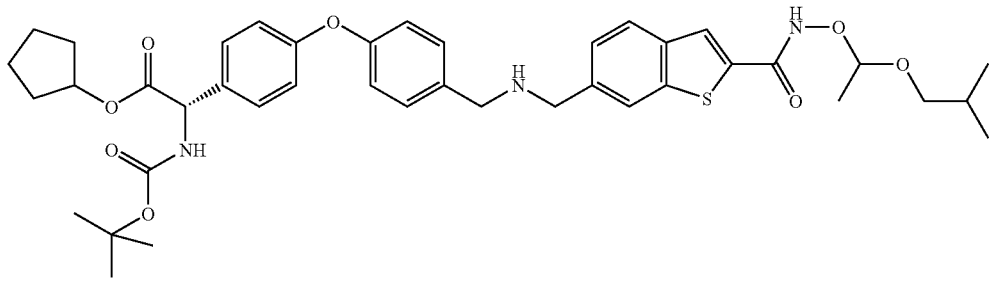

Stage 4 amine (260 mg, 0.6 mmol) and 6-formyl-benzo[b]thiophene-2-carboxylic acid (1-isobutoxy-ethoxy) amide (Scheme 11) (173 mg, 0.5 mmol) was stirred in DCE (5 ml) for 30 min. AcOH (3 ul, 0.05 mmol) and sodium triacetoxyborohydride (343 mg, 1.6 mmol) were added and the reaction mixture was stirred for 1 h at r.t. DCM (5 ml) and a saturated solution of NaHCO$_3$ (10 ml) were added, phases were separated and the aqueous were extracted with EtOAc (10 ml). The organics phases were dried over magnesium sulfate, filtered and evaporated to dryness. The crude product was purified on silica column (EtOAc) to yield the expected pure product (107 mg, 27% yield). $^1$H NMR (300 MHz, CDCl$_3$), δ: 0.96 (6 H, dd, J=6.6, 1.5 Hz, 2×CH$_3$), 1.44 (9 H, s, 3×CH$_3$), 1.48 (3 H, d, J=5.5 Hz, CH$_3$), 1.50-1.59 (4 H, m, 2×CH$_2$), 1.63-1.81 (4 H, m, 2×CH$_2$), 3.39 (1 H, dd, J=9.4, 6.6 Hz, CH), 3.64 (1 H, dd, J=9.3, 6.7 Hz, CH), 3.83 (2 H, s, CH$_2$NH), 3.96 (2 H, s, CH$_2$NH), 5.11 (1 H, q, J=5.3 Hz, CH), 5.16-5.28 (2 H, m, CH$_2$), 5.58 (1 H, br. s, CH), 6.91-7.01 (5 H, m, Ar), 7.28-7.36 (4 H, m, Ar), 7.40 (1 H, dd, J=8.3, 1.1 Hz, Ar), 7.80 (1 H, d, J=8.1 Hz, Ar), 7.86 (2 H, s, Ar)

Stage 6: (S)-Amino-[4-(4-{[(2-hydroxycarbamoyl-benzo[b]thiophen-6-ylmethyl)-amino]-methyl}-phenoxy)-phenyl]-acetic acid cyclopentyl ester (24)

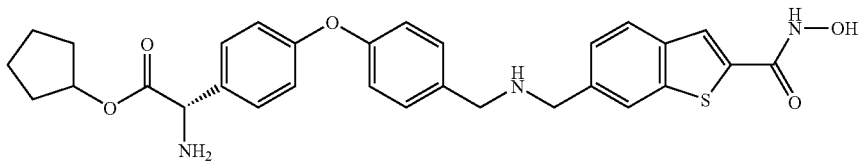

Stage 5 amine (107 mg, 0.14 mmol) was stirred with 4N HCl in dioxane (0.5 ml) and DCM (2 ml) for 30 min and evaporated to dryness. The crude product was purified on reverse phase column (H$_2$O to H$_2$O/MeOH 1:1) to yield Compound 24 as a clear oil. LCMS purity 92%, m/z 546 [M$^+$+H]$^+$. $^1$H NMR (300 MHz, MeOD), δ: 1.47-1.95 (8H, m, 4×CH$_2$), 3.36 (2H, s, CH$_2$), 4.32 (2H, s, CH$_2$NH), 4.43 (2H, s, CH$_2$NH), 5.16 (1H, s, CHNH), 5.27-5.35 (1H, m, CHOCyp), 7.07-7.16 (4H, m, Ar), 7.46-7.53 (2H, m, Ar), 7.54-7.63 (3H, m, Ar), 8.01 (1H, d, J=8.3 Hz, Ar), 8.11 (1H, s, Ar).

Stage 7: (S)-Amino-[4-(4-{[(2-hydroxycarbamoyl-benzo[b]thiophen-6-ylmethyl)-amino]-methyl}-phenoxy)-phenyl]-acetic acid (25)

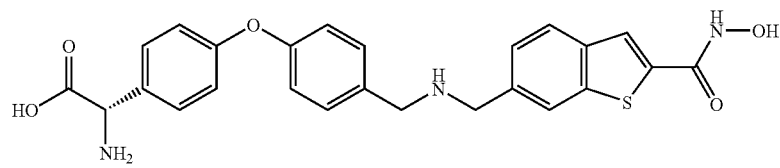

Stage 6 cyclopentyl ester (22 mg) was dissolved in THF (2 ml) and 2M LiOH (aq, 2 ml) added. The reaction was stirred at r.t. overnight. The reaction mixture was evaporated to dryness and the crude product deprotected by stirring in 4N HCl in dioxane (1 ml) for 1 h. The mixture was evaporated to dryness again and purified by reverse phase column chromatography (H$_2$O to H$_2$O/MeOH 1:1) to yield Compound 25. LCMS purity 94%, m/z 478 [M$^+$+H]$^+$, 1H NMR (300 MHz, d6-DMSO), δ: 4.03 (2H, br. s, CH$_2$NH), 4.17 (2H, br. s, CH$_2$NH), 4.34 (1H, br. s, CH$_2$), 6.88-7.09 (4H, m, Ar), 7.34-7.58 (5H, m, Ar), 7.93 (2H, s, Ar), 8.08 (1H, s, Ar), 11.53 (1H, s, COOH)

The following compounds were prepared in a similar manner to Compound (24) and Compound (25) using the appropriate intermediates (see Scheme 12).

(S)-2-Amino-3-[4-(4-{[(2-hydroxycarbamoyl-benzo[b]thiophen-6-ylmethyl)-amino]-methyl}-phenoxy)-phenyl]-propionic acid cyclopentyl ester (26)

LCMS purity 95%, m/z 560 [M$^+$+H]$^+$, $^1$H NMR (300 MHz, MeOD), δ: 1.52-1.73 (6H, m, 3×CH$_2$), 1.77-1.96 (2H, m, CH$_2$), 3.17 (2H, d, J=7.3 Hz, CH$_2$CH), 3.66 (1H, s, CH), 4.27 (2H, s, CH$_2$NH), 4.40 (2H, s, CH$_2$NH), 5.19-5.28 (1H, m, CHOCyp), 6.99-7.10 (4H, m, Ar), 7.27-7.33 (2H, m, Ar), 7.46-7.51 (2H, m, Ar), 7.54 (1H, dd, J=8.3, 1.5 Hz, Ar), 7.87 (1H, s, Ar), 7.99 (1H, s, Ar), 8.06 (1H, s, Ar).

(S)-2-Amino-3-[4-(4-{[(2-hydroxycarbamoyl-benzo[b]thiophen-6-ylmethyl)-amino]-methyl}-phenoxy)-phenyl]-propionic acid (27)

LCMS purity 95%, m/z 492 [M$^+$+H]$^+$, $^1$H NMR (300 MHz, d6-DMSO), δ: 3.09 (2H, d, J=6.6 Hz, CH$_2$CH), 3.70 (2H, s, CH$_2$NH), 4.14 (1H, br. s, CH), 4.26 (2H, br. s, CH$_2$NH), 6.93-7.06 (4H, m, Ar), 7.23-7.34 (2H, m, Ar), 7.48-7.62 (3H, m, Ar), 7.93-8.02 (2H, m, Ar), 8.15 (1H, s, Ar), 9.33 (1H, br. s, COOH)

Synthesis of Compounds Outlined in FIG. 4 Exemplified by: Compound 28 and Compound 29

Stage 1: 2(S)-tert-Butoxycarbonylamino-3-(4-hydroxy-cyclohexyl)-propionic acid cyclopentyl ester

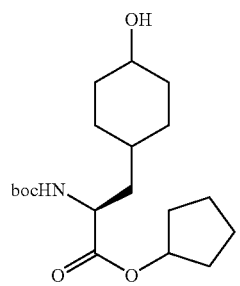

(S)-2-tert-Butoxycarbonylamino-3-(4-hydroxy-phenyl)-propionic acid cyclopentyl ester (Scheme 12) (2.35 g, 9.5 mmol) in isopropanol (40 ml) was placed in a glass insert (120 ml volume). PtO$_2$ (0.47 g, 2.1 mmol) was added to the glass insert which was placed in a hydrogenation bomb. Acetic acid (3 ml) was placed in a glass vial in the bomb next to the glass insert. The bomb was sealed and the reaction stirred for 16 h under an atmosphere of hydrogen (5 bar pressure). The reaction mixture was filtered through celite and washed with isopropanol. The solvent was removed in vacuo and azeotroped with THF to remove excess isopropanol to furnish the 2.58 g (quantitative yield) of the desired product.

Note: Acetic acid vapour was required for successful reaction. It is important that the acetic acid is not added to the reaction mixture but the presence of the open vial in the bomb promotes the reaction.

Figure 4

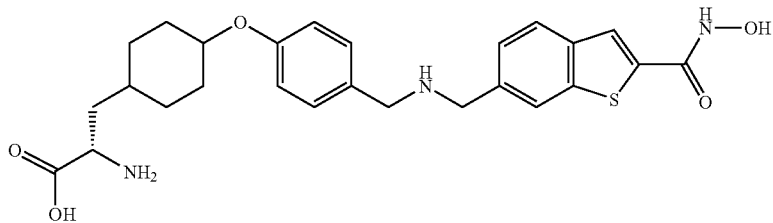

R = cyclopentyl  28
R = H           29

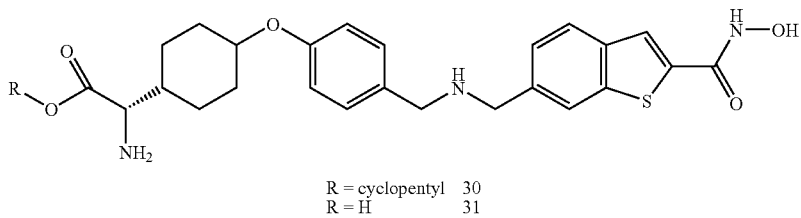

R = cyclopentyl  30
R = H           31

Stage 2: (4-Hydroxy-benzyl)-carbamic acid benzyl ester

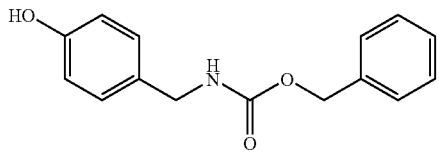

A solution of 4-hydroxybenzylamine (1 g, 8.1 mmol) in THF (20 ml) and water (20 ml) was cooled down to 0° C. with sodium hydroxide (357 mg, 8.9 mmol). Benzyl chloroformate (1.27 ml, 8.9 mmol) was added slowly and the reaction mixture was stirred at 0° C. for 1 h and at r.t. for 18 hours. Brine (20 ml) and ethyl acetate (20 mL) were added and the phases were separated. The aqueous phase was extracted with EtOAc (20 mL). The organic phase was dried over magnesium sulfate, filtered and concentrated to dryness to yield a light pink solid (2.45 g, 100%). $^1$H NMR (300 MHz, CDCl$_3$), δ: 4.30 (2 H, d, J=5.8 Hz, CH$_2$NH), 5.15 (2 H, s, OCH$_2$), 6.67 (1 H, br. s, NH), 6.78 (2 H, d, J=8.5 Hz, Ar), 7.12 (2 H, d, J=8.1 Hz, Ar), 7.29-7.44 (5 H, m, Ar)

Stage 3: 3-{4-[4-(Benzyloxycarbonylamino-methyl)-phenoxy]-cyclohexyl}-2-(S)-tert-butoxycarbonylamino-propionic acid cyclopentyl ester

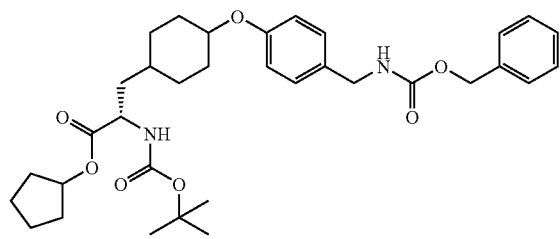

Stage 2 phenol (500 mg, 1.9 mmol) and stage 1 alcohol (725 mg, 2.0 mmol) were stirred in THF (4.5 ml) with triphenylphosphine (535 mg, 2.0 mmol) for 10 min at r.t. DIAD (413 mg, 2.0 mmol) was added dropwise and the mixture was stirred at r.t. for 1.5 h then evaporated to dryness. The crude product was purified on silica column (heptane/EtOAc 1:1) to yield the title product (986 mg, 85% yield). LCMS purity 100%, m/z 617 [M$^+$+Na]$^+$.

Stage 4: 3-[4-(4-Aminomethyl-phenoxy)-cyclohexyl]-2-(S)-tert-butoxycarbonylamino-propionic acid cyclopentyl ester

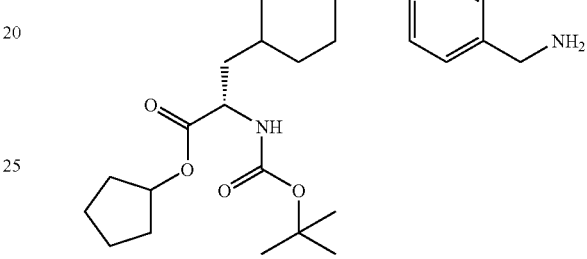

Stage 3: Cbz protected amine (986 mg, 1.7 mmol) was stirred in EtOAc in the presence of Pd/C [10% wet] (48 mg) under a hydrogen atmosphere overnight. The mixture was filtered through a pad of celite and the filtrate was evaporated in vacuo to yield the expected product (925 mg, 100% yield). LCMS purity 100%, m/z 461 [M$^+$+H]$^+$.

Stage 5: 2-(S)-tert-Butoxycarbonylamino-3-{4-[4-({[2-(1-isobutoxy-ethoxycarbamoyl)-benzo[b]thiophen-6-ylmethyl]-amino}-methyl)-phenoxy]-cyclohexyl}-propionic acid cyclopentyl ester

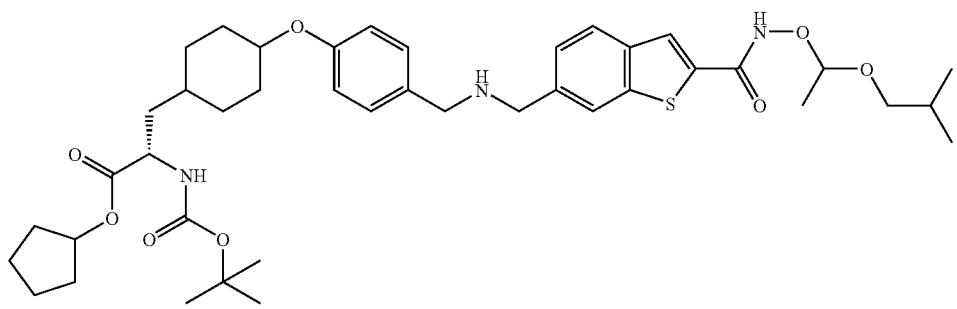

Stage 4 amine (800 mg, 1.7 mmol) and 6-formyl-benzo[b]thiophene-2-carboxylic acid (1-isobutoxy-ethoxy) amide (Scheme 13) (507 mg, 1.6 mmol) were stirred in DCE (8 ml) for 30 minutes. Acetic acid (9 ul, 0.16 mmol) and sodium triacetoxyborohydride (1 g, 4.7 mmol) were added and the reaction mixture was stirred for 1 h at r.t. DCM (5 ml) and a saturated solution of NaHCO$_3$ (10 ml) were added, phases were separated and the aqueous were extracted with EtOAc. The organics phases were dried over magnesium sulfate, filtered and evaporated to dryness. The crude product was purified on silica column (DCM/EtOAc 1:1 to neat EtOAc) to yield the expected clean product (157 mg, 13% yield). LCMS purity >90%, m/z 767 [M$^+$+H]$^+$.

Stage 6: 2-(S)-Amino-3-[4-(4-{[(2-hydroxycarbamoyl-benzo[b]thiophen-6-ylmethyl)-amino]-methyl}-phenoxy)-cyclohexyl]-propionic acid cyclopentyl ester (28)

$^1$H NMR (300 MHz, d6-DMSO), δ: 1.18-1.73 (8H, m, 4×CH$_2$), 1.76-1.91 (3H, m, CH$_2$ and CH), 3.74 (1H, br. s, OCH), 4.04 (2H, br. s, CH$_2$NH), 4.21 (2H, br. s, CH$_2$NH), 4.59 (1H, br. s, CH), 6.96 (2H, d, J=8.3 Hz, Ar), 7.36 (2H, d, J=8.7 Hz, Ar), 7.52 (1H, d, J=1.5 Hz, Ar), 7.91-7.99 (2H, m, Ar), 8.08 (1H, s, Ar).

The following compounds were prepared in a similar manner to Compound (28) and Compound (29) using the appropriate intermediates (see Scheme 11).

Amino-[4-(4-{[(2-hydroxycarbamoyl-benzo[b]thiophen-6-ylmethyl)-amino]-methyl}-phenoxy)-cyclohexyl]-acetic acid cyclopentyl ester (30)

LCMS purity 98%, m/z 552 [M$^+$+H]$^+$, $^1$H NMR (300 MHz, MeOD), δ: 1.40-1.60 (2H, m, CH$_2$), 1.61-1.87 (10H, m, 5×CH$_2$), 1.88-2.04 (3H, m, CH$_2$ and CH), 2.05-2.30 (2H, m,

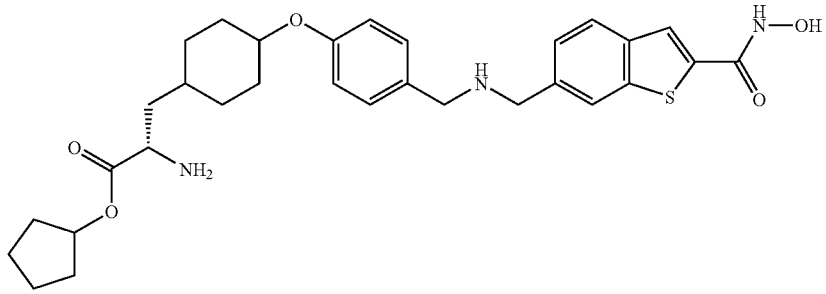

Stage 5 product (157 mg, 0.2 mmol) was stirred with 4N HCl in dioxane (0.2 ml) and DCM (1 ml) for 1 h and evaporated to dryness. The crude product was purified on reverse phase column (H$_2$O to H$_2$O/MeOH 1:1) to yield Compound 28 as a clear oil. LCMS purity 88%, m/z 566 [M$^+$+H]$^+$. $^1$H NMR (300 MHz, MeOD), δ: 1.57-1.87 (12H, m, 6×CH$_2$), 1.87-2.11 (5H, m, 2×CH$_2$ and CH), 3.99-4.10 (2H, t, CH$_2$), 4.23 (2H, s, CH$_2$NH), 4.38 (2H, s, CH$_2$NH), 4.67 (1H, br. s, CH), 5.33 (1H, m, CHOCyp), 6.98-7.05 (2H, m, Ar), 7.39-7.46 (2H, m, Ar), 7.55 (1H, dd, J=8.4, 1.4 Hz, Ar), 7.88 (1H, s, Ar), 8.00 (1H, d, J=8.3 Hz, Ar), 8.06 (1H, s, Ar).

Stage 7: 2-(S)-Amino-3-[4-(4-{[(2-hydroxycarbamoyl-benzo[b]thiophen-6-ylmethyl)-amino]-methyl}-phenoxy)-cyclohexyl]-propionic acid (29)

CH$_2$), 3.90 (1H, d, J=4.3 Hz, CH), 4.22 (2H, d, J=2.1 Hz, CH$_2$NH), 4.37 (2H, s, CH$_2$NH), 5.30-5.38 (1H, m, CHOCyp), 6.96-7.04 (2H, m, Ar), 7.41 (2H, dd, J=8.7, 5.1 Hz, Ar), 7.52 (1H, d, Ar), 7.87 (1 H, s, Ar), 7.99 (1H, d, J=8.3 Hz, Ar), 8.05 (1H, s, Ar).

Amino-[4(4-{[(2-hydroxycarbamoyl-benzo[b]thiophen-6-ylmethyl)-amino]-methyl}-phenoxy)-cyclohexyl]-acetic acid (31)

LCMS purity 90%, m/z 484 [M$^+$+H]$^+$, $^1$H NMR (300 MHz, d6-DMSO), δ: 1.16-1.38 (3 H, m, CH$_2$ and CH), 1.42-1.86 (3 H, m, CH$_2$ and CH), 1.99-2.15 (2 H, m, CH$_2$), 2.60-2.66 (1 H, m, CH), 4.01 (2 H, m, CH$_2$NH), 4.17 (2 H, m, CH$_2$NH), 6.93 (2 H, d, J=8.7 Hz, Ar), 7.34 (2 H, d, J=8.7 Hz, Ar), 7.46-7.54 (1 H, m, Ar), 7.89-7.99 (2 H, m, Ar), 8.07 (1 H, s, Ar)

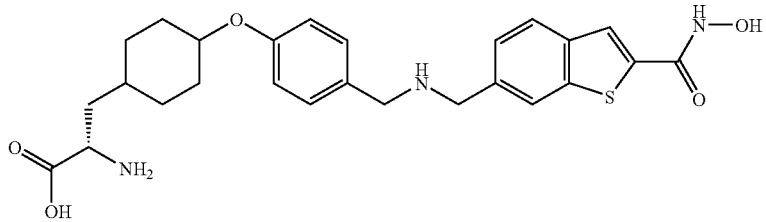

Stage 6 cyclopentyl ester (22 mg) was dissolved in THF (2 ml) and 2M LiOH (aq, 2 ml) was added. The reaction was stirred at 50° C. for 8 h then evaporated to dryness. The crude product was deprotected by stirring in 4N HCl in dioxane (1 ml) for 1 h. The mixture was evaporated to dryness again and purified on reverse phase column (H$_2$O to H$_2$O/MeOH 1:1) to yield Compound 29. LCMS purity 89%, m/z 498 [M$^+$+H]$^+$, Measurement of Biological Activities Histone Deacetylase Activity The ability of compounds to inhibit histone deacetylase activities was measured using the commercially available HDAC fluorescent activity assay from Biomol. In brief, the Fluor de Lys™ substrate, a lysine with an epsilon-amino acetylation, is incubated with the source of histone deacetylase activity (HeLa nuclear extract) in the presence or absence of inhibitor.

Deacetylation of the substrate sensitises the substrate to Fluor de Lys™ developer, which generates a fluorophore. Thus, incubation of the substrate with a source of HDAC activity results in an increase in signal that is diminished in the presence of an HDAC inhibitor.

Data are expressed as a percentage of the control, measured in the absence of inhibitor, with background signal being subtracted from all samples, as follows: —

$$\% \text{ activity} = ((S^i - B)/(S^o - B)) \times 100$$

where $S^i$ is the signal in the presence of substrate, enzyme and inhibitor, $S^o$ is the signal in the presence of substrate, enzyme and the vehicle in which the inhibitor is dissolved, and B is the background signal measured in the absence of enzyme.

IC50 values were determined by non-linear regression analysis, after fitting the results of eight data points to the equation for sigmoidal dose response with variable slope (% activity against log concentration of compound), using Graphpad Prism software.

Histone deacetylase activity from crude nuclear extract derived from HeLa cells was used for screening. The preparation, purchased from 4C (Seneffe, Belgium), was prepared from HeLa cells harvested whilst in exponential growth phase. The nuclear extract is prepared according to Dignam JD1983 Nucl. Acid. Res. 11, 1475-1489, snap frozen in liquid nitrogen and stored at −80° C. The final buffer composition was 20 mM Hepes, 100 mM KCl, 0.2 mM EDTA, 0.5 mM DTT, 0.2 mM PMSF and 20% (v/v) glycerol.

$IC_{50}$ results were allocated to one of 3 ranges as follows:
Range A: IC50<100 nM,
Range B: IC50 from 101 nM to 1000 nM;
Range C: IC50>1001 nM.
NT=Not tested Results of testing the compounds of the examples in this assay are given in the second column of Table 1 below.

Cell Inhibition Assays

The corresponding cancer cell lines (Hela, U937 and HUT) growing in log phase were harvested and seeded at 1000 cells/well (200 ul final volume) into 96-well tissue culture plates. Following 24 h of cell growth cells were treated with compounds (final concentration of 20 uM). Plates were then re-incubated for a further 72 h before a sulphorhodamine B (SRB) cell viability assay was conducted according to Skehan 1990 J Natl Canc Inst 82, 1107-1112.

Data were expressed as a percentage inhibition of the control, measured in the absence of inhibitor, as follows: —

$$\% \text{ inhibition} = 100 - ((S^i/S^o) \times 100)$$

where $S^i$ is the signal in the presence of inhibitor and $S^o$ is the signal in the presence of DMSO.

IC50 values were determined by non-linear regression analysis, after fitting the results of eight data points to the equation for sigmoidal dose response with variable slope (% activity against log concentration of compound), using Graphpad Prism software. IC50 results were allocated to one of 3 ranges as follows:
Range A: IC50<330 nM,
Range B: IC50 from 330 nM to 3300 nM;
Range C: $IC_{50}$>3301 nM.
NT=Not tested Results of testing the compounds of the examples in this assay are given in the third- fifth columns of Table 1.

TABLE 1

| Example No. | HDAC Activity | Hela | U937 | HUT |
|---|---|---|---|---|
| 1 | B | C | B | B |
| 2 | B | C | C | C |
| 3 | B | C | C | B |
| 4 | C | C | C | C |
| 5 | A | B | B | B |
| 6 | B | C | B | B |
| 7 | B | B | B | B |
| 8 | B | NT | NT | NT |
| 9 | A | A | A | A |
| 10 | A | NT | NT | NT |
| 11 | A | A | A | A |
| 12 | A | NT | NT | NT |
| 13 | A | A | A | A |
| 14 | A | NT | NT | NT |
| 15 | A | B | A | A |
| 16 | A | NT | NT | NT |
| 17 | A | B | B | B |
| 18 | B | NT | NT | NT |
| 19 | A | B | B | B |
| 20 | A | NT | NT | NT |
| 21 | A | B | B | A |
| 22 | B | B | B | B |
| 23 | A | NT | NT | NT |
| 24 | A | B | A | A |
| 25 | A | NT | NT | NT |
| 26 | A | B | A | A |
| 27 | A | NT | NT | NT |
| 28 | A | B | A | A |
| 29 | A | NT | NT | NT |
| 30 | A | B | A | A |
| 31 | A | NT | NT | NT |

The invention claimed is:
1. A compound of formula (I) or a salt or N-oxide thereof:

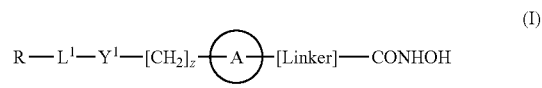

(I)

wherein
$Y^1$ is a bond, —(C═O)—, —S(O$_2$)—, —C(═O)—, —OC(═O)—, (C═O)NR$_3$—, —NR$_3$(C═O)—, —S(O$_2$)NR$_3$—, —NR$_3$S(O$_2$)—, or —NR$_3$(C═O) NR$_5$—, wherein R$_3$ and R$_5$ are independently hydrogen or optionally substituted (C$_1$-C$_6$)alkyl,
$L^1$ is a divalent radical of formula -(Alk$^1$)$_m$(Q)$_n$(Alk$^2$)$_p$- wherein
m, n and p are independently 0 or 1,
Q is (i) an optionally substituted divalent mono- or bicyclic carbocyclic or heterocyclic radical having 5 - 13 ring members, or (ii), in the case where p is 0, a divalent radical of formula -Q$^1$-X$^2$— wherein X$^2$ is —O—, —S—or NR$^A$—wherein R$^A$ is hydrogen or optionally substituted C$_1$-C$_3$ alkyl, and Q$^1$ is an optionally substituted divalent mono- or bicyclic carbocyclic or heterocyclic radical having 5 -13 ring members,
Alk$^1$ and Alk$^2$ independently represent optionally substituted divalent C$_3$-C$_7$ cycloalkyl radicals, or optionally substituted straight or branched, C$_1$-C$_6$ alkylene, C$_2$-C$_6$ alkenylene, or C$_2$-C$_6$ alkynylene radicals which may optionally contain or terminate in an ether (—O—), thioether (—S—) or amino (—NR$^A$—) link wherein R$^A$ is hydrogen or optionally substituted C$_1$-C$_3$ alkyl;
z is 0 or 1;

A represents an optionally substituted mono-, bi- or tricyclic carbocyclic or heterocyclic ring system; and -[Linker]- represents a divalent linker radical linking a ring atom in A with the hydroxamic acid group —CONHOH and selected from linkers represented by formulas identified in a, b, c, or d:

a. —(CH$_2$)$_x$—Z-L$^2$-wherein x is 0, Z is —C(=O)—, —NHC(=O)— or —C(=O)NH—, and L$^2$ is —(CH$_2$)$_5$—, —(CH$_2$)$_6$—, or —(CH$_2$)$_7$;

b. —(CH$_2$)$_x$-L$^3$-Ar$^1$-L$^4$-wherein x is 0, L$^3$ is —NHS(=O)$_2$—, —S(=O)$_2$NH—, —S(=O)$_2$— or a straight chain C$_3$-C$_5$ alkylene radical which may optionally contain an ether (—O—), thioether (—S—) or amino (—NR$^A$—) link wherein R$^A$ is hydrogen or optionally substituted C$_1$-C$_3$ alkyl, L$^4$ is —CH=CH— or —CH$_2$—, and Ar$^1$ is divalent radical selected from the following:

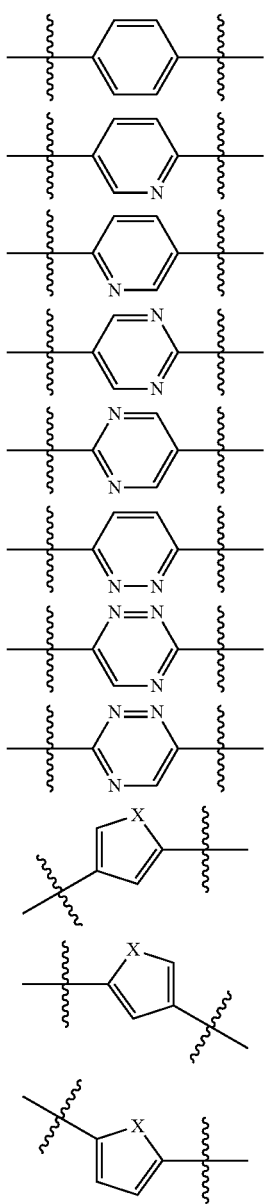

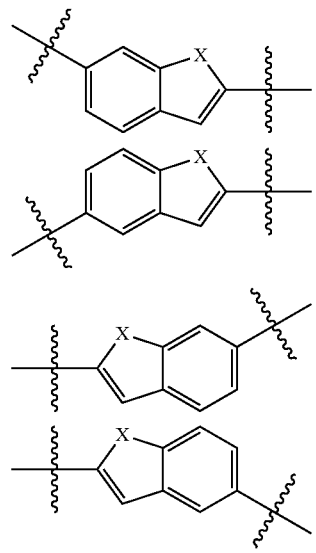

wherein X is O, S or NH;

c. —(CH$_2$)$_x$-L$^3$-Ar$^1$-L$^4$-, wherein x is 0, L$^3$ and L$^4$ are bonds, and Ar$^1$ is a divalent phenyl radical or a divalent bicyclic heteroaryl radical having 9 to 13 ring members;

d. —(CH$_2$)$_x$-L$^3$-B—Ar$^1$-L$^4$- wherein x is 0, Ar$^1$ is divalent radical selected from the following:

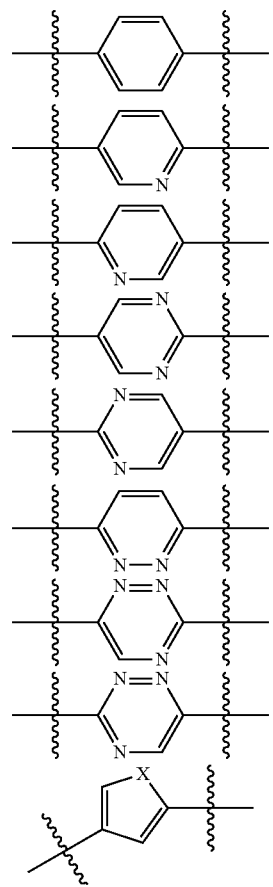

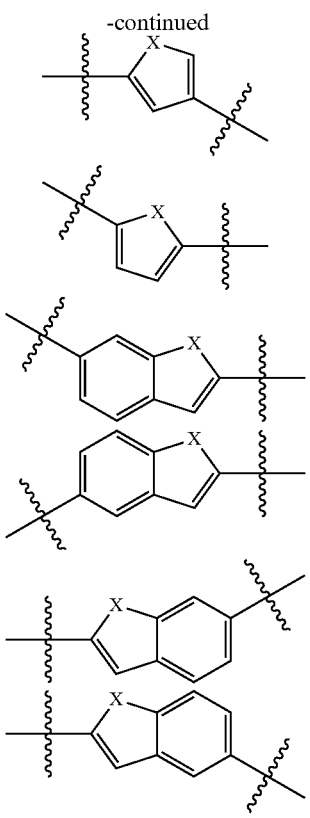

$L^3$ is a bond, —NHS(=O)$_2$—, —S(=O)$_2$NH—, —S(=O)$_2$— or a straight chain C$_3$-C$_5$ alkylene radical which may optionally contain an ether (—O—), thioether (—S—) or amino (—NR$^A$—) link wherein R$^A$ is hydrogen or optionally substituted C$_1$-C$_3$ alkyl, and L$^4$ is a bond, —CH=CH— or —CH$_2$—; and B is a mono- or bi-cyclic heterocyclic ring system; and R is a radical of formula (X) or (Y):

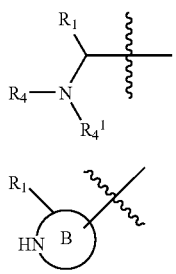

wherein

R$_1$ is a carboxylic acid group (—COOH), or an ester group which is hydrolysable by one or more intracellular carboxylesterase enzymes to a carboxylic acid group;

R$_4$ is hydrogen; or optionally substituted C$_1$-C$_6$ alkyl, C$_3$-C$_7$ cycloalkyl, aryl, aryl(C$_1$-C$_6$ alkyl)-, heteroaryl, heteroaryl(C$_1$-C$_6$ alkyl)-, —(C=O)R$_3$, —(C=O)OR$_3$, or —(C=O)NR$_3$ wherein R$_3$ is hydrogen or optionally substituted (C$_1$-C$_6$)alkyl, C$_3$-C$_7$ cycloalkyl, aryl, aryl (C$_1$-C$_6$ alkyl)-, heteroaryl, or heteroaryl(C$_1$-C$_6$ alkyl)-;

R$_4$$^1$ is hydrogen or optionally substituted C$_1$-C$_6$ alkyl; and

B is a monocyclic heterocyclic ring of 5 or 6 ring atoms wherein R$_1$ is linked to a ring carbon adjacent the ring nitrogen shown, and ring B is optionally fused to a second carbocyclic or heterocyclic ring of 5 or 6 ring atoms in which case the bond shown intersected by a wavy line may be from a ring atom in said second ring.

2. A compound as claimed in claim 1 wherein -[Linker]- represents a divalent radical of formula —(CH$_2$)$_x$—Z-L$^2$- wherein x is 0, Z is —C(=O)—, —NHC(=O)— or —C(=O)NH—, and L$^2$ is —(CH$_2$)$_5$—, —(CH$_2$)$_6$—, or —(CH$_2$)$_7$—.

3. A compound as claimed in claim 1 wherein-[Linker]- represents a divalent radical of formula —(CH$_2$)$_x$-L$^3$-Ar$^1$-L$^4$- wherein x is 0, L$^3$ is —NHS(=O)$_2$—, —S(=O)$_2$NH—, —S(=O)$_2$— or a straight chain C$_3$-C$_5$ alkylene radical which may optionally contain an ether (—O—), thioether (—S—) or amino (—NR$^A$—) link wherein R$^A$ is hydrogen or optionally substituted C$_1$-C$_3$ alkyl, L$^4$ is —CH=CH— or —CH$_2$—, and Ar$^1$ is divalent radical selected from the following:

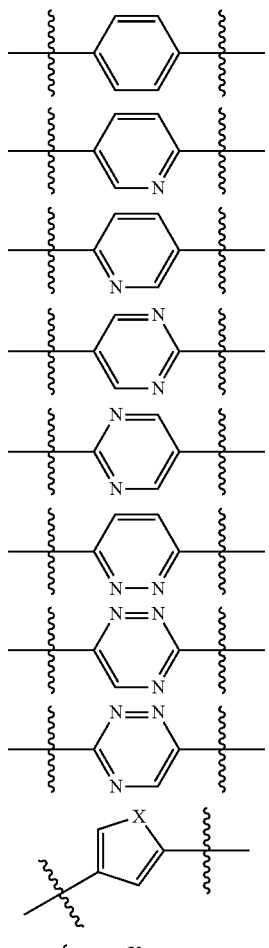

-continued

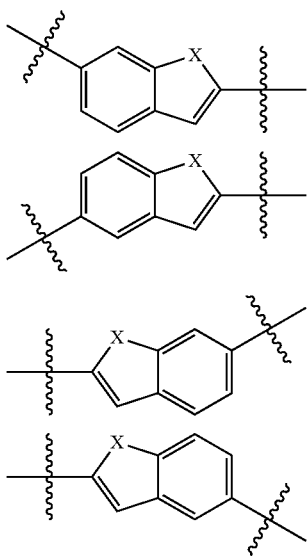

wherein X is O, S or NH.

4. A compound as claimed in claim 1 wherein -[Linker]- represents a divalent radical of formula —(CH$_2$)$_x$-L$^3$-Ar$^1$-L$^4$-, wherein x is 0, L$^3$ and L$^4$ are bonds, and Ar$^1$ is a divalent phenyl radical or a divalent bicyclic heteroaryl radical having 9 to 13 ring members.

5. A compound as claimed in claim 1 wherein -[Linker]- represents a divalent radical of formula —(CH$_2$)$_x$-L$^3$-B—Ar$^1$-L$^4$- wherein x is 0, Ar$^1$ is divalent radical selected from the following:

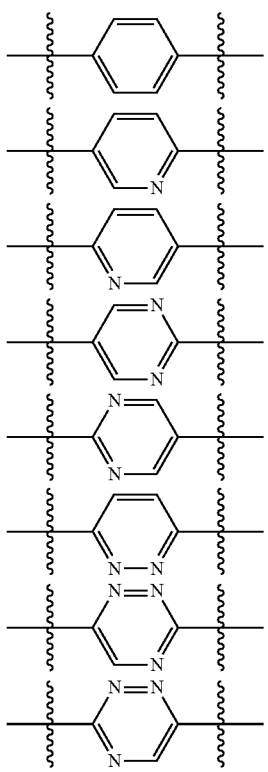

-continued

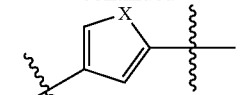
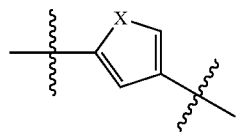
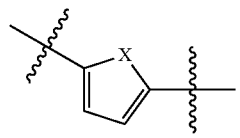
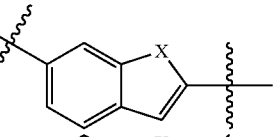
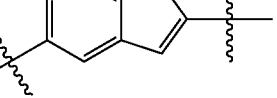
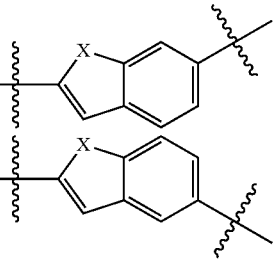

L$^3$ is a bond, —NHS(=O)$_2$—, —S(=O)$_2$NH—, —S(=O)$_2$—or a straight chain C$_3$-C$_5$ alkylene radical which may optionally contain an ether (—O—), thioether (—S—) or amino (—NR$^4$—) link wherein R$^4$ is hydrogen or optionally substituted C$_1$-C$_3$ alkyl, and L$^4$ is a bond, —CH=CH—or—CH$_2$-; X is O, S, or NH and B is a mono- or bi-cyclic heterocyclic ring system.

6. A compound as claimed in claim 5 wherein B is selected from the following:

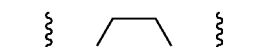
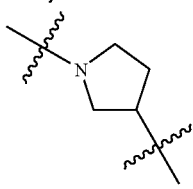
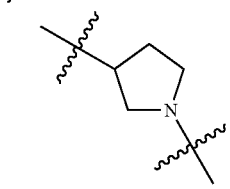

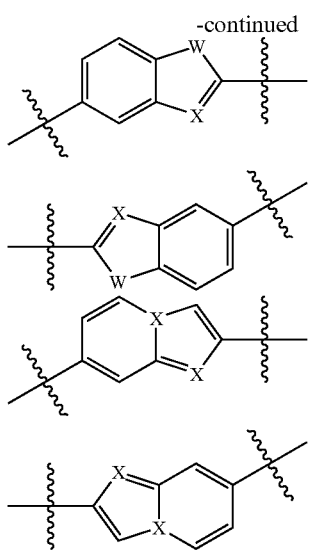
wherein X is N and W is NH, O or S.
7. A compound as claimed in claim 1 wherein A is one of the following ring systems, optionally substituted:
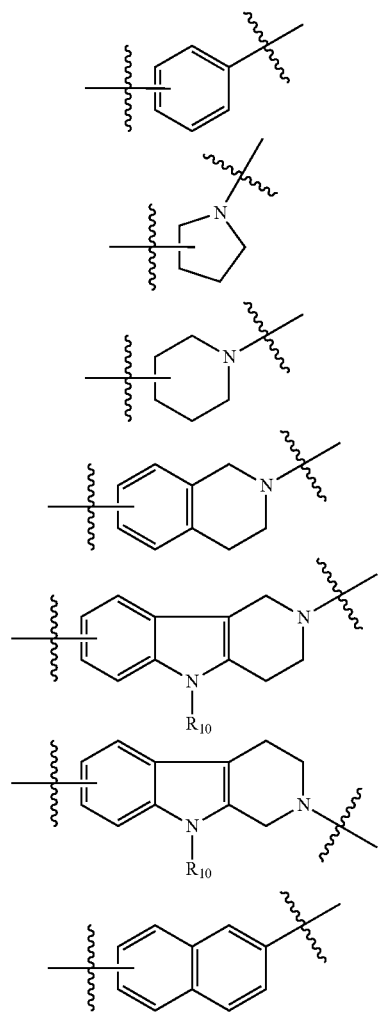
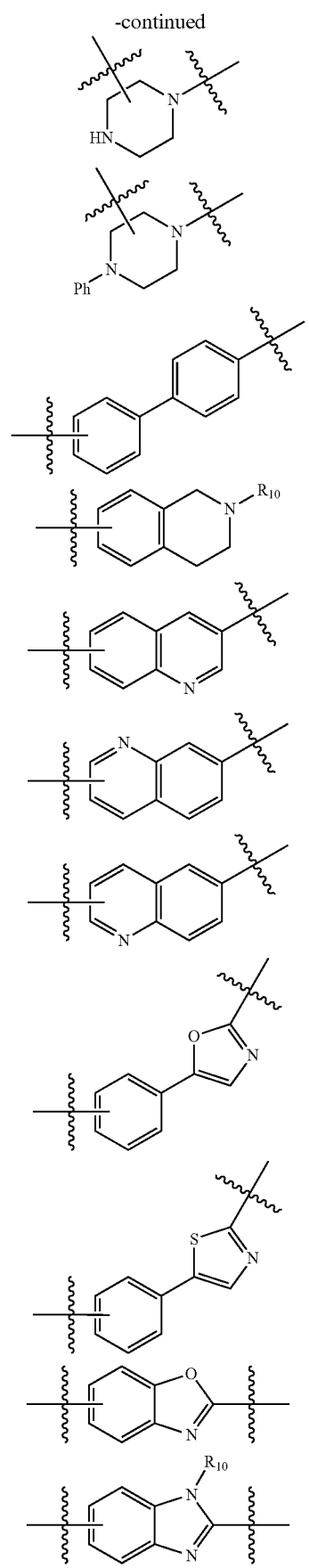

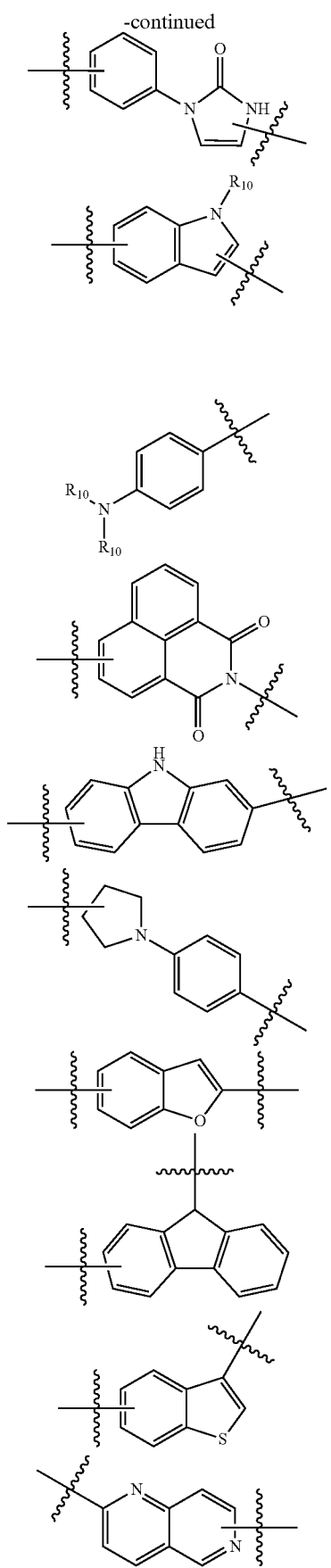
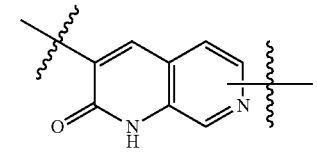
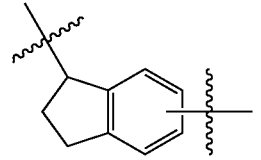
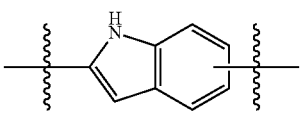
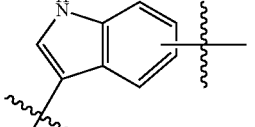
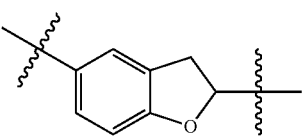
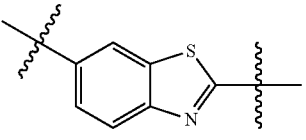
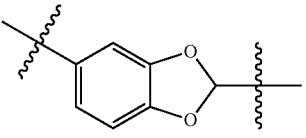
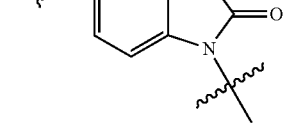
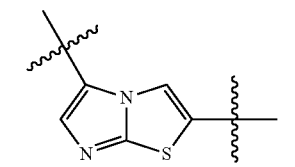
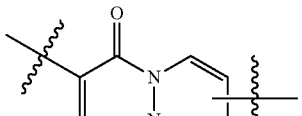
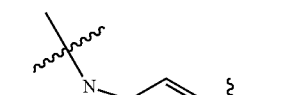
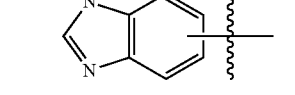

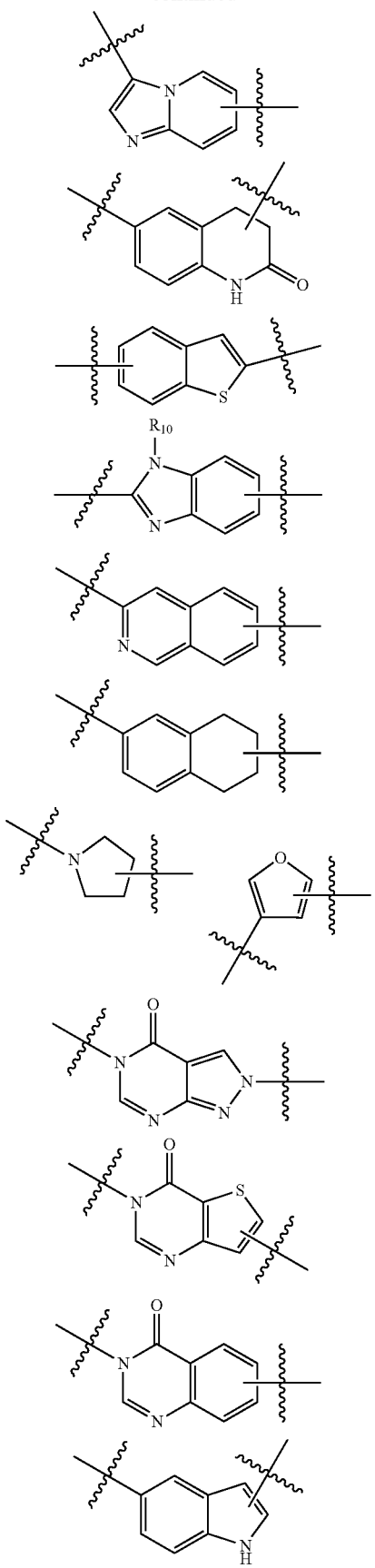
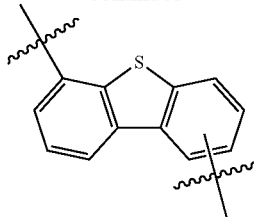

wherein $R_{10}$ is hydrogen or optionally substituted $C_1$-$C_6$ alkyl, the bond intersected by the wavy lines shown as connected to a fixed atom connects to the Linker radical in the compounds (I), and the other bond shown as floating links any convenient ring atom of the ring system shown to the grouping $RL^1Y^1[CH_2]_z$.

8. A compound as claimed in claim 1 wherein z is 0.

9. A compound as claimed in any claim 1 wherein $Y^1$ is a bond, —$NR_3$—, —S—, —O—, —C(=O)$NR_3$—, —$NR_3$C(=O)—, or —C(=O)O—, wherein $R_3$ is hydrogen or optionally substituted $C_1$-$C_6$ alkyl.

10. A compound as claimed in claim 1 wherein, in the radical $L^1$, $Alk^1$ and $Alk^2$, when present, are selected from —$CH_2$—, —$CH_2CH_2$—, —$CH_2CH_2CH_2$—, and divalent cyclopropyl, cyclopentyl and cyclohexyl radicals, and Q when present is a divalent phenylene radical or a mono-, or bi-cyclic heteroaryl radical having 5 to 13 ring members.

11. A compound as claimed in claim 1 wherein the radical -$L^1$-$Y^1$—[$CH_2$]$_z$— is selected from —($CH_2$)$_3$NH—, —$CH_2$C(=O)NH—, —$CH_2CH_2$C(=O)NH—, —$CH_2$C(O)O—, —$CH_2$S—, —$CH_2CH_2$C(O)O—, —($CH_2$)$_4$NH—, —$CH_2CH_2$S—, —$CH_2$O, —$CH_2CH_2$O—,

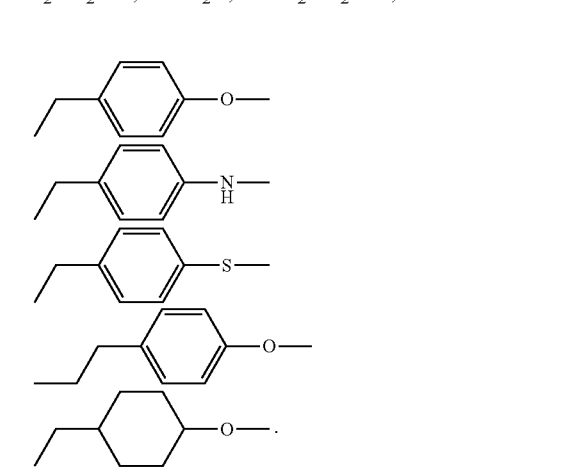

12. A compound as claimed in claim 1 wherein the radical -$L^1$-$Y^1$—[$CH_2$]$_z$— is —$CH_2$—.

13. A compound as claimed in claim 1 wherein $R_1$ is an ester group of formula —(C=O)$OR_9$ wherein $R_9$ is
(i) $R_7R_8$CH— wherein $R_7$ is optionally substituted ($C_1$-$C_3$) alkyl-($Z^1$)$_a$—($C_1$-$C_3$)alkyl- or ($C_2$-$C_3$)alkenyl-($Z^1$)$_a$—($C_1$-$C_3$)alkyl- wherein a is 0 or 1 and $Z^1$ is —O—, —S—, or —NH—, and $R_8$ is hydrogen or ($C_1$-$C_3$)alkyl- or $R_7$ and $R_8$ taken together with the carbon to which they are attached form an optionally substituted $C_3$-$C_7$ cycloalkyl ring or an optionally substituted heterocyclic ring of 5- or 6-ring atoms; or
(ii) optionally substituted phenyl or monocyclic heterocyclic having 5 or 6 ring atoms.

14. A compound as claimed in claim 13 wherein $R_9$ is methyl, ethyl, n- or iso-propyl, n- or sec-butyl, cyclohexyl, allyl, phenyl, benzyl, 2-, 3- or 4-pyridylmethyl, N-methylpiperidin-4-yl, tetrahydrofuran-3-yl or methoxyethyl.

15. A compound as claimed in claim 13 wherein $R_9$ is cyclopentyl.

16. A compound as claimed in claim 1 wherein R is a group of formula (X) wherein $R_4^1$ is hydrogen, and $R_4$ is hydrogen, methyl, ethyl, n-or isopropyl, cyclopropyl, cyclopentyl, cyclohexyl, phenyl, or pyridyl.

17. A compound as claimed in claim 1 wherein R is a group of formula (X) wherein $R_4^1$ and $R_4$ are each hydrogen.

18. A compound as claimed in claim 1 wherein R is a group of formula (Y) wherein ring or ring system B selected from the following:

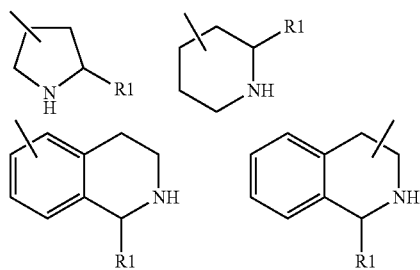

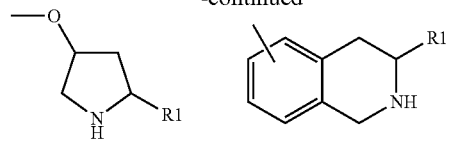

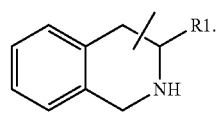

19. A compound as claimed in claim 1 having the structure of any of the compounds of the specific Examples herein.

20. A pharmaceutical composition comprising a compound as claimed in claim 1, together with a pharmaceutically acceptable carrier.

21. A pharmaceutical composition as claimed in claim 20 which is adapted for topical administration and wherein, in the compound, R is attached to a methylene (—$CH_2$—) radical.

* * * * *